US011407994B2

(12) United States Patent
Belgrader et al.

(10) Patent No.: US 11,407,994 B2
(45) Date of Patent: Aug. 9, 2022

(54) COMPOSITIONS, METHODS, MODULES AND INSTRUMENTS FOR AUTOMATED NUCLEIC ACID-GUIDED NUCLEASE EDITING IN MAMMALIAN CELLS VIA VIRAL DELIVERY

(71) Applicant: Inscripta, Inc., Boulder, CO (US)

(72) Inventors: Phillip Belgrader, Pleasanton, CA (US); Christian Siltanen, Boulder, CO (US); William Watterson, Boulder, CO (US); Burak Dura, Boulder, CO (US); Bruce Chabansky, Boulder, CO (US); David Stumbo, Boulder, CO (US); Eric Smith, Boulder, CO (US); Jorge Bernate, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

(21) Appl. No.: 17/584,298

(22) Filed: Jan. 25, 2022

(65) Prior Publication Data
US 2022/0145327 A1    May 12, 2022

Related U.S. Application Data

(63) Continuation of application No. 17/239,538, filed on Apr. 23, 2021, now Pat. No. 11,268,088.

(60) Provisional application No. 63/092,499, filed on Oct. 15, 2020, provisional application No. 63/014,944, filed on Apr. 24, 2020.

(51) Int. Cl.
| | |
|---|---|
| *C12N 5/00* | (2006.01) |
| *C12N 15/63* | (2006.01) |
| *C12N 15/85* | (2006.01) |
| *C07H 21/04* | (2006.01) |
| *C12N 15/10* | (2006.01) |
| *C12M 1/34* | (2006.01) |
| *C12M 1/26* | (2006.01) |
| *C12N 15/113* | (2010.01) |
| *C12N 15/86* | (2006.01) |
| *C12M 3/00* | (2006.01) |
| *C12M 3/04* | (2006.01) |
| *C12M 1/00* | (2006.01) |
| *C12N 5/074* | (2010.01) |
| *C12N 15/11* | (2006.01) |
| *C12N 15/88* | (2006.01) |
| *C12N 15/90* | (2006.01) |
| *B01L 3/00* | (2006.01) |
| *B01L 7/00* | (2006.01) |
| *C12M 1/32* | (2006.01) |

(Continued)

(52) U.S. Cl.
CPC .... *C12N 15/1082* (2013.01); *B01L 3/502761* (2013.01); *B01L 7/00* (2013.01); *C12M 23/12* (2013.01); *C12M 23/16* (2013.01); *C12M 23/42* (2013.01); *C12M 23/50* (2013.01); *C12M 27/10* (2013.01); *C12M 29/04* (2013.01); *C12M 33/14* (2013.01); *C12M 41/36* (2013.01); *C12M 43/00* (2013.01); *C12M 47/02* (2013.01); *C12M 47/04* (2013.01); *C12N 5/0696* (2013.01); *C12N 15/1065* (2013.01); *C12N 15/1068* (2013.01); *C12N 15/11* (2013.01); *C12N 15/113* (2013.01); *C12N 15/86* (2013.01); *C12N 15/88* (2013.01); *C12N 15/907* (2013.01); *B01L 2200/0647* (2013.01); *B01L 2300/0681* (2013.01); *B01L 2300/123* (2013.01); *B01L 2300/161* (2013.01); *B01L 2400/0415* (2013.01); *B01L 2400/0421* (2013.01); *B01L 2400/0424* (2013.01); *C12N 9/22* (2013.01); *C12N 2310/20* (2017.05); *C12N 2510/00* (2013.01); *C12N 2740/10011* (2013.01); *C12N 2740/15011* (2013.01); *C12N 2750/14111* (2013.01); *C12N 2800/80* (2013.01)

(58) Field of Classification Search
CPC ...... C12M 23/16; C12M 41/34; C12M 41/36; C12N 5/0696; C12N 15/63; C12N 15/85; C12N 15/86; C12N 2310/20; C12N 2510/00; C12N 2750/14111; C07H 21/02; C07H 21/04
See application file for complete search history.

(56) References Cited

U.S. PATENT DOCUMENTS

| | | |
|---|---|---|
| 6,391,582 B2 | 5/2002 | Ying et al. |
| 6,837,995 B1 | 1/2005 | Vassarotti et al. |
| (Continued) | | |

FOREIGN PATENT DOCUMENTS

| | | |
|---|---|---|
| EP | 2395087 | 12/2011 |
| EP | 3199632 | 8/2017 |
| (Continued) | | |

OTHER PUBLICATIONS

International Search Report and Written Opinion for International Application No. PCT/US20/19379, dated Jul. 22, 2020, p. 1-10.

(Continued)

*Primary Examiner* — Shin Lin Chen
(74) *Attorney, Agent, or Firm* — Sarah Brashears

(57) ABSTRACT

This invention relates to compositions of matter, methods, modules and instruments for automated mammalian cell growth and mammalian cell transduction followed by nucleic acid-guided nuclease editing in live mammalian cells. The present compositions and methods entail viral delivery of an editing cassette to live mammalian cells such that the editing cassettes edit the cells and the edited cells continue to grow, preferably using a fully-automated end-to-end instrument to process the cells without human intervention to enhance cell processing uniformity and to maintain the integrity of the cell culture.

30 Claims, 46 Drawing Sheets

(51) Int. Cl.
*C12M 3/06* (2006.01)
*C12N 9/22* (2006.01)

(56) References Cited

U.S. PATENT DOCUMENTS

| | | |
|---|---|---|
| 7,166,443 B2 | 1/2007 | Walker et al. |
| 8,332,160 B1 | 12/2012 | Platt et al. |
| 8,697,359 B1 | 4/2014 | Zhang et al. |
| 8,926,977 B2 | 1/2015 | Miller et al. |
| 9,260,505 B2 | 2/2016 | Weir et al. |
| 9,361,427 B2 | 6/2016 | Hillson |
| 9,499,855 B2 | 11/2016 | Hyde et al. |
| 9,776,138 B2 | 10/2017 | Innings et al. |
| 9,790,490 B2 | 10/2017 | Zhang et al. |
| 9,896,696 B2 | 2/2018 | Begemann et al. |
| 9,982,279 B1 | 5/2018 | Gill et al. |
| 9,988,624 B2 | 6/2018 | Serber et al. |
| 10,011,849 B1 | 7/2018 | Gill et al. |
| 10,017,760 B2 | 7/2018 | Gill et al. |
| 10,227,576 B1 | 3/2019 | Cameron et al. |
| 10,266,851 B2 | 4/2019 | Chen |
| 10,704,033 B1 | 7/2020 | Kim et al. |
| 10,724,021 B1 | 7/2020 | Kim et al. |
| 10,745,678 B1 | 8/2020 | Kim et al. |
| 10,767,169 B1 | 9/2020 | Kim et al. |
| 10,837,021 B1 | 11/2020 | Tian et al. |
| 10,927,385 B2 | 2/2021 | Kannan et al. |
| 2002/0139741 A1 | 10/2002 | Kopf |
| 2004/0110253 A1 | 6/2004 | Kappler et al. |
| 2006/0014137 A1 | 1/2006 | Ghosh et al. |
| 2007/0020761 A1 | 1/2007 | Yu et al. |
| 2010/0076057 A1 | 3/2010 | Sontheimer et al. |
| 2011/0294217 A1 | 12/2011 | McConnell-Smith et al. |
| 2013/0236970 A1 | 9/2013 | Anneren et al. |
| 2014/0068797 A1 | 3/2014 | Doudna et al. |
| 2014/0199767 A1 | 7/2014 | Barrangou et al. |
| 2014/0242033 A1 | 8/2014 | Gruber et al. |
| 2014/0273226 A1 | 9/2014 | Wu et al. |
| 2015/0024464 A1 | 1/2015 | Lippow et al. |
| 2015/0071898 A1 | 3/2015 | Liu et al. |
| 2015/0098954 A1 | 4/2015 | Hyde et al. |
| 2015/0159174 A1 | 6/2015 | Frendewey et al. |
| 2015/0176013 A1 | 6/2015 | Musunuru et al. |
| 2015/0191719 A1 | 7/2015 | Hudson et al. |
| 2015/0225732 A1 | 8/2015 | Williams et al. |
| 2015/0344549 A1 | 12/2015 | Muir et al. |
| 2016/0024529 A1 | 1/2016 | Carstens et al. |
| 2016/0053272 A1 | 2/2016 | Wurzel et al. |
| 2016/0053304 A1 | 2/2016 | Wurzel et al. |
| 2016/0076093 A1 | 3/2016 | Shendure et al. |
| 2016/0102322 A1 | 4/2016 | Ravinder et al. |
| 2016/0130608 A1 | 5/2016 | Doudna et al. |
| 2016/0168592 A1 | 6/2016 | Church et al. |
| 2016/0264981 A1 | 9/2016 | Yang et al. |
| 2016/0281053 A1 | 9/2016 | Sorek et al. |
| 2016/0289673 A1 | 10/2016 | Huang et al. |
| 2016/0298134 A1 | 10/2016 | Chen et al. |
| 2016/0354487 A1 | 12/2016 | Zhang et al. |
| 2017/0002339 A1 | 1/2017 | Barrngou et al. |
| 2017/0022499 A1 | 1/2017 | Lu et al. |
| 2017/0044525 A1 | 2/2017 | Kaper et al. |
| 2017/0051310 A1 | 2/2017 | Doudna et al. |
| 2017/0073705 A1 | 3/2017 | Chen et al. |
| 2017/0191123 A1 | 7/2017 | Kim et al. |
| 2017/0211078 A1 | 7/2017 | Kamineni et al. |
| 2017/0240922 A1 | 8/2017 | Gill et al. |
| 2017/0369870 A1 | 12/2017 | Gill et al. |
| 2018/0028567 A1 | 2/2018 | Li et al. |
| 2018/0052176 A1 | 2/2018 | Holt et al. |
| 2018/0073013 A1 | 3/2018 | Lorenz et al. |
| 2018/0112235 A1 | 4/2018 | Li et al. |
| 2018/0187149 A1 | 7/2018 | Ma et al. |
| 2018/0200342 A1 | 7/2018 | Bikard et al. |
| 2018/0203017 A1 | 7/2018 | Ting et al. |
| 2018/0230460 A1 | 8/2018 | Gill et al. |
| 2018/0230461 A1 | 8/2018 | Gill et al. |
| 2018/0284125 A1 | 10/2018 | Gordon et al. |
| 2018/0327761 A1 | 11/2018 | Duchateau et al. |
| 2018/0371498 A1 | 12/2018 | Gill et al. |
| 2019/0017072 A1 | 1/2019 | Ditommaso et al. |
| 2019/0085324 A1 | 3/2019 | Regev et al. |
| 2019/0136230 A1 | 5/2019 | Sather et al. |
| 2019/0169605 A1 | 6/2019 | Masquelier et al. |
| 2019/0194650 A1 | 6/2019 | Gill et al. |
| 2019/0225928 A1 | 7/2019 | Masquelier et al. |
| 2019/0270987 A1 | 9/2019 | Masquelier et al. |
| 2020/0071660 A1 | 3/2020 | Spindler et al. |
| 2020/0095533 A1 | 3/2020 | Garst et al. |
| 2020/0109398 A1 | 4/2020 | Rubens et al. |
| 2020/0216794 A1 | 7/2020 | Belgrader et al. |
| 2020/0263197 A1 | 8/2020 | Cheng et al. |
| 2020/0270632 A1 | 8/2020 | Roy et al. |

FOREIGN PATENT DOCUMENTS

| | | |
|---|---|---|
| WO | WO2002/010183 | 2/2002 |
| WO | WO 2003/087341 | 10/2003 |
| WO | WO 2010/079430 | 7/2010 |
| WO | WO 2011/072246 | 6/2011 |
| WO | WO 2011/143124 | 11/2011 |
| WO | WO 2013/142578 | 9/2013 |
| WO | WO 2013/176772 | 11/2013 |
| WO | WO 2014/018423 | 1/2014 |
| WO | WO2014/143381 | 9/2014 |
| WO | WO 2014/144495 | 9/2014 |
| WO | WO 2016/110453 | 7/2016 |
| WO | WO 2017/053902 | 3/2017 |
| WO | WO2017/075265 | 5/2017 |
| WO | WO 2017/078631 | 5/2017 |
| WO | WO 2017/083722 | 5/2017 |
| WO | WO2017/106414 | 6/2017 |
| WO | WO 2017/106414 | 6/2017 |
| WO | WO 2017/161371 | 9/2017 |
| WO | WO 2017/174329 | 10/2017 |
| WO | WO 2017/186718 | 11/2017 |
| WO | WO2017/212400 | 12/2017 |
| WO | WO 2017/216392 | 12/2017 |
| WO | WO 2017/223330 | 12/2017 |
| WO | WO 2018/031950 | 2/2018 |
| WO | WO 2018/071672 | 4/2018 |
| WO | WO2018/073391 | 4/2018 |
| WO | WO 2018/083339 | 5/2018 |
| WO | WO2018/152325 | 8/2018 |
| WO | WO2018/172556 | 9/2018 |
| WO | WO 2018/191715 | 10/2018 |
| WO | WO2019/006436 | 1/2019 |
| WO | WO2019/055878 | 3/2019 |
| WO | WO2019/200004 | 10/2019 |
| WO | WO2019/209926 | 10/2019 |
| WO | WO2020/005383 | 1/2020 |
| WO | WO2020/021045 | 1/2020 |
| WO | WO2020/074906 | 4/2020 |
| WO | WO2020/191102 | 9/2020 |
| WO | WO2020/191153 | 9/2020 |
| WO | WO2020/217057 | 10/2020 |
| WO | WO2021/207541 | 10/2021 |

OTHER PUBLICATIONS

International Search Report and Written Opinion for International Application No. PCT/US20/36064, dated Sep. 18, 2020, p. 1-16.
International Search Report and Written Opinion for International Application No. PCT/US20/40389, dated Oct. 13, 2020, p. 1-12.
Arnak, et al., "Yeast Artificial Chromosomes", John Wiley & Sons, Ltd., doi:10.1002/9780470015902.a0000379.pub3, pp. 1-10 (2012).
Woo, et al., "Dual roles of yeast Rad51 N-terminal domain in repairing DNA double-strand breaks", Nucleic Acids Research, doi:10.1093/nar/gkaa.587, vol. 48, No. 15, pp. 8474-8489 (2020).
International Search Report and Written Opinion for International Application No. PCT/US2021/012868, dated Mar. 26, 2021, p. 1-15.

(56) References Cited

OTHER PUBLICATIONS

Anzalone et al., "Search-and-replace genome editing without doubles-strand breaks or donor DNA," Nature, Oct. 21, 2019, vol. 576, No. 7785, pp. 149-157.
Alvarez, et al., "In vivo diversification of target genomic sites using processive T7 RNA polymerase-base deaminase fusions blocked by RNA-guided dCas9", Dept.of Microbial Biotechnology and Systems Biology Program, Madrid, Spain, Jan. 1, 2019, p. 1-33.
International Search Report and Written Opinion for International Application No. PCT/US20/65168, dated Mar. 17, 2021, p. 1-15.
International Search Report and Written Opinion for International Application No. PCT/US2020/038345, dated Nov. 23, 2020, p. 1-13.
International Search Report and Written Opinion for International Application No. PCT/US21/12867, dated May 12, 2021, p. 1-17.
International Search Report and Written Opinion for International Application No. PCT/US2020/064727, dated Apr. 28, 2021, p. 1-13.
International Search Report and Written Opinion for International Application No. PCT/US21/29008, dated Aug. 24, 2021, p. 1-19.
International Search Report and Written Opinion for International Application No. PCT/US21/29011, dated Aug. 24, 2021, p. 1-20.
Bauer, et al., "Cell-microcarrier Adhesion to Gas-Liquid Interfaces and Foam", Biotechnol. Prog. 2000, 16, 125-132, Oct. 19, 1999.
Datlinger, et al., "Pooled CRISPR screening with single-cell transcriptome readout", Nature Methods, Jan. 10, 2017; p. 1-10, doi:10.1038/nmeth.4177.
Dixit, et al., "Perturb-Seq: Dissecting Molecular Circuits with Scalable Single-Cell RNA Profiling of Pooled Genetic Screens", Cell 167, p. 1853-1866, Dec. 15, 2016.
GE Healthcare Life Sciences, "Microcarrier Cell Culture Principles and Methods", 18-1140-62 AC, p. 1-23, Nov. 2013.
Jacobi, et al., "Simplified CRISPR tools for efficient genome editing and streamlined protocols for their delivery into mammalian cells and mouse zygotes", Methods 121-122, p. 16-28, Mar. 23, 2017.
Jaitin, et al., "Dissecting Immune Circuits by Linking CRISPR-Pooled Screens with Single-Cell RNA-Seq", Cell 167, p. 1883-1896, Dec. 15, 2016.
Kim, et al., "Formation of Thermoresponsive Poly(N-isopropylacrylamide)/Dextran Particles by Atom Transfer Radical Polymerization", Macromol. Rapid Commun., 24, p. 517-521, 2003.
Kimple, et al., "Overview of Affinity Tags for Protein Purification", Curr Protoc Protein Sci.; 73: Unit-9-9. Doi:10.1002/0471140864. ps0909s73, p. 1-26, Aug. 6, 2015.
Nienow, et al., "A potentially scalable method for the harvesting of hMSCs from microcarriers", Biochemical Engineering Journal 85, p. 79-88, Feb. 4, 2014.
Replogle, et al., "Direct capture of CRISPR guides enables scalable, multiplexed, and multi-omic Perturb-Seq", bioRxiv; doi:http://dx.doi.org/10.1101/503367, p. 1-26, Dec. 21, 2018.
Sivalingam, et al., "Superior Red Blood Cell Generation from Human Pluripotent Stem Cells Through a Novel Microcarrier-Based Embryoid Body Platform", Tissue Engineering: Part C, vol. 22, No. 8, p. 765-780, Jun. 9, 2016.
International Search Report and Written Opinion for International Application No. PCT/US21/35807, dated Nov. 24, 2021, p. 1-21.
International Search Report and Written Opinion for International Application No. PCT/US21/50338, dated Dec. 10, 2021, p. 1-17.
International Search Report and Written Opinion for International Application No. PCT/US21/43097, dated Nov. 19, 2021, p. 1-12.
International Search Report and Written Opinion for International Application No. PCT/US21/39872, dated Oct. 27, 2021, p. 1-14.
International Search Report and Written Opinion for International Application No. PCT/US21/48566, dated Dec. 10, 2021, p. 1-10.
Filsinger, et al., "Characterizing the portability of RecT-mediated oligonucleotide recombination", bioRxiv, Apr. 15, 2020, doi:org/10.1101/2020.04.14.041095, p. 1-25.
Nelson, et al., "Engineered pegRNAs improve prime editing efficiency", Nature Biotechnology, Jul. 25, 2021, doi.org/10.1038/s41587-021-01039-7, p. 1-14.

Yu, et al., "Improved delivery of Cas9 protein/gRNA complexes using lipofectamine CRISPRMAX", Biotechnol Ltt, Feb. 18, 2016, doi 10.1007/s10529-016-2064-9, p. 919-929.
Bengali, et al., "Gene Delivery Through Cell Culture Substrate Adsorbed DNA Complexes", Biotechnol Bioeng., May 5, 2005, doi:10.1002/bit.20393, p. 1-23.
Segura, et al., "Substrate-mediated DNA delivery: role of the cationic polymer structure and extent of modification", Journal of Controlled Release, Aug. 9, 2003, doi:10.1016/j.jconrel.2003.08.003, p. 69-84.
Takahashi, et al., "Integration of CpG-free DNA induces de novo methylation of CpG islands in pluripotent stem cells," Science, May 5, 2017, vol. 356, No. 6337, pp. 1-7.
Chen, et al., "Human Pluripotent Stem Cell Culture: Considerations for Maintenance, Expansion, and Therapeutics", Cell Stem Cell, Jan. 2, 2014, doi.org/10.1016/j.stem.2013.12.005, p. 13-26.
Fayazpour, F., "Exploring New Applications For Photophysically Encoded Mircrocarriers", Ghent University Faculty of Pharmaceutical Sciences, Thesis Submission, Sep. 2008, 169 pages.
Chueng, et al., "Unlinking the methylome pattern from nucleotide sequence, revealed by large-scale in vivo genome engineering and methylome editing in medaka fish," PLoS Genetics, Dec. 21, 2017, vol. 13, No. 12, pp. 1-25.
Elvin, et al., "Modified bacteriophage lambda promoter vectors for overproduction of proteins in *Escherichia coli*", Gene, 87, Sep. 15, 1989, p. 123-126.
Segall-Shapiro, et al., "Engineered promoters enable constant gene expression at any copy number in bacteria", Nature Biotechology, vol. 36, No. 4, Mar. 19, 2018, p. 352-363.
Xing, et al., "A CRISPR/Cas9 toolkit for multiplex genome editing in plants", BMC Plant Biology, 2014, p. 1-12.
Sun, et al., "A Single Multiplex crRNA Array for FnCpf1-Mediated Human Genome Editing," Molecular Therapy, Aug. 1, 2018, vol. 26, No. 8, pp. 2070-2076.
Kurata, et al., "Highly multiplexed genome engineering using CRISPR/Cas9 gRNA arrays," PLoS ONE, Sep. 17, 2018, vol. 13, No. 9, pp. 1-17.
Hubmann, et al., "Natural and Modified Promoters for Tailored Metabolic Engineering of the Yeast *Saccharomyces cerevisiae*", Methods in Molecular Biology, vol. 1152, doi10.1007/978-1-4939-0563-8_2, p. 17-42.
Unciti-Broceta, et al., "Combining Nebulization-Mediated Transfection and Polymer Microarrays for the Rapid Determination of Optimal Transfection Substrates", Journal of Combinatorial Chemistry, vol. 10, No. 2, Feb. 5, 2008, p. 179-184.
Fayazpour, et al., "Evaluation of Digitally Encoded Layer-by-layer Coated Microparticles as Cell Carriers", Advanced Functional Materials, Sep. 1, 2008, p. 2716-2723.
UniProtKB/TrEMBL, "A0A1G4WF58_9FIRM", Nov. 22, 2017, rerieved from Internet: https://www.uniprot.org/uniprot/A0A_1G4WF58.txt, pp. 1-3.
Natsume, et al., "Conditional Degrons for Controlling Protein Expression at the Protein Level", Annual Review of Genetics, vol. 51, 2017, doi.org/10.1146/annurev-genet-120116-024656, p. 83-104.
Chen, et al., "Enhancing the copy number of episomal plasmids in *Saccharomyces cerevisiae* for improved protein production", FEMS Yeast Research, Apr. 25, 2012, doi:10.1111/j.1567-1364.2012.00809.x; p. 598-607.
Price, et al., "Expanding and understanding the CRISPR toolbox for Bacillus subtilis with MAD7 and dMAD7", Biotechnology and Bioengineering, Feb. 19, 2020, doi:10.1002/bit.27312 p. 1805-1816.
International Search Report and Written Opinion for International Application No. PCT/US21/43534, dated Nov. 10, 2021, p. 1-16.
International Search Report and Written Opinion for International Application No. PCT/US20/26095, dated Jul. 17, 2020, p. 1-10.
Anzalone, et al., "Programmable large DNA deletion, replacement, integration, and inversion with twin prime editing and site-specific recombinases", bioRxiv, Nov. 2, 2021, doi:10.1101/2021.11.01.466790, p. 1-51.
Horwitz, et al., "Efficient Multiplexed Integration of Synergistic Alleles and Metabolic Pathways in Yeasts via CRISPR-Cas", Cell Systems 1, Jul. 29, 2015, doi:10.1016/j.cels.2015.02.001, p. 88-96.

(56) References Cited

OTHER PUBLICATIONS

Jillette, et al., "Split Selectable Markers", Nature Communications, Oct. 31, 2019, doi:10.1038/s41467-019-12891-2, p. 1-8.
Pavankumar, "Inteins: Localized Distribution, Gene Regulation, and Protein Engineering for Biological Applications", Microorganisms, Feb. 28, 2018, doi:10.3390/microorganisms6010019, p. 1-15.
Choi, et al., "Precise genomic deletions using paired prime editing", bioRxiv, Jan. 2, 2021, doi:10.1101/2020.12.30.424891, p. 1-32.
Lin, et al., "High-efficiency prime editing with optimized, paired pegRNAs in plants", Nature Biotechnology, Mar. 25, 2021, doi:10.1038/s41587-021-00868-w, p. 1-12.
Bolukbasi, et al., "Orthogonal Cas9-Cas9 chimeras provide a versatile platform for genome editing", Nature Communications, Nov. 19, 2018, doi:10.1038/s41467-018-07310-x, p. 1-12.
Kweon, et al., "Fusion guide RNAs for orthogonal gene manipulation with Cas9 and Cpf1", Nature Communications, Nov. 23, 2017, doi:10.1038/s41467-017-01650-w, p. 1-6.
International Search Report and Written Opinion for International Application No. PCT/US21/48578, dated Feb. 15, 2022, p. 1-12.
International Search Report and Written Opinion for International Application No. PCT/US21/61156, dated Mar. 3, 2022, p. 1-13.
International Search Report and Written Opinion for International Application No. PCT/US20/53873, dated Jan. 14, 2021, p. 1-16.
Bao, et al., "Genome-scale engineering of *Saccharomyces cerevisiae* with single-nucleotide precision", Nature Biotechnology, doi:10.1038/nbt.4132, pp. 1-6 (May 7, 2018).
Dicarlo, et al., "Genome engineering in *Saccharomyces cervisiae* using CRISPR-Case systems", Nucleic Acids Research, 41(7):4336-43 (2013).
Garst, et al., "Genome-wide mapping of mutations at single-nucleotide resolution for protein, metabolic and genome engineering", Nature Biotechnology, 35(1):48-59 (2017).
Hsu, et al., "DNA targeting specificity of RNA-guided Cas9 nucleases", Nature Biotechnology, 31(9):827-32 (2013).
Jiang, et al., "RNA-guided editing of bacterial genomes using CRISPR-Cas systems", Nature Biotechnology, 31(3):233-41 (2013).
Jinek, et al., "A Programmable Dual-RNA-Guided DNA Endonuclease in Adaptive Bacterial Immunity", Science, 337:816-20 (2012).
Verwaal, et al., "CRISPR/Cpf1 enables fast and simple genome editing of *Saccharamyces cerevisiae*", Yeast, 35:201-11 (2018).
Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).
Roy, et cl., "Multiplexed precision genome editing with trackable genomic barcodes in yeast", Nature Biotechnolgy, doi:10.1038/nbt.4137, pp. 1-16 (2018).
Dong, "Establishment of a highly efficient virus-inducible CRISPR/Cas9 system in insect cells," Antiviral Res., 130:50-7(2016).
Epinat et al., "A novel engineered meganuclease induces homologous recombination in eukaryotic cells, e.g., yeast and mammalian cells", Nucleic Acids Research, 31(11): 2952-2962.
Farasat et al., "A Biophysical Model of CRISPR/Cas9 Activity for Rational Design of Genome Editing and Gene Regulation," PLoS Comput Biol., 29:12(1):e1004724 (2016).
Liu et al., "A chemical-inducible CRISPR-Cas9 system for rapid control of genome editing", Nature Chemical Biology, 12:980-987(2016).
Eklund, et al., "Altered target site specificity variants of the I-Ppol His-Cys bis homing endonuclease" Nucleic Acids Research, 35(17):5839-50 (2007).
Boles, et al., "Digital-to-biological converter for on-demand production of biologies", Nature Biotechnology, doi:10.1038/nbt.3859 (May 29, 2017).
Pines, et al., "Codon Compression Algorithms for Saturation Mutagenesis", ACS Synthetic Biology, 4:604-14 (2015).
Bessa et al., "Improved gap repair cloning in yeast: treatment of the gapped vector with Taq DNA polymerase avoids vector self-ligation," Yeast, 29(10):419-23 (2012).
Boch, "TALEs of genome targeting," Nature Biotechnology vol. 29, pp. 135-136 (2011).
Campbell et al., "Targeting protein function: the expanding toolkit for conditional disruption," Biochem J., 473(17):2573-2589 (2016).
Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).
Durai et al., "Zinc finger nucleases: custom-designed molecular scissors for genome engineering of plant and mammalian cells", Nucleic Acids Res., 33(18):5978-90 (2005).
Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20(1): 81-9 (2009).
Miller et al., "A TALE nuclease architecture for efficient genome editing", Nature Biotechnology, 29 (2): 143-8 (2011).
Mittelman et al., "Zinc-finger directed double-strand breaks within CAG repeat tracts promote repeat instability in human cells", PNAS USA, 106 (24): 9607-12 (2009).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
International Search Report and Written Opinion for International Application No. PCT/US2018/053608, dated Dec. 13, 2018, p. 1-9.
International Search Report and Written Opinion for International Application No. PCT/US2018/053670, dated Jan. 3, 2019, p. 1-13.
International Search Report and Written Opinion for International Application No. PCT/US2018/053671, dated Sep. 26, 2018, p. 1-12.
International Search Report and Written Opinion for International Application No. PCT/US2018/040519, dated Sep. 26, 2018, p. 1-8.
International Search Report and Written Opinion for International Application No. PCT/US2019/026836, dated Jul. 2, 2019, p. 1-10.
International Search Report and Written Opinion for International Application No. PCT/US2019/023342, dated Jun. 6, 2019, p. 1-34.
International Search Report and Written Opinion for International Application No. PCT/US2019/030085, dated Jul. 23, 2019, p. 1-14.
International Search Report and Written Opinion for International Application No. PCT/US20/24341, dated Jun. 19, 2020, p. 1-9.
NonFinal Office Action for U.S. Appl. No. 16/399,988, dated Jul. 31, 2019, p. 1-20.
First Office Action Interview Pilot Program Pre-Interview Communication for U.S. Appl. No. 16/024,831, dated Feb. 12, 2019, p. 1-37.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication Preinterview for U.S. Appl. No. 16/454,865 dated Aug. 16, 2019, p. 1-36.
Yoshioka, et al., "Development of a mono-promoter-driven CRISPR/Cas9 system in mammalian cells", Scientific Reports, Jul. 3, 2015, p. 1-8.
Remaut, et al., "Plasmid vectors for high-efficiency expression controlled by the PL promoter of coliphage lambda," Laboratory of Molecular Biology, Apr. 15, 1981, p. 81-93.
International Search Report and Written Opinion for International Application No. PCT/US2019/028821, dated Aug. 2, 2019, p. 1-14.
International Search Report and Written Opinion for International Application No. PCT/US2019/028883, dated Aug. 16, 2019, p. 1-12.
International Search Report and Written Opinion for International Application No. PCT/US2019/46526, dated Dec. 18, 2019, p. 1-17.
International Search Report and Written Opinion for International Application No. PCT/US2018/34779, dated Nov. 26, 2018, p. 1-39.

(56) References Cited

OTHER PUBLICATIONS

International Search Report and Written Opinion for International Application No. PCT/US19/57250, dated Feb. 25, 2020, p. 1-16.
International Search Report and Written Opinion for International Application No. PCT/US19/47135, dated Jun. 11, 2020, p. 1-15.

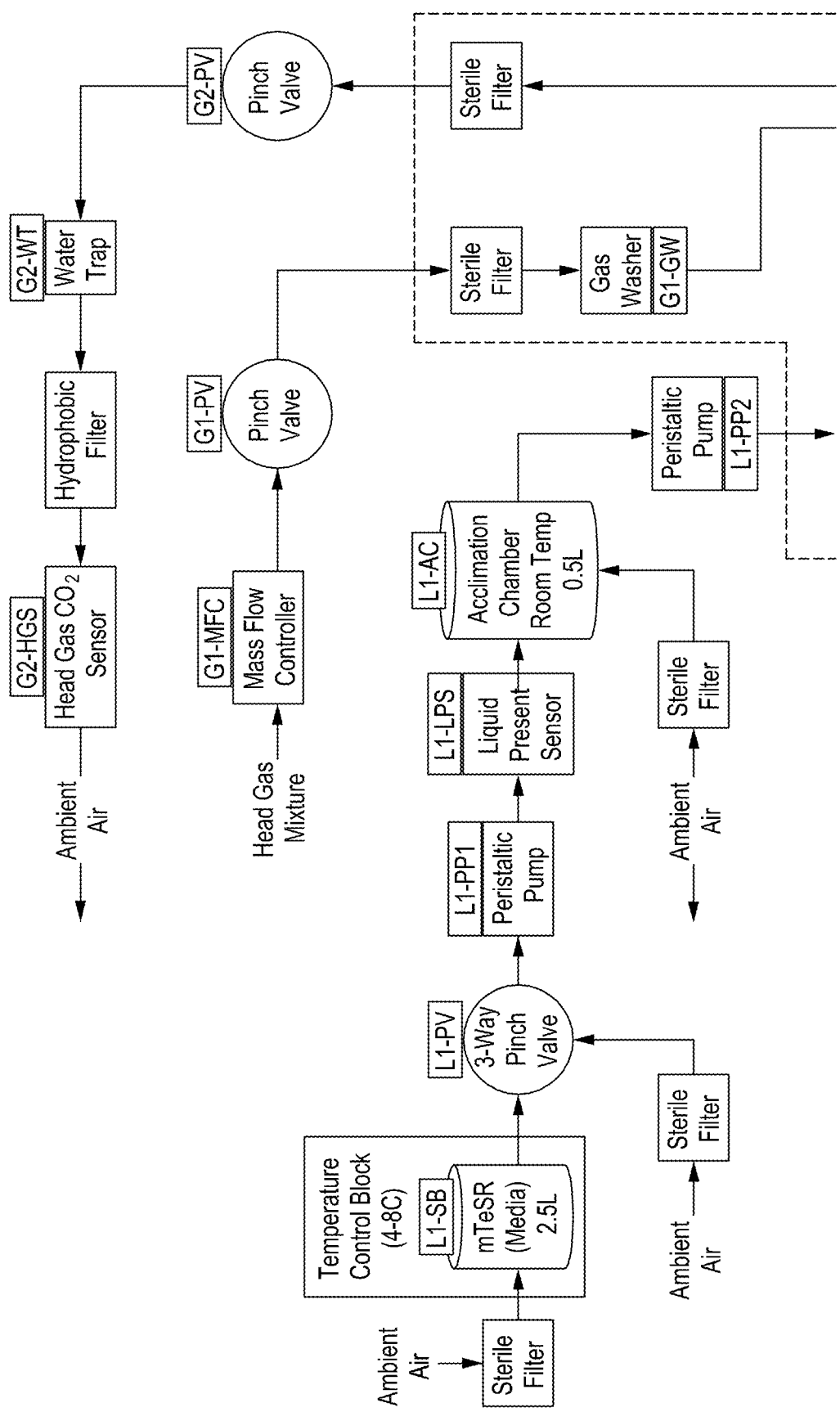

COMPOSITIONS, METHODS, MODULES AND INSTRUMENTS FOR AUTOMATED NUCLEIC ACID-GUIDED NUCLEASE EDITING IN MAMMALIAN CELLS VIA VIRAL DELIVERY

RELATED CASES

This application is a continuation of U.S. Ser. No. 17/239,538, filed 23 Apr. 2021, now allowed; which claims priority to U.S. Ser. No. 63/092,499 filed 15 Oct. 2020, entitled "Compositions, Methods, Modules and Instruments for Automated Nucleic Acid-Guided Nuclease Editing in Mammalian Cells" and U.S. Ser. No. 63/014,944, filed 24 Apr. 2020, also entitled "Compositions, Methods, Modules and Instruments for Automated Nucleic Acid-Guided Nuclease Editing in Mammalian Cells", all of which are incorporated herein by reference.

FIELD OF THE INVENTION

This invention relates to compositions of matter, methods, modules and instruments for automated mammalian cell growth and mammalian cell transduction followed by nucleic acid-guided nuclease editing in live mammalian cells via viral transduction.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the methods referenced herein do not constitute prior art under the applicable statutory provisions.

The ability to make precise, targeted changes to the genome of living cells has been a long-standing goal in biomedical research and development. Recently various nucleases have been identified that allow manipulation of gene sequence; hence, gene function. The nucleases include nucleic acid-guided nucleases, which enable researchers to generate permanent edits in live cells. Editing efficiencies frequently correlate with the concentration of guide RNAs (gRNAs) and repair templates (e.g., donor DNAs or homology arms) in the cell, particularly in mammalian cells, which may be achieved by delivering by transduction the guide RNAs and repair templates. Further, it is desirable to be able to perform many different edits in a population if mammalian cells simultaneously and to do so in an automated fashion, minimizing manual or hands-on cell manipulation.

There is thus a need in the art of nucleic acid-guided nuclease gene editing for improved compositions, methods, modules and automated instrumentation for increasing nucleic acid-guided nuclease editing efficiency and throughput in live mammalian cells, particularly in an end-to-end closed system. The present invention satisfies this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure relates to compositions, methods, modules and instrumentation for making edits in a mammalian genome. Efficient editing requires reliably providing copies of editing cassettes—comprising a gRNA and a repair template (e.g., donor DNA) or an integrated copy of one or more editing cassettes—in the cell nucleus. In order to perform highly-multiplexed editing in a single reaction, it is necessary to expose the cells to copies of an editing cassette, e.g., by transducing the cells with an editing cassette and allowing transcription thereof. Thus, the present compositions and methods entail viral delivery of an editing cassette to live mammalian cells such that the editing cassettes edit the cells and the edited cells continue to grow. In addition, it is preferably to use a fully-automated end-to-end instrument to process the cells without human intervention to enhance cell processing uniformity and to maintain the integrity of the cell culture.

Thus, in one embodiment there is provided a method of transducing, transfecting, and performing nucleic acid-guided nuclease editing in mammalian cells in an automated closed editing instrument comprising the steps of: providing an automated closed cell editing instrument comprising a growth module and a liquid handling system; transferring cell growth medium, first microcarriers and mammalian cells to the growth module via the liquid handling system; growing the mammalian cells on first microcarriers in the growth module; synthesizing and amplifying a library of editing cassettes off-instrument, wherein each editing cassette comprises a different gRNA and donor DNA pair; inserting editing cassettes into a viral backbone and producing viral particles off-instrument; delivering the viral particles to the mammalian cells in the growth module at a multiplicity of infection (MOI) such that each mammalian cell receives one cell or no cell; providing conditions to allow the viral vector to integrate into the mammalian cell DNA; enriching for cells with an integrated viral vector; delivering a nucleic acid-guided nuclease or nuclease fusion or a coding sequence for a nucleic acid-guided nuclease or nuclease fusion synthesized off-instrument to the enriched mammalian cells in the growth module via the liquid handling system; and providing conditions to allow editing to take place in the mammalian cells.

In some aspects of this embodiment, the microcarriers are fabricated from natural organic materials, biocompatible synthetic polymers, or inorganic materials, and in some aspects the microcarriers are fabricated from polystyrene or from a polyacrylate. In some aspects, the microcarriers are coated with laminin and in some aspects, the microcarriers are coated with laminin L-521. In some aspects of this embodiment, the microcarriers range in size from 30-1200 microns in diameter, and in some aspects, the microcarriers range in size from 50-150 microns in diameter.

In some aspects of this embodiment, between the enriching and second delivering step, the mammalian cells are detached from the microcarriers, the medium is exchanged and fresh microcarriers are added to the growth module. In some aspects, the growth module is a rotating growth module and the mammalian cells are detached from the microcarriers by increasing rotation of the rotating growth vial, and in some aspects the rotating growth module comprises fins, wherein the fins comprise frits. In other aspects, the growth module is a tangential flow filtration module and the mammalian cells are detached from the microcarriers by bubbling, or the growth module is a tangential flow filtration module and the mammalian cells are detached from the microcarriers by passing the mammalian cells through a conduit between reservoirs, wherein the conduit comprises at least one frit. In yet other aspects, the growth module is a bioreactor with at least one impeller and the mammalian cells are detached from the microcarriers by increasing revolutions per minute of the at least one impeller, and in some aspects, the growth module is a bioreactor with at least two impellers and the mammalian cells are detached from the microcarriers by increasing revolutions per minute of the at least two impellers.

Other embodiments provide a method of transducing, transfecting, and performing nucleic acid-guided nuclease editing in mammalian cells in an automated closed editing instrument comprising the steps of: providing an automated closed cell editing instrument comprising a growth module and a liquid handling system; transferring cell growth medium and mammalian cells to the growth module via the liquid handling system; growing mammalian cells into aggregates in the growth module; passaging the mammalian cells into smaller aggregates when the aggregates exceed 50-300 microns in size; synthesizing and amplifying a library of editing cassettes off-instrument, wherein each editing cassette comprises a different gRNA and donor DNA pair; inserting editing cassettes into a viral backbone and producing viral particles off-instrument; delivering the viral particles to the mammalian cells in the growth module at a multiplicity of infection (MOI) such that each mammalian cell receives one cell or no cell; providing conditions to allow the viral vector to integrate into the mammalian cell DNA; enriching for mammalian cells with an integrated viral vector; delivering a nucleic acid-guided nuclease or nuclease fusion or a coding sequence for a nucleic acid-guided nuclease or nuclease fusion synthesized off-instrument to the enriched mammalian cells in the growth module via the liquid handling system; and providing conditions to allow editing to take place in the mammalian cells.

In some aspects of this embodiment, the growth module is a rotating growth module and the mammalian cell aggregates are broken up by increasing rotation of the rotating growth vial, and in some aspects the rotating growth module comprises fins, wherein the fins comprise frits. In other aspects, the growth module is a tangential flow filtration module and the mammalian cell aggregates are broken up by bubbling, or the growth module is a tangential flow filtration module and the mammalian cell aggregates are broken up by passing the mammalian cells through a conduit between reservoirs, wherein the conduit comprises at least one frit. In yet other aspects, the growth module is a bioreactor with at least one impeller and the mammalian cell aggregates are broken up by increasing revolutions per minute of the at least one impeller, and in some aspects, the growth module is a bioreactor with at least two impellers and the mammalian cell aggregates are broken up by increasing revolutions per minute of the at least two impellers.

Another embodiment provides a method of transducing, transfecting, and performing nucleic acid-guided nuclease editing in mammalian cells in an automated closed editing instrument comprising the steps of: providing an automated closed cell editing instrument comprising a growth module and a liquid handling system; transferring ACCELLTA™ cell growth medium and mammalian cells to the growth module via the liquid handling system; growing mammalian cells in the ACCELLTA™ medium in the growth module; synthesizing and amplifying a library of editing cassettes off-instrument, wherein each editing cassette comprises a different gRNA and donor DNA pair; inserting editing cassettes into a viral backbone and producing viral particles off-instrument; delivering the viral particles to the mammalian cells in the growth module at a multiplicity of infection (MOI) such that each mammalian cell receives one cell or no cell; providing conditions to allow the viral vector to integrate into the mammalian cell DNA; enriching for mammalian cells with an integrated viral vector; delivering a nucleic acid-guided nuclease or nuclease fusion or a coding sequence for a nucleic acid-guided nuclease or nuclease fusion synthesized off-instrument to the enriched mammalian cells in the growth module via the liquid handling system; and providing conditions to allow editing to take place in the mammalian cells.

In all embodiments—cell growth on microcarriers, cell growth in aggregates, or cell growth in specialized medium—the growth module may be a rotating growth module, a tangential flow filtration module, or a bioreactor. In other aspects of these embodiments, the liquid handling system comprises an air displacement pipettor, and in this aspect, the automated closed cell editing instrument comprises a reagent cartridge. In alternative aspects, the liquid handing system comprises a manifold with one or more connections to the bioreactor or the liquid handling system comprises reagent receptacles individually connected to the growth module.

In some aspects of these embodiments, the mammalian cells are iPSCs, and in other aspects, the mammalian cells are primary cells, including NK and T cells.

In some aspects of these embodiments, viral vector is a lentiviral vector, an adeno-associated virus vector or an oncoretrovirus vector. In some aspects, the viral vector is delivered to the cells on microcarriers at an MOI of <0.05-1.0, or the viral vector is delivered to the cells on microcarriers at an MOI of <0.1-0.5, or the viral vector is delivered to the cells on microcarriers at an MOI of <0.1-0.3.

In yet another embodiment there is provided a method of growing cells, passaging the cells, editing the cells via nucleic acid-guided nuclease editing, and detaching the cells in a bioreactor, comprising the steps of: providing a bioreactor comprising: a growth vessel comprising a tapered main body, a lid assembly comprising ports, at least one driving impeller, and an impeller shaft, wherein there is at least one liquid-in port; at least one liquid-out port; at least one gas-in port; at least one gas-out port; at least one rupture disc; and at least one sensor port; and wherein the lid assembly makes an air-tight fitting on the tapered main body; and a bioreactor stand assembly comprising a frame, a stand main body disposed in the frame, wherein the stand main body accommodates the tapered main body of the growth vessel during operation, and wherein the stand main body comprises a heating element to heat the tapered main body; providing cell growth medium, cells, and first microcarriers to the tapered main body; allowing the cells to attach to the first microcarriers; providing a viral vector to the tapered main body of the growth vessel, wherein each viral vector comprises an editing cassette and a selection a selection marker, and wherein the viral vector is provided at a multiplicity of infection of less than one; allowing the viral vectors to transduce the cells on the first microcarriers; monitoring growth of the cells on the first microcarriers; selecting for transfected cells via the selection marker; detaching the cells from the first microcarriers by increasing revolutions per minute of the at least one impeller; stopping or slowing the at least one impeller; allowing the first microcarriers to settle in the tapered main body of the growth vessel; removing the first microcarriers from the tapered main body of the growth vessel or transferring the detached cells to a second main tapered body in a second growth vessel in the bioreactor; adding reagent bundle microcarriers to the tapered main body of the growth vessel, wherein the reagent bundle microcarriers comprise a lipofection agent and a nuclease; allowing the cells to attach to and grow on the reagent bundle microcarriers; providing conditions for the nuclease to transfect the cells; monitoring growth of the cells on the reagent bundle microcarriers; detaching the cells from the reagent bundle microcarriers by increasing revolutions per minute of the impeller; stopping or slowing the impeller; allowing the reagent bundle microcarriers to settle in the tapered main body of the growth vessel; removing the detached cells to a separate vessel.

In some aspects of either of these embodiments, the lid assembly further comprises a motor integration port for a motor to control the impeller, and in some aspects the bioreactor comprises a second impeller.

In some aspects of either of these embodiments, the at least one sensor port in the lid assembly is configured to accommodate a monitor capacitance of the cells and medium in the tapered main body of the growth vessel; a sensor to measure $O_2$ concentration of the cells and medium in the tapered main body of the growth vessel; a sensor to measure $CO_2$ of the cells and medium in the tapered main body of the growth vessel; a sensor to measure pH of the cells and medium in the tapered main body of the growth vessel; a sensor to measure lactate concentration of the cells and medium in the tapered main body of the growth vessel; a sensor to measure glucose concentration of the cells and medium in the tapered main body of the growth vessel; a sensor to measure biomass of the cells and medium in the tapered main body of the growth vessel; or a sensor to measure optical density of the cells and medium in the tapered main body of the growth vessel, and in some embodiments, there are at least two, at least three or at least four sensor ports in the lid assembly each configured to monitor capacitance of the cells and medium in the tapered main body of the growth vessel; a sensor to measure $O_2$ concentration of the cells and medium in the tapered main body of the growth vessel; a sensor to measure $CO_2$ of the cells and medium in the tapered main body of the growth vessel; a sensor to measure pH of the cells and medium in the tapered main body of the growth vessel; a sensor to measure lactate concentration of the cells and medium in the tapered main body of the growth vessel; a sensor to measure glucose concentration of the cells and medium in the tapered main body of the growth vessel; a sensor to measure biomass of the cells and medium in the tapered main body of the growth vessel; or a sensor to measure optical density of the cells and medium in the tapered main body of the growth vessel.

In some aspects of either of these embodiments, the lid assembly further comprises a temperature probe, and in some aspects the lid assembly further comprises a camera port. In some aspects the heating element of the stand main body is a heat jacket, and in some aspects, the heat jacket comprises LED lights and may also comprise a camera port. In some aspects the at least one liquid-out port comprises a filter. In some aspects there is more than one liquid-out port and/or more than one liquid-in port.

In some aspects of either of these embodiments, the tapered main body of the growth vessel accommodates cell culture volumes of 25 ml to 500 ml. In some aspects, during cell growth impeller revolutions per minute is approximately 40-80 rpm, and in some aspects during cell detachment impeller revolutions per minute is approximately 2700 rpm. In some aspects of either of these embodiments, the tapered main body is optically transparent and in some aspects, the tapered main body is optically transparent in UV and IR ranges.

In some aspects of these embodiments, a chemical agent is added to the tapered main body of the growth vessel to aid in detaching the cells, and in some aspects, the chemical agent is hemagglutinin, collagenase, dispase or trypsin.

In some aspects of these embodiments, the nuclease is provided as a protein and in other aspects, the nuclease is provided as a nucleic acid coding sequence under control of a promoter.

These aspects and other features and advantages of the invention are described below in more detail.

BRIEF DESCRIPTION OF THE DRAWINGS

The foregoing and other features and advantages of the present invention will be more fully understood from the following detailed description of illustrative embodiments taken in conjunction with the accompanying drawings in which:

FIGS. 5H-1 and 5H-2 depict an exemplary fluidic diagram for the bioreactor described in relation to FIGS. 5A-5G.

FIG. 17 at bottom left is a bar graph showing a stemness panel (FACS % positive) for cells in the bioreactor described herein, on laminin plates and on MATRIGEL® plates (CORNING® BIOCOAT™ MATRIGEL® 6-well plates (Corning, Inc., Glendale Ariz.)). FIG. 17 at bottom right is a bar graph showing a stemness panel (FACS median fluorescence) for cells in the bioreactor described herein, on laminin plates and on MATRIGEL® plates (CORNING® BIOCOAT™ MATRIGEL® 6-well plates (Corning, Inc., Glendale Ariz.)).

It should be understood that the drawings are not necessarily to scale, and that like reference numbers refer to like features.

DETAILED DESCRIPTION

Figure 1:
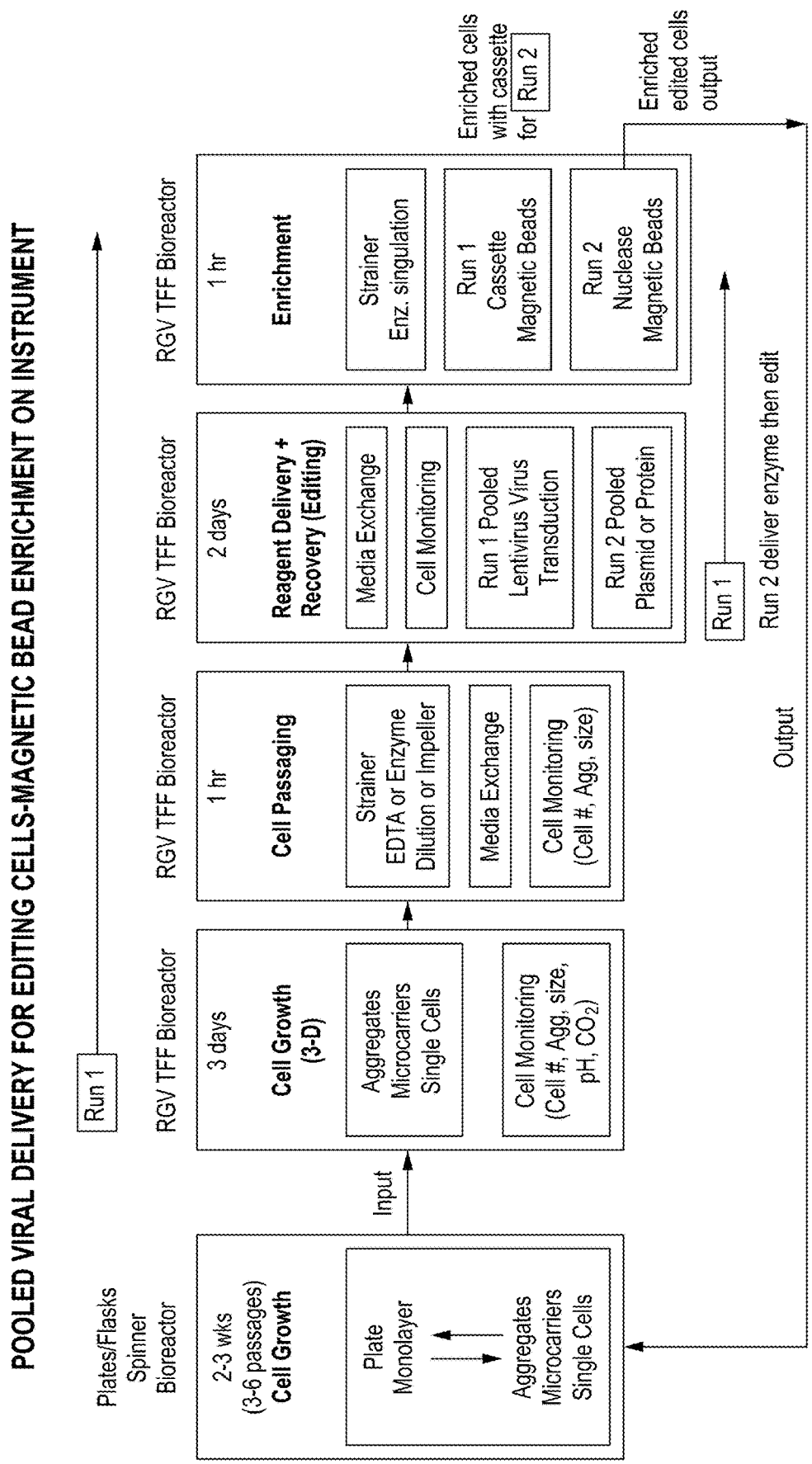
FIG. 1 depicts an exemplary workflow employing pooled viral delivery of nucleic acids to mammalian cells grown in suspension in an automated instrument followed by magnetic enrichment of edited cells.

All of the functionalities described in connection with one embodiment are intended to be applicable to the additional embodiments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, biochemistry and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W. H. Freeman, New York N.Y.; Gait, "*Oligonucleotide Synthesis: A Practical Approach*" 1984, IRL Press, London; Nelson and Cox (2000), Lehninger, *Principles of Biochemistry* $3^{rd}$ Ed., W. H. Freeman Pub., New York, N.Y.; *Viral Vectors* (Kaplift & Loewy, eds., Academic Press 1995); all of which are herein incorporated in their entirety by reference for all purposes. For mammalian/stem cell culture and methods see, e.g., *Basic Cell Culture Protocols*, Fourth Ed. (Helgason & Miller, eds., Humana Press 2005); *Culture of Animal Cells*, Seventh Ed. (Freshney, ed., Humana Press 2016); *Microfluidic Cell Culture*, Second Ed. (Borenstein, Vandon, Tao & Charest, eds., Elsevier Press 2018); *Human Cell Culture* (Hughes, ed., Humana Press 2011); *3D Cell Culture* (Koledova, ed., Humana Press 2017); *Cell and Tissue Culture: Laboratory Procedures in Biotechnology* (Doyle & Griffiths, eds., John Wiley & Sons 1998); *Essential Stem Cell Methods*, (Lanza & Klimanskaya, eds., Academic Press 2011); *Stem Cell Therapies: Opportunities for Ensuring the Quality and Safety of Clinical Offerings: Summary of a Joint Workshop* (Board on Health Sciences Policy, National Academies Press 2014); *Essentials of Stem Cell Biology*, Third Ed., (Lanza & Atala, eds., Academic Press 2013); and *Handbook of Stem Cells*, (Atala & Lanza, eds., Academic Press 2012). For background on viral transduction see, e.g., Horwath, et al., Using Viral Vectors as Gene Transfer Tools, Cell Biol. Toxicol., 26(1):1-20 (2010); Principles of Molecular Virology, $6^{th}$ Ed, A. Cann, ed., Academic Press (2000); *Molecular Cell Biology*, $4^{th}$ Ed., Lodish, et al., eds., Section 6.3, W H Freeman (2000); and *Viral Vectors for Gene Therapy*, Merton, et al., eds., Springer Press (2010). CRISPR-specific techniques can be found in, e.g., *Genome Editing and Engineering from TALENs and CRISPRs to Molecular Surgery*, Appasani and Church (2018); and *CRISPR: Methods and Protocols*, Lindgren and Charpentier (2015); which is incorporated herein in its entirety by reference for all purposes.

Note that as used herein and in the appended claims, the singular forms "a," "an," and "the" include plural referents unless the context clearly dictates otherwise. Thus, for example, reference to "an oligonucleotide" refers to one or more oligonucleotides, and reference to "an automated system" includes reference to equivalent steps and methods for use with the system known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, methods and cell populations that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of ordinary skill in the art that the present invention may be practiced without one or more of these specific details. In other instances, features and procedures well known to those skilled in the art have not been described in order to avoid obscuring the invention.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TAGCTG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

As used herein the term "donor DNA" or "donor nucleic acid" or "homology arm" or "repair arm" refers to nucleic acid that is designed to introduce a DNA sequence modification (insertion, deletion, substitution) into a locus by homologous recombination using nucleic acid-guided nucleases or a nucleic acid that serves as a template (including a desired edit) to be incorporated into target DNA by reverse transcriptase in a CREATE fusion editing (CFE) system. For homology-directed repair, the donor DNA must have sufficient homology to the regions flanking the "cut site" or the site to be edited in the genomic target sequence. The length of the homology arm(s) will depend on, e.g., the type and size of the modification being made. In many instances and preferably, the donor DNA will have two regions of sequence homology (e.g., two homology arms) to the genomic target locus. Preferably, an "insert" region or "DNA sequence modification" region—the nucleic acid modification that one desires to be introduced into a genome target locus in a cell-will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the target sequence.

The terms "editing cassette", "CREATE cassette", "CREATE editing cassette", or "CREATE fusion cassette" refers to a nucleic acid molecule comprising a coding sequence for transcription of a guide nucleic acid or gRNA covalently linked to a coding sequence for transcription of a donor DNA or homology arm.

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease.

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Nucleic acid-guided editing components" refers to one, some, or all of a nucleic acid-guided nuclease or nickase fusion enzyme, a guide nucleic acid and a donor nucleic acid.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e., chromosome) and may still have interactions resulting in altered regulation.

A "PAM mutation" refers to one or more edits to a target sequence that removes, mutates, or otherwise renders inactive a PAM or spacer region in the target sequence.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA. Promoters may be constitutive or inducible.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, chloramphenicol, nourseothricin N-acetyl transferase, erythromycin, tetracycline, gentamicin, bleomycin, streptomycin, puromycin, hygromycin, blasticidin, and G418 may be employed. In other embodiments, selectable markers include, but are not limited to human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA 1; conjugates glutathione to the stem cell selective alkylator busulfan; chemoprotective selectable marker in CD34+cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2a; detectable by Mab-FITC); Methylguanine-DNA methyltransferase (MGMT; selectable by carmustine); rhamnose; and Cytidine deaminase (CD; selectable by Ara-C). "Selective medium" as used herein refers to cell growth medium to which has been added a chemical compound or biological moiety that selects for or against selectable markers.

The terms "target genomic DNA sequence", "target sequence", or "genomic target locus" refer to any locus in vitro or in vivo, or in a nucleic acid (e.g., genome or episome) of a cell or population of cells, in which a change of at least one nucleotide is desired using a nucleic acid-guided nuclease editing system. The target sequence can be a genomic locus or extrachromosomal locus.

The terms "transformation", "transfection" and "transduction" are used interchangeably herein to refer to the process of introducing exogenous DNA into cells.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, BACs, YACs, PACs, synthetic chromosomes, and the like. In some embodiments, a coding sequence for a nucleic acid-guided nuclease is provided in a vector, referred to as an "engine vector." In some embodiments, the editing cassette may be provided in a vector, referred to as an "editing vector." In some embodiments, the coding sequence for the nucleic acid-guided nuclease and the editing cassette are provided in the same vector.

Nuclease-Directed Genome Editing Generally

The compositions, methods, modules and automated instruments described herein are employed to allow one to perform nucleic acid nuclease-directed genome editing to introduce desired edits to a population of live mammalian cells. The compositions and methods entail viral delivery of, on average, a single copy of an editing cassette to each live mammalian cell to effect editing of the genome of the mammalian cells by transcription of the editing cassettes. In some embodiments, the editing cassettes are integrated into the genome of the mammalian cells. Transduction of the editing cassette is then followed by transfection of a nucleic acid coding for a nucleic acid-guided nuclease or nuclease fusion or the nucleic acid-guided nuclease or nuclease fusion itself.

Generally, a nucleic acid-guided nuclease or nickase fusion complexed with an appropriate synthetic guide nucleic acid in a cell can cut the genome of the live cell at a desired location. The guide nucleic acid helps the nucleic acid-guided nuclease or nickase fusion recognize and cut the DNA at a specific target sequence. By manipulating the nucleotide sequence of the guide nucleic acid, the nucleic acid-guided nuclease or nickase fusion may be programmed to target any DNA sequence for cleavage as long as an appropriate protospacer adjacent motif (PAM) is nearby. In certain aspects, the nucleic acid-guided nuclease or nickase fusion editing system may use two separate guide nucleic acid molecules that combine to function as a guide nucleic acid, e.g., a CRISPR RNA (crRNA) and trans-activating CRISPR RNA (tracrRNA). In other aspects and preferably, the guide nucleic acid is a single guide nucleic acid construct that includes both 1) a guide sequence capable of hybridizing to a genomic target locus, and 2) a scaffold sequence capable of interacting or complexing with a nucleic acid-guided nuclease or nickase fusion.

In general, a guide nucleic acid (e.g., gRNA) complexes with a compatible nucleic acid-guided nuclease or nickase fusion and can then hybridize with a target sequence, thereby directing the nuclease or nickase fusion to the target sequence. A guide nucleic acid can be DNA or RNA; alternatively, a guide nucleic acid may comprise both DNA and RNA. In some embodiments, a guide nucleic acid may comprise modified or non-naturally occurring nucleotides. Preferably and typically, the guide nucleic acid comprises RNA and the gRNA is encoded by a DNA sequence on an editing cassette along with the coding sequence for a donor DNA (e.g., whether a donor DNA to recombine with the target or a donor DNA to be reverse transcribed into the target region). Covalently linking the gRNA and donor DNA allows one to scale up the number of edits that can be made in a population of cells tremendously. Methods and compositions for designing and synthesizing editing cassettes (e.g., CREATE cassettes) are described in, e.g., U.S. Pat. Nos. 9,982,278; 10,266,849; 10,240,167; 10,351,877; 10,364,442; 10,435,715; 10,465,207; 10,669,559; 10,711,284; and 10,713,180 and U.S. Ser. Nos. 16/550,092 and 16/938,739, all of which are incorporated by reference herein. Alternatively, the nuclease or nickase fusion enzyme and gRNAs may be introduced into the cells as ribonuclease/protein complexes (RNPs), with the donor DNA introduced as an oligonucleotide or sequence to be transcribed from a vector. The donor DNA most often is introduced simultaneously with the RNPs, but may also be introduced separately from the RNPs.

A guide nucleic acid comprises a guide or spacer sequence, where the guide sequence is a polynucleotide sequence having sufficient complementarity with a target sequence to hybridize with the target sequence and direct sequence-specific binding of a complexed nucleic acid-guided nuclease or nickase fusion to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In general, to generate an edit in the target sequence, the gRNA/nuclease or gRNA/nickase fusion complex binds to a target sequence as determined by the guide RNA, and the nuclease or nickase fusion recognizes a protospacer adjacent motif (PAM) sequence adjacent to the target sequence. The target sequence can be any polynucleotide endogenous or exogenous to the cell, or in vitro. For example, in the case of mammalian cells the target sequence is typically a polynucleotide residing in the nucleus of the cell. A target sequence can be a sequence encoding a gene product (e.g., a protein) or a non-coding sequence (e.g., a regulatory polynucleotide, an intron, a PAM, a control sequence, or "junk" DNA). The proto-spacer mutation (PAM) is a short nucleotide sequence recognized by the gRNA/nuclease complex. The precise preferred PAM sequence and length requirements for different nucleic acid-guided nucleases or nickase fusions vary; however, PAMs typically are 2-10 base-pair sequences adjacent or in proximity to the target sequence and, depending on the nuclease or nickase, can be 5' or 3' to the target sequence.

In most embodiments, genome editing of a cellular target sequence both introduces a desired DNA change to a cellular target sequence, e.g., the genomic DNA of a cell, and removes, mutates, or renders inactive a proto-spacer mutation (PAM) region in the cellular target sequence (e.g., thereby rendering the target site immune to further nuclease binding). Rendering the PAM at the cellular target sequence inactive precludes additional editing of the cell genome at that cellular target sequence, e.g., upon subsequent exposure to a nucleic acid-guided nuclease or nickase fusion complexed with a synthetic guide nucleic acid in later rounds of editing. Thus, cells having the desired cellular target sequence edit and an altered PAM can be selected for by using a nucleic acid-guided nuclease or nickase fusion complexed with a synthetic guide nucleic acid complementary to the cellular target sequence. Cells that did not undergo the first editing event will be cut rendering a double-stranded DNA break, and thus will not continue to be viable. The cells containing the desired cellular target sequence edit and PAM alteration will not be cut, as these edited cells no longer contain the necessary PAM site and will continue to grow and propagate.

As for the nuclease or nickase fusion component of the nucleic acid-guided nuclease editing system, a polynucleotide sequence encoding the nucleic acid-guided nuclease or nickase fusion can be codon optimized for expression in particular cell types, such as bacterial, yeast, and, here, mammalian cells. The choice of the nucleic acid-guided nuclease or nickase fusion to be employed depends on many factors, such as what type of edit is to be made in the target sequence and whether an appropriate PAM is located close to the desired target sequence. Nucleases of use in the methods described herein include but are not limited to Cas 9, Cas 12/Cpf1, MAD2, or MAD7, MAD 2007 or other MADzymes (see U.S. Pat. Nos. 9,982,279; 10,337,028; 10,604,746; 10,665, 114; 10,640,754, 10,876,102; 10,883,077; 10,704,033; 10,745,678; 10,724,021; 10,767,169; and 10,870,761 for sequences and other details related to MADzymes). Nickase fusion enzymes typically comprise a CRISPR nucleic acid-guided nuclease engineered to cut one DNA strand in the target DNA rather than making a double-stranded cut, and the nickase portion is fused to a reverse transcriptase. For more information on nickases and nickase fusion editing see U.S. Pat. No. 10,689,669 and U.S. Ser. Nos. 16/740,418; 16/740,420 and 16/740,421, both filed 11 Jan. 2020. Here, a coding sequence for a desired nuclease or nickase fusion is typically on an "engine vector" along with other desired sequences such as a selective marker.

Another component of the nucleic acid-guided nuclease or nickase fusion system is the donor nucleic acid comprising homology to the cellular target sequence and an engineered change to the cellular target sequence. For the present compositions, methods, modules and instruments the donor nucleic acid typically is in the same editing cassette as (e.g., is covalently-linked to) the guide nucleic acid and is under the control of the same promoter as the gRNA (that is, a single promoter driving the transcription of both the editing gRNA and the donor nucleic acid). The donor nucleic acid is designed to serve as a template for homologous recombination with a cellular target sequence cleaved by the nucleic acid-guided nuclease or the donor DNA serves as a template to incorporate an edit into the target via reverse transcriptase fused to a nickase as a part of the gRNA/nuclease complex. A donor nucleic acid polynucleotide may be of any suitable length, such as about or more than about 20, 25, 50, 75, 100, 150, 200, 500, or 1000 nucleotides in length, and up to 2, 3, 4, 5, 6, 7, 8, 9, 10, 11, 12, 13 and up to 20 kb in length if combined with a dual gRNA architecture as described in U.S. Pat. No. 10,711,284.

In certain preferred aspects, the donor nucleic acid can be provided as an oligonucleotide of between 20-300 nucleotides, more preferably between 50-250 nucleotides. The donor nucleic acid comprises a region that is complementary to a portion of the cellular target sequence (e.g., a homology arm(s)). When optimally aligned, the donor nucleic acid overlaps with (is complementary to) the cellular target sequence by, e.g., about as few as 4 (in the case of nickase fusions) and as many as 20, 25, 30, 35, 40, 50, 60, 70, 80, 90 or more nucleotides (in the case of nucleases). The donor nucleic acid typically comprises two homology arms (regions complementary to the cellular target sequence) flanking the mutation or difference between the donor nucleic acid and the cellular target sequence, although in CREATE fusion embodiments, the edit may be located at one end of a single homology arm rather than positioned between two homology arms. The donor nucleic acid comprises at least one mutation or alteration compared to the cellular target sequence, such as an insertion, deletion, modification, or any combination thereof compared to the cellular target sequence.

As described in relation to the gRNA, the donor nucleic acid is provided as part of a rationally-designed editing cassette along with a promoter to drive transcription of both the gRNA and donor DNA. As described below, the editing cassette may be provided as a linear editing cassette, or the editing cassette may be inserted into an editing vector. Moreover, there may be more than one, e.g., two, three, four, or more editing gRNA/donor nucleic acid pair rationally-designed editing cassettes linked to one another in a linear "compound cassette" or inserted into an editing vector; alternatively, a single rationally-designed editing cassette may comprise two to several editing gRNA/donor DNA pairs, where each editing gRNA is under the control of separate different promoters, separate promoters, or where all gRNAs/donor nucleic acid pairs are under the control of a single promoter. In some embodiments the promoter driving transcription of the editing gRNA and the donor nucleic acid (or driving more than one editing gRNA/donor nucleic acid pair) is an inducible promoter. In many if not most embodiments of the compositions, methods, modules and instruments described herein, the editing cassettes make up a collection or library editing gRNAs and of donor nucleic acids representing, e.g., gene-wide, pathway-wide or genome-wide libraries of editing gRNAs and donor nucleic acids.

In addition to the donor nucleic acid, the editing cassettes comprise one or more primer binding sites to allow for PCR amplification of the editing cassettes. The primer binding sites are used to amplify the editing cassette by using oligonucleotide primers and may be biotinylated or otherwise labeled. In addition, the editing cassette may comprise a barcode. A barcode is a unique DNA sequence that corresponds to the donor DNA sequence such that the barcode serves as a proxy to identify the edit made to the corresponding cellular target sequence. The barcode typically comprises four or more nucleotides. Also, in preferred embodiments, an editing cassette or editing vector or engine vector further comprises one or more nuclear localization sequences (NLSs), such as about or more than about 1, 2, 3, 4, 5, 6, 7, 8, 9, 10, or more NLSs.

Mammalian Cell Growth, Transduction and Editing

The present compositions and methods are drawn to nucleic acid-guided nuclease editing of live mammalian cells. The methods involve viral delivery of a single or no editing cassette to cells in an automated system.

In the present methods, mammalian cells are often grown in culture off-instrument for several passages before entry into an automated process. Cell culture is the process by which cells are grown under controlled conditions, almost always outside the cell's natural environment. For mammalian cells, culture conditions typically vary somewhat for each cell type but generally include a medium and additives that supply essential nutrients such as amino acids, carbohydrates, vitamins, minerals, growth factors, hormones, and gases such as, e.g., $O_2$ and $CO_2$. In addition to providing nutrients, the medium typically regulates the physio-chemical environment via a pH buffer, and most cells are grown at 37° C. Many mammalian cells require or prefer a surface or artificial substrate on which to grow (e.g., adherent cells), whereas other cells such as hematopoietic cells and some adherent cells can be grown in or adapted to grow in suspension. Adherent cells often are grown in 2D monolayer cultures in petri dishes or flasks, but some adherent cells can grow in suspension cultures to higher density than would be possible in 2D cultures. "Passages" generally refers to transferring a small number of cells to a fresh substrate with fresh medium, or, in the case of suspension cultures, transferring a small volume of the culture to a larger volume of medium.

Mammalian cells include primary cells, which are cultured directly from a tissue and typically have a limited lifespan in culture, including T cells and NK cells; established or immortalized cell lines, which have acquired the ability to proliferate indefinitely either through random mutation or deliberate modification such as by expression of the telomerase gene; and stem cells, of which there are undifferentiated stem cells or partly-differentiated stem cells that can both differentiate into various types of cells and divide indefinitely to produce more of the same stem cells.

Primary cells can be isolated from virtually any tissue. Immortalized cell lines can be created or may be well-known, established cell lines such as human cell lines DU145 (derived from prostate cancer cells); H295R (derived from adrenocortical cancer cells); HeLa (derived from cervical cancer cells); KBM-7 (derived from chronic myelogenous leukemia cells); LNCaP (derived from prostate cancer cells); MCF-7 (derived from breast cancer cells); MDA-MB-468 (derived from breast cancer cells); PC3 (derived from prostate cancer cells); SaOS-2 (derived from bone cancer cells); SH-SY5Y (derived from neuroblastoma cells); T-047D (derived from breast cancer cells); TH-1 (derived from acute myeloid leukemia cells); U87 (derived from glioblastoma cells); and the National Cancer Institute's 60 cancer line panel NCI60; and other immortalized mammalian cell lines such as Vero cells (derived from African green monkey kidney epithelial cells); the mouse line MC3T3; rat lines GH3 (derived from pituitary tumor cells) and PC12 (derived from pheochromocytoma cells); and canine MDCK cells (derived from kidney epithelial cells).

Stem cells are of particular interest in the methods and compositions described herein. Generally speaking, there are three general types of mammalian stem cells: adult stem cells (ASCs), which are undifferentiated cells found living within specific differentiated tissues including hematopoietic, mesenchymal, neural, and epithelial stem cells; embryonic stem cells (ESCs), which in humans are isolated from a blastocyst typically 3-5 days following fertilization and which are capable of generating all the specialized tissues that make up the human body; and induced pluripotent stem cells (iPSCs), which are adult stem cells that are created using genetic reprogramming with, e.g., protein transcription factors.

Once the cells of choice have been grown and passaged several times—in most embodiments off-instrument—in a first step the mammalian cells that are to be edited are transferred to an automated instrument where the cells are grown in cell culture and the growth of the cells is monitored. Growth modules envisioned in the automated instrument include a rotating growth module, a tangential filtration module, and a bioreactor, all of which are described in detail infra. Moreover, these growth modules may be used for the transduction and transfection or reverse transfection steps performed prior to editing. Monitoring is usually performed by imaging the cells as described infra and/or by, e.g., measuring pH of the medium using a medium comprising a pH indicator. As opposed to 2D culture of cells as described above, the present methods envision culturing the cells in suspension. Growing cells in suspension can be effected in various configurations. Adherent cells that typically are grown in 2D cultures when grown in suspension often aggregate into "clumps." For example, some iPSCs grow well as aggregates in suspension, and are most healthy growing in aggregates of 50-300 microns in size, starting off as smaller aggregates 30-50 microns in size. iPSCs are typically grown in culture 3-5 days between passaging and the larger aggregates are broken into smaller aggregates by filtering them, e.g., through a cell strainer (e.g., a sieve or frit) with a 37 micron filter. The iPSCs can grow indefinitely in 3D aggregates as long as they are passaged into smaller aggregates when the aggregates become approximately 300-400 microns in size.

An alternative to growing cells in 3D aggregates and in a preferred embodiment is growing cells on microcarriers. Generally, microcarriers are nonporous (comprised of pore sizes range from 0-20 nm), microporous (comprised of pore sizes range from 20 nm-1 micron), and macroporous (comprised of pore sizes range from 1-50 microns) microcarriers comprising natural organic materials such as, e.g., gelatin, collagen, alginate, agarose, chitosan, and cellulose; biocompatible synthetic polymeric materials such as, e.g., polystyrene, polyacrylates such as polyacrylamide, polyamidoamine (PAMAM), polyethylene oxide (PEO/PEG), poly(N-isopropylacrylamide) (PNIPAM), polycaprolactone (PCL), polylactic acid (PLA), and polyglycolic acid (PGA); inorganic materials such as, e.g., silica, silicon, mica, quartz and silicone; as well as mixtures of natural, polymeric materials, cross-linked polymeric materials, and inorganic materials etc. on which animal cells can grow. Microcarriers useful in the methods herein typically range in size from 30-1200 microns in diameter and more typically range in size from 40-200 or from 50-150 microns in diameter. Microcarriers for cell culture are widely commercially available from, e.g., Millipore Sigma, (St. Louis, Mo., USA); Thermo Fisher (Waltham, Mass., USA); Pall Corp. (Port Washington, N.Y., USA); GE Life Sciences (Marlborough, Mass., USA); and Corning Life Sciences (Tewkesbury, Mass., USA). As for the extracellular matrix, natural matrices include collagen, fibrin and vitronectin (available, e.g., from ESBio, Alameda, Calif., USA), and synthetic matrices include MATRIGEL® (Corning Life Sciences, Tewkesbury, Mass., USA), GELTREX™ (Thermo Fisher Scientific, Waltham, Mass., USA), CULTREX® (Trevigen, Gaithersburg, Md., USA), biomemetic hydrogels available from Cellendes (Tubingen, Germany); and tissue-specific extracellular matrices available from Xylyx (Brooklyn, N.Y., USA); further, denovoMatrix (Dresden, Germany) offers screenMATRIX™, a tool that facilitates rapid testing of a large variety of cell microenvironments (e.g., extracellular matrices) for optimizing growth of the cells of interest.

Finally, another option for growing mammalian cells for editing in the compositions, methods, modules and automated instruments described herein is growing single cells in suspension using a specialized medium such as that developed by ACCELLTA™ (Haifa, Israel). Cells grown in this medium must be adapted to this process over many cell passages; however, once adapted the cells can be grown to a density of >40 million cells/ml and expanded 50-100× in approximately a week, depending on cell type.

There are three exemplary modules—as an alternative to classic culture in flasks or tissue culture plates—for growing and monitoring cells off-instrument or in the automated instruments described herein. One module is a rotating growth module, which is depicted in FIGS. 3A-3E, another module is a tangential flow filtration module, which is depicted in FIGS. 4A-4E and finally another module is a bioreactor, which is depicted in FIGS. 5A-5G. These modules can be adapted to dissociate cells (if required) as well, which process is described in detail in relation to these figures.

The cells grown off-instrument or in a growth module of the automated instrument as well as reagents needed for cell growth, nucleic acid amplification, cell transfection or transduction, cell editing and enrichment may be provided in a reagent cartridge. The cells and reagents are moved from the reagent cartridge and between modules by a robotic liquid handling system including the gantry. As an example, the robotic liquid handling system may include an automated liquid handling system such as those manufactured by Tecan Group Ltd. of Mannedorf, Switzerland, Hamilton Company of Reno, Nev. (see, e.g., WO2018015544A1 to Ott, entitled "Pipetting device, fluid processing system and method for operating a fluid processing system"), or Beckman Coulter, Inc. of Fort Collins, Colo. (see, e.g., US20160018427A1 to Striebl et al., entitled "Methods and systems for tube inspection and liquid level detection"), and typically includes an air displacement pipettor.

Reagent cartridges, such as those described in U.S. Pat. Nos. 10,376,889; 10,406,525; 10,478,222; 10,576,474; 10,639,637 and 10,738,271 allow for particularly easy integration with liquid handling instrumentation. In some embodiments, only the air displacement pipettor is moved by the gantry and the various modules and reagent cartridge remain stationary. In alternative embodiments, an automated mechanical motion system (actuator) additionally supplies XY axis motion control or XYZ axis motion control to one or more modules and/or cartridges of the automated multi-module cell processing system. Used pipette tips, for example, may be placed by the robotic handling system in a waste repository. For example, an active module may be raised to come into contact-accessible positioning with the robotic handling system or, conversely, lowered after use to avoid impact with the robotic handling system as the robotic handling system is moving materials to other modules within the automated multi-module cell processing instrument. Alternatively, the cells may be transferred to the growth module by the user.

Alternatively, in some embodiments, a gantry and/or an air displacement pump is not used; instead, in one embodiment reagents are individually connected to the bioreactor, typically via tubing or microfluidic circuits; in another embodiment, reagents may be connected to a manifold that has a single connection to the bioreactor. In some embodiments, the bioreactor is a completely closed fluidic system; that is, e.g., no pipets piercing reagent tubes and transferring liquid.

In addition, any of the growth modules described herein may reside in the same automated instrument; that is, one automated instrument may comprises two or more rotating growth modules, two or more tangential flow filtration modules and/or two or more bioreactors and/or combinations of these modules for processing cells in parallel.

In a next step, the cells that have been grown in suspension or on microcarriers are dissociated or, if grown on microcarriers, may be dissociated from the microcarrier and/or transferred to fresh microcarriers. Dissociation is required if the cells grown as cell aggregates. In one embodiment, dissociation may be via mechanical means such as agitation or by a filter, frit or sieve. Such a filter, frit or sieve may be adapted to be part of the rotating growth module, tangential flow filtration module, or bioreactor module as described in relation to FIGS. 3A-3E, 4A-4E, and 5A-5G or may be a separate "dissociation only module." As an alternative, aggregates of cells may be dissociated by enzymes such as hemagglutinin, collagenase, dispase and trypsin, which can be added to the medium of the growing cells in the rotating growth module, tangential flow filtration module or bioreactor. If the cells are grown on microcarriers, the cells can be dissociated from the microcarriers using enzymes that are typically used in cell culture to dissociate cells in 2D culture, such as collagenase, trypsin or pronase or by non-enzymatic methods including EDTA or other chelating chemicals. In a bioreactor, dissociation can be performed mechanically using, e.g., an impeller or by bubbling, or cells grown in a bioreactor may be transferred to a dissociation module. Example XI herein describes the results of cells having been detached in a bioreactor via turbulence created by an impeller.

Finally, in some methods and instruments, the population of cells after editing are enriched for edited cells by, e.g., magnetic beads, antibiotic selection, co-edit selection, or FACS sorting, all of which are described in more detail infra.

Viral Pooled Delivery for Editing Cells Grown in Suspension

Figure 2:
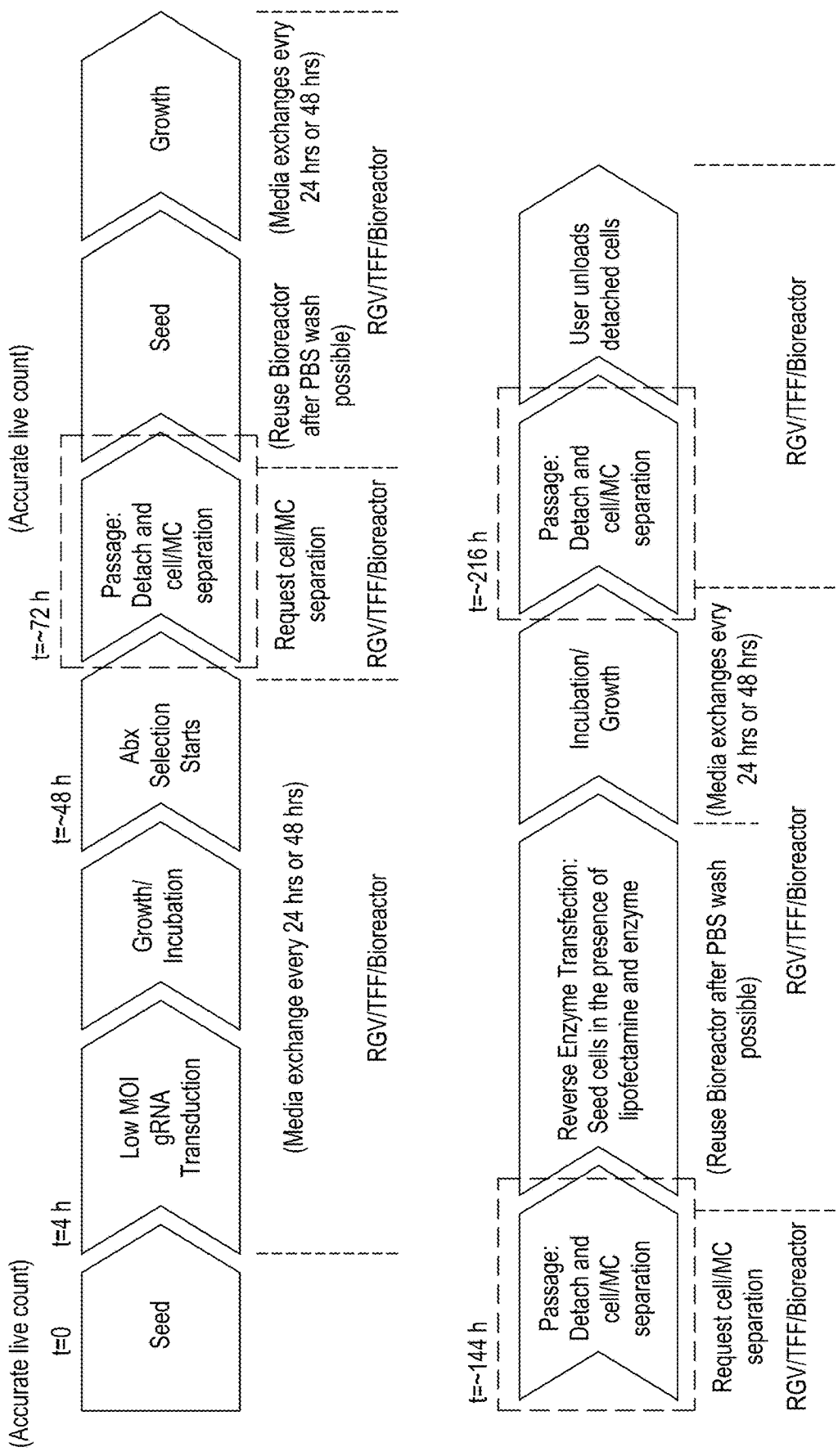
FIG. 2 also depicts an exemplary workflow employing pooled viral delivery of nucleic acids to mammalian cells grown in suspension in an automated instrument with additional details.

FIGS. 1 and 2 depict exemplary workflows employing pooled viral delivery of nucleic acids to mammalian cells grown in suspension followed by enrichment for edited cells. In the methods depicted in FIGS. 1 and 2, the editing cassette constructs are delivered to the cells via viral transduction, with the viral particles preferably Poisson-limited. That is, in the present embodiment, editing vectors, e.g., viral editing vectors, are delivered at a low copy number for transduction. Additionally, the components needed for nucleic acid-guided nuclease editing—that is, the editing cassettes and nuclease—are delivered in two steps, as described below.

The workflows depicted in FIGS. 1 and 2 begin with cell culture, typically off-instrument. Again, the cells may be grown in 2D culture, 3D culture (if the cells are viable to be grown in or adapted to 3D culture) or on microcarriers. As described previously, if the cells are initially grown in 2D or 3D culture, the cells are dissociated and added to medium in a growth module in the automated instrument, e.g., a rotating growth module, TFF module or bioreactor comprising cell growth medium. If the cells are grown initially on microcarriers, the microcarriers are transferred to the rotating growth module, TFF module or bioreactor comprising cell growth medium and additional microcarriers. Alternatively, single cells may be grown in suspension using the specialized medium developed by ACCELLTA™ (Haifa, Israel). Cell growth monitoring can be performed by imaging, for example by allowing the microcarriers to settle and imaging the bottom of the rotating growth vial, TFF retentate reservoir or bioreactor. Alternatively, an aliquot of the culture may be removed and run through a separate flow cell, e.g., in a separate module, for imaging. In another alternative, the cells may express a fluorescent protein and fluorescence of the cell culture is measured. In yet another alternative, permittivity or capacitance is used to monitor cell coverage on the microcarriers.

Once grown, approximately 1e7 cells are transferred to the automated instrument for growth. The cells are grown in 3D culture or on microcarriers in the rotating growth module, TFF module or bioreactor for, e.g., three days or until a desired number of cells, e.g., 1e8 cells are present. During this growth cycle, the cells are monitored for cell number, pH, and optionally other parameters. Cell dissociation, if required, is performed by removing cells from microcarriers using enzymes such as collagenase, trypsin or pronase or by physical means such as turbulence created by an impeller. Cell aggregates are broken up by, e.g., passing cell aggregates through a filter, frit or sieve in the presence of, e.g., EDTA, or by agitating the cells.

Prior to transduction, viral vectors comprising the editing cassette constructs are packaged into viral particles off instrument in a manufacturing process. In the present embodiment, the editing cassette constructs are delivered to the mammalian cells to be edited via Poisson-limited numbers of viral editing vectors. The off-instrument generation of viral vectors can be accomplished using any suitable genetic engineering techniques, including without limitation, the standard techniques of PCR, oligonucleotide synthesis, restriction endonuclease digestion, ligation, transformation, plasmid purification, and DNA sequencing. The viral vector preferably comprises, for example, sequences necessary to package the viral vector into viral particles. The viral vector also may contain genes that allow for replication and propagation of virus, though in preferred embodiments such genes are supplied in trans. Additionally, the viral construct may contain genes or genetic sequences from the genome of any known organism incorporated in native form or modified. For example, the preferred viral construct comprises sequences useful for replication of the construct in bacteria.

Promoters useful in the viral editing vectors are known in the art, e.g., the U6 promoter or H1 promoter. Additionally, one or more enhancers also may be present in the viral editing vectors to increase expression of the editing cassettes. Enhancers appropriate for use include the Apo E HCR enhancer, the CMV enhancer. The viral vector also may contain additional genetic elements; for example, additional genetic elements may include a reporter gene, such as one or more genes for a fluorescent marker protein such as GFP or RFP where the cells are sorted by fluorescence-activated cell sorting (FACS). FACS is a specialized type of flow cytometry, providing a method for sorting a heterogeneous mixture of biological cells into two or more containers, one cell at a time, based upon the specific light scattering and fluorescent characteristics of each cell. FACS is a useful scientific process, as it provides fast, objective and quantitative recording of fluorescent signals from individual cells as well as physical separation of cells of particular interest. FACS instrumentation and reagents include the BD FACS-Melody™ (Becton Dickinson, Inc., Franklin Lakes, N.J.); EPICS®Altra™ (Beckman Coulter, Brea Calif.), the FACScan™ and the FACSVantage™ SE (Becton Dickinson, Inc., Franklin Lakes, N.J.). FACS could be a module of the present automated end-to-end instrument or FACS may be separate. FACS is also useful for post-transduction or post-editing analysis to quantify transduction or editing efficiency on-instrument. Other selection techniques involve an easily assayed enzyme such as beta-galactosidase, luciferase, beta-glucuronidase, chloramphenicol acetyl transferase or secreted embryonic alkaline phosphatase; or proteins for which immunoassays are readily available such as hormones or cytokines. Cell printers are also capable of separating cells based on fluorescence and scatter.

Alternatively, magnetic-activated cell sorting (MACS®, Miltenyi Biotec, Bergisch Gladbach, Germany) may be used to select for cells comprising the viral editing vector using surface antigens, and is a practical approach to enriching on instrument. The method uses superparamagnetic nanoparticles and columns. The superparamagnetic nanoparticles are of the order of 100 nm and are coated with antibodies against a particular cell surface antigen. Cells expressing a particular antigen (the coding sequence for which may be on the viral editing vector) attach to the magnetic nanoparticles. After incubating the beads and transduced cells, the solution is transferred to a column in a strong magnetic field. In this step, the cells attached to the nanoparticles (expressing the antigen) stay on the column, while other cells (not expressing the antigen) flow through. The column is placed between permanent magnets so that when the magnetic particle-cell complex passes through it, the tagged cells can be captured. The column consists of steel wool which increases the magnetic field gradient to maximize separation efficiency when the column is placed between the permanent magnets. Alternatively, Dynabeads (Thermo Fisher, Waltham, Mass. USA) may be used to select for the cell surface antigens; in this case, a column is not needed. An alternative option is to have magnetic enrichment or "pull down" of magnetic beads in the rotating growth module, TFF or bioreactor using a magnet positioned against the chamber wall.

A viral delivery system based on any appropriate virus may be used to deliver the editing cassettes to the mammalian cells. Alternatively, hybrid viral systems may be of use. The choice of viral delivery system will depend on various parameters, such as transduction efficiency of the system, pathogenicity, immunological and toxicity concerns, and the like. In general, the five most commonly used classes of viral systems used in gene therapy can be categorized into two groups according to whether their genomes integrate into host cellular chromatin (oncoretroviruses and lentiviruses) or persist in the cell nucleus predominantly as extrachromosomal episomes (adeno-associated virus, adenoviruses and herpesviruses).

For example, in one embodiment, viruses from the Parvoviridae family are utilized. The Parvoviridae is a family of small single-stranded, non-enveloped DNA viruses with genomes approximately 5000 nucleotides long. Included among the family members is adeno-associated virus (AAV), a dependent parvovirus that by definition requires co-infection with another virus (typically an adenovirus or herpesvirus) to initiate and sustain a productive infectious cycle. In the absence of such a helper virus, AAV is still competent to infect or transduce a target cell by receptor-mediated binding and internalization, penetrating the nucleus in both non-dividing and dividing cells.

Another viral delivery system useful with the editing cassettes is a system based on viruses from the family Retroviridae. Retroviruses comprise single-stranded RNA animal viruses that are characterized by two unique features. First, the genome of a retrovirus is diploid, consisting of two copies of the RNA. Second, this RNA is transcribed by the virion-associated enzyme reverse transcriptase into double-stranded DNA. This double-stranded DNA or provirus can then integrate into the host genome and be passed from parent cell to progeny cells as a stably-integrated component of the host genome.

Additionally, Anelloviridae are a recently-discovered family of viruses, classified as vertebrate viruses and have a non-enveloped capsid, which is round with isometric, icosahedral symmetry. The Anelloviridae genome is not segmented and contains a single molecule of circular, negative-sense, single-stranded DNA. The complete genome is 3000-4000 nucleotides long. Anellovirus species are highly prevalent and genetically diverse, causing chronic human viral infections that have not yet been associated with disease. At least 200 different species are present in humans and animals.

In some embodiments, lentiviruses are the preferred members of the retrovirus family for use in the present embodiment. Lentivirus vectors are often pseudotyped with vesicular stomatitis virus glycoprotein (VSV-G), and have been derived from the human immunodeficiency virus (HIV), the etiologic agent of the human acquired immunodeficiency syndrome (AIDS); visna-maedi, which causes encephalitis (visna) or pneumonia in sheep; equine infectious anemia virus (EIAV), which causes autoimmune hemolytic anemia and encephalopathy in horses; feline immunodeficiency virus (FIV), which causes immune deficiency in cats; bovine immunodeficiency virus (BIV) which causes lymphadenopathy and lymphocytosis in cattle; and simian immunodeficiency virus (SIV), which causes immune deficiency and encephalopathy in non-human primates. Vectors that are based on HIV generally retain <5% of the parental genome, and <25% of the genome is incorporated into packaging constructs, which minimizes the possibility of the generation of reverting replication-competent HIV. Biosafety has been further increased by the development of self-inactivating vectors that contain deletions of the regulatory elements in the downstream long-terminal-repeat sequence, eliminating transcription of the packaging signal that is required for vector mobilization. The main advantage to the use of lentiviral vectors is that gene transfer is persistent in most cell types.

Adenoviruses are a relatively well-characterized homogenous group of viruses, including over 50 serotypes. Adenoviruses are medium-sized (90-100 nm), nonenveloped (without an outer lipid bilayer) icosahedral viruses composed of a nucleocapsid and a double-stranded linear DNA genome. There are 57 described serotypes in humans, which are responsible for 5-10% of upper respiratory infections in children, and many infections in adults as well. Adenoviruses are classified as group I under the Baltimore classification scheme, meaning their genomes consist of double-stranded DNA, and are the largest nonenveloped viruses. Because of their large size, they are able to be transported through the endosome (i.e., envelope fusion is not necessary). The virion also has a unique "spike" or fiber associated with each penton base of the capsid that aids in attachment to the host cell via the coxsackie-adenovirus receptor on the surface of the host cell.

The adenovirus genome is linear, non-segmented double-stranded (ds) DNA that is between 26 and 45 kb, allowing the virus to theoretically carry 22 to 40 genes. Although this is significantly larger than other viruses in its Baltimore group, adenovirus is still a very simple virus and is heavily reliant on the host cell for survival and replication. Once the virus has successfully gained entry into the host cell, the endosome acidifies, which alters virus topology by causing capsid components to disassociate. With the help of cellular microtubules, the virus is transported to the nuclear pore complex, where the adenovirus particle disassembles. Viral DNA is subsequently released, which can enter the nucleus via the nuclear pore. After this, the DNA associates with histone molecules; thus, viral gene expression can occur and new virus particles can be generated. Unlike lentiviruses, adenoviral DNA does not integrate into the genome.

Other viral or non-viral systems known to those skilled in the art also may be used to deliver the editing cassettes or editing vectors of the present invention to cells of interest, including but not limited to gene-deleted adenovirus-transposon vectors that stably maintain virus-encoded transgenes in vivo through integration into host cells; systems derived from Sindbis virus or Semliki forest virus; or systems derived from Newcastle disease virus or Sendai virus.

Before transduction into the mammalian cells, the viral vector is packaged into viral particles off-instrument in a manufacturing process. Any method known in the art may be used to produce infectious viral particles comprising a copy of the viral editing cassette delivery vector. Generally, there are two alternative methods for packaging the editing cassette vector viral particles for delivery. One method utilizes packaging cells that stably express in trans the viral proteins that are required for the incorporation of the viral editing cassette vector into viral particles, as well as other sequences necessary or preferred for a particular viral delivery system (for example, sequences needed for replication, structural proteins and viral assembly) and either viral-derived or artificial ligands for tissue entry. The packaging cells then replicate viral sequences, express viral proteins and package the viral editing cassette vectors into infectious viral particles.

Alternatively, a cell line that does not stably express necessary viral proteins may be co-transfected with two or more constructs to achieve efficient production of functional particles. One of the constructs comprises the viral editing cassette vector, and the other construct(s) comprises nucleic acids encoding the proteins necessary to allow the cells to produce functional virus (replication and packaging construct) as well as other helper functions. After production in a packaging cell line, the viral particles containing the viral editing cassette vectors are purified and quantified (titered). Purification strategies include density gradient centrifugation, or, preferably, column chromatographic methods.

Once produced, the virus particles are delivered to the cells in 3D culture at an MOI of approximately <0.3 (e.g., in a Poisson-limited manner), or at an MOI of approximately <0.05 to 1.0, or at an MOI of approximately <0.1 to 0.5, or at an MOI of approximately <0.1 to 0.4. Post-transduction, a selective agent such as an antibiotic is added to the medium to enrich for cells that have been transduced; alternatively, the viral editing cassette vector may comprise a marker for magnetic selection. Because antibiotic selection for mammalian cells can take up to a week of growth in culture, magnetic selection is preferred at this step although FACS selection may also be used. After enrichment, the cells are allowed to grow and recover and then are dissociated and transfected or reverse transfected with an engine plasmid comprising a coding sequence for the nucleic acid-guided nuclease or nickase fusion or with the nucleic acid-guided nuclease or nickase fusion protein itself. After a suitable time for editing and cell recovery, the cells are again enriched, by, e.g., FACS sorting, a magnetic marker (e.g., a second, different marker if magnetic selection was used after cellular transduction), co-editing enrichment or antibiotic selection.

FIG. 2 provides a workflow with additional details. In FIG. 2, a first step comprises cloning the library of editing cassettes into a viral vector backbone followed by production of lentiviral particles is not shown. In parallel, at t=0, cells of interest are seeded and grown in, e.g., a rotating growth module, TFF module or bioreactor on-instrument and dissociated as described above. At t=4, the lentivirus is delivered to the cells at an MOI of approximately <0.3 (e.g., in a Poisson-limited manner), or at an MOI of approximately <0.05 to 0.8, or at an MOI of approximately <0.1 to 0.5, or at an MOI of approximately <0.1 to 0.4., where the lentivirus transfects the cells. At t=24-48 hours post transduction, antibiotic selection starts, where an antibiotic such as, e.g., blasticidin, is added to enrich for cells that were transduced with the viral editing cassette vector. After sufficient time for enrichment (approximately t=72 hours), the surviving cells are passaged and separated or detached from microcarriers in e.g., the TFF module as described in relation to FIGS. 4F and 4G or by, e.g., impeller-induced turbulence in the bioreactor (see the protocols in Example XI). Following separation or detachment, the cells are re-seeded and grown in the rotating growth module, TFF module or bioreactor. Optionally, in some embodiments the re-seeding and growth steps are performed twice. After re-seeding and growth the cells are transfected in a "reverse transfection" process with the engine plasmid or enzyme where the cells are re-seeded in the presence of lipofectamine and the engine vector or enzyme. Following transfection, at approximately t=216 hours, the cells are again grown, separated and detached and separated from microcarriers. The cells are then unloaded from the automated instrument as a pool or the cells can once again be enriched, this time for cells transfected with the engine plasmid or enzyme via, e.g., fluorescent markers or magnetic enrichment in an optional enrichment module or off-instrument.

Cell Growth and Editing Modules

The Rotating Growth Module

Figure 3A:
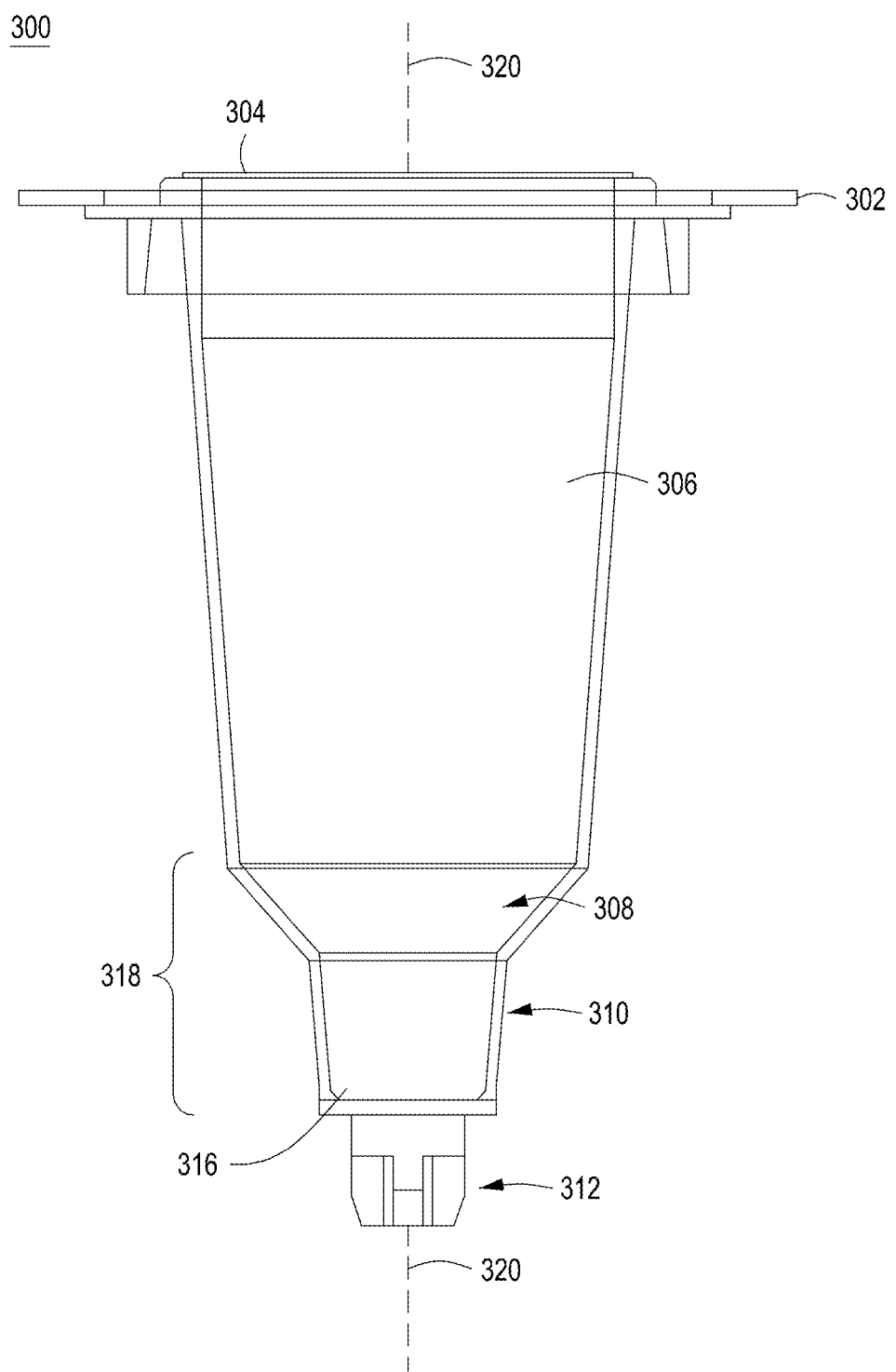
FIG. 3A depicts one embodiment of a rotating growth vial for use with the rotating growth module described herein and in relation to FIGS. 3C-3E.

As described above, the present disclosure provides a fully-automated end-to-end instrument to process the cells without human intervention to enhance cell processing uniformity and to maintain the integrity of the cell culture. FIG. 3A shows one embodiment of a rotating growth vial 300 to be used in a rotating growth module as the growth module for one embodiment of the automated multi-module cell processing instruments described herein. The rotating growth module can be used for both cell growth, and for cell transduction and transfection. The rotating growth vial 300 is an optically-transparent container having an open end 304 for receiving liquid media and cells, a central vial region 306 that defines the primary container for growing cells, a tapered-to-constricted region 318 defining at least one light path 310, a closed end 316, and a drive engagement mechanism 312. The rotating growth vial 300 has a central longitudinal axis 320 around which the vial rotates, and the light path 310 is generally perpendicular to the longitudinal axis of the vial. The first light path 310 is positioned in the lower constricted portion of the tapered-to-constricted region 318. Optionally, some embodiments of the rotating growth vial 300 have a second light path 308 in the tapered region of the tapered-to-constricted region 318. Both light paths in this embodiment are positioned in a region of the rotating growth vial that is constantly filled with the cell culture (cells+growth media) and are not affected by the rotational speed of the growth vial. The first light path 310 is shorter than the second light path 308 allowing for, e.g., sensitive measurement of OD values when the OD values of the cell culture in the vial are at a high level (e.g., later in the cell growth process), whereas the second light path 308 allows for, e.g., sensitive measurement of OD values when the OD values of the cell culture in the vial are at a lower level (e.g., earlier in the cell growth process).

The drive engagement mechanism 312 engages with a motor (not shown) to rotate the vial. In some embodiments, the motor drives the drive engagement mechanism 312 such that the rotating growth vial 300 is rotated in one direction only, and in other embodiments, the rotating growth vial 300 is rotated in a first direction for a first amount of time or periodicity, rotated in a second direction (i.e., the opposite direction) for a second amount of time or periodicity, and this process may be repeated so that the rotating growth vial 300 (and the cell culture contents) are subjected to an oscillating motion. Further, the choice of whether the culture is subjected to oscillation and the periodicity therefor may be selected by the user. The first amount of time and the second amount of time may be the same or may be different.

The amount of time may be 1, 2, 3, 4, 5, or more seconds, or may be 1, 2, 3, 4 or more minutes. In another embodiment, in an early stage of cell growth the rotating growth vial 300 may be oscillated at a first periodicity (e.g., every 60 seconds), and then a later stage of cell growth the rotating growth vial 300 may be oscillated at a second periodicity (e.g., every one second) different from the first periodicity.

The rotating growth vial 300 may be reusable or, preferably, the rotating growth vial is consumable. In some embodiments, the rotating growth vial is consumable and is presented to the user pre-filled with growth medium, where the vial is hermetically sealed at the open end 304 with a foil seal. A medium-filled rotating growth vial packaged in such a manner may be part of a kit for use with a stand-alone cell growth device or with a cell growth module that is part of an automated multi-module cell processing system. To introduce cells into the vial, a user need only pipette up a desired volume of cells and use the pipette tip to punch through the foil seal of the vial. Open end 304 may optionally include an extended lip 302 to overlap and engage with the cell growth device. In automated systems, the rotating growth vial 300 may be tagged with a barcode or other identifying means that can be read by a scanner or camera (not shown) that is part of the automated system.

The volume of the rotating growth vial 300 and the volume of the cell culture (including growth medium) may vary, but the volume of the rotating growth vial 300 must be large enough to generate a specified total number of cells. In practice, the volume of the rotating growth vial 300 may range from 5-1000 mL, 10-500 mL, or from 20-250 mL. Likewise, the volume of the cell culture (cells+growth media) should be appropriate to allow proper aeration and mixing in the rotating growth vial 300. Proper aeration promotes uniform cellular respiration within the growth medium. Thus, the volume of the cell culture should be approximately 5-85% of the volume of the growth vial or from 20-60% of the volume of the growth vial. For example, for a 300 mL growth vial, the volume of the cell culture would be from about 15 mL to about 260 mL, or from 6 mL to about 180 mL.

The rotating growth vial 300 preferably is fabricated from a bio-compatible optically transparent material—or at least the portion of the vial comprising a light path for imaging is transparent. Additionally, material from which the rotating growth vial is fabricated should be able to be cooled to about 4° C. or lower and heated to about 55° C. or higher to accommodate both temperature-based cell assays and long-term storage at low temperatures. Further, the material that is used to fabricate the vial must be able to withstand temperatures up to 55° C. without deformation while spinning. Suitable materials include cyclic olefin copolymer (COC), glass, polyvinyl chloride, polyethylene, polyetheretherketone (PEEK), polypropylene, polycarbonate, poly(methyl methacrylate) (PMMA), polysulfone, poly(dimethylsiloxane), and co-polymers of these and other polymers. Preferred materials include polypropylene, polycarbonate, or polystyrene. In some embodiments, the rotating growth vial is inexpensively fabricated by, e.g., injection molding or extrusion.

Figure 3B:
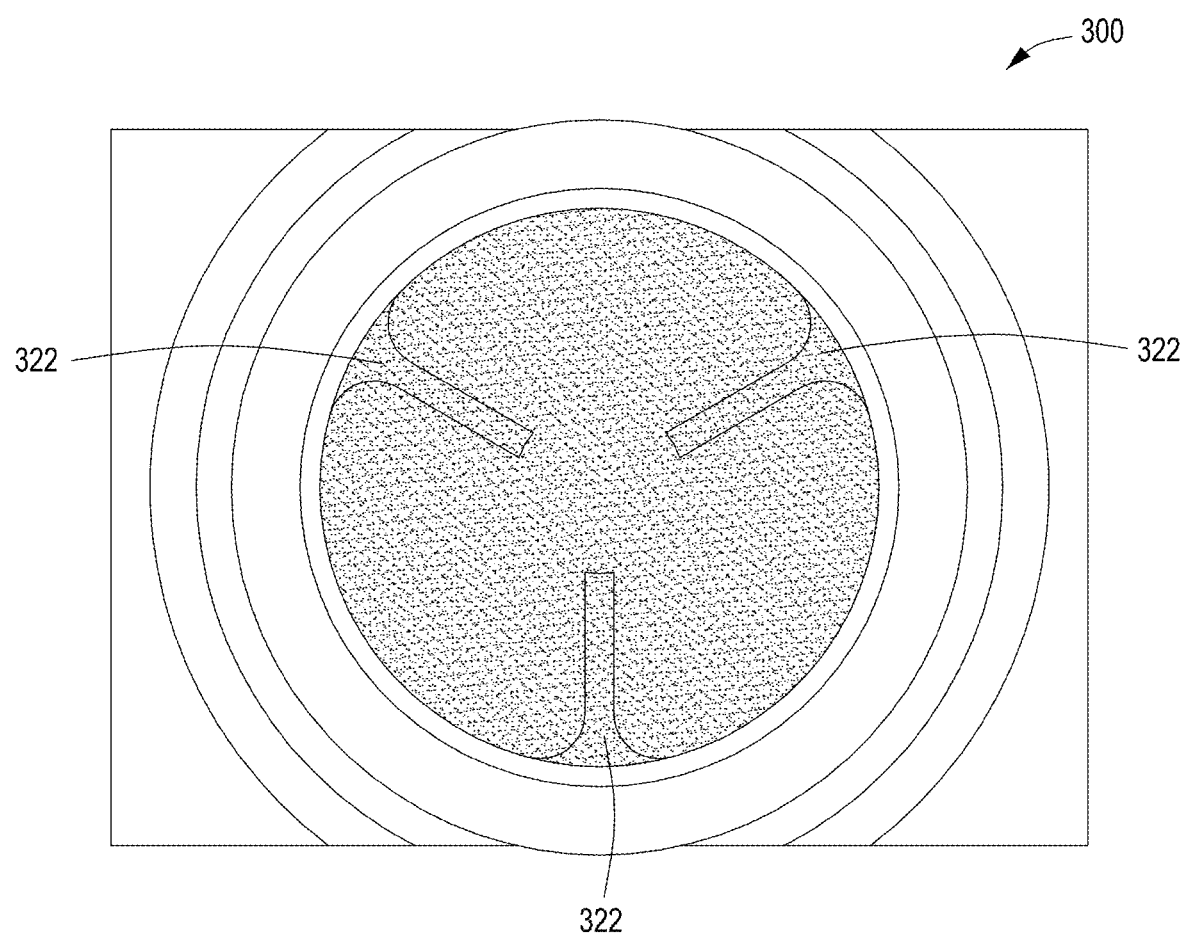
FIG. 3B illustrates a top-down view of the rotating growth vial depicted in FIG. 3A, showing optional internal "fins" or "paddles" for growing mammalian cells.

FIG. 3B illustrates a top view of a rotating growth vial 300. In some examples, the vial 300 may include one or more fins or paddles 322 affixed to an inner surface of the vial wall, where the paddles protrude toward the center of the vial 300. The vial 300 shown in FIG. 3B includes three paddles 322 that are substantially equally spaced around the periphery of the vial 300, but in other examples vial 300 may include two, four, or more paddles 322. The paddles, in some implementations, provide increased mixing and aeration within the vial 300 rotating within a cell growth device, which facilitates cell growth. In other configurations, there may be concentric rows of raised features disposed on the inner surface of the rotating growth vial and the features may be arranged horizontally or vertically; and in other aspects, there may be a spiral configuration of raised features disposed on the inner surface of the rotating growth vial. In alternative aspects, the fins or paddles or concentric rows of raised features may be disposed upon a post or center structure of a rotating growth vial, where the paddles or features radiate out from the center of the vial toward the inner walls of the vial. In some aspects, the width of the paddles or interior features varies with the size or volume of the rotating growth vial, and may range from ⅛ to just under ½ the radius of the rotating growth vial, or from ¼ to ⅓ the radius of the rotating growth vial. The length of the paddles varies with the size or volume of the rotating growth vial and may range from ¼ to ⅘ the length of the rotating growth vial, or from ⅓ to ¾ the length of the rotating growth vial.

The paddles themselves—depending on the speed of rotation of the vial—may provide adequate turbulence to either dissociate cell aggregates or to detach cells from microcarriers. In addition, the paddles may be modified to comprise strainers, frits or sieves for dissociating cell aggregates. That is, the paddles may comprise pores that dissociate the cell aggregates, where the pores range in size from 10 to 400 microns in size, or from 20 to 200 microns in size, or from 30 to 100 microns in size. In some embodiments of the automated instruments, there may be two different types of rotating growth vials present, one type without fins and/or strainers or sieves present for cell growth, and one with fins or features and with strainers or sieves for cell dissociation where cells and medium are transferred to and between the growth vial and dissociation vial by an automated liquid handling system.

Figure 3C:
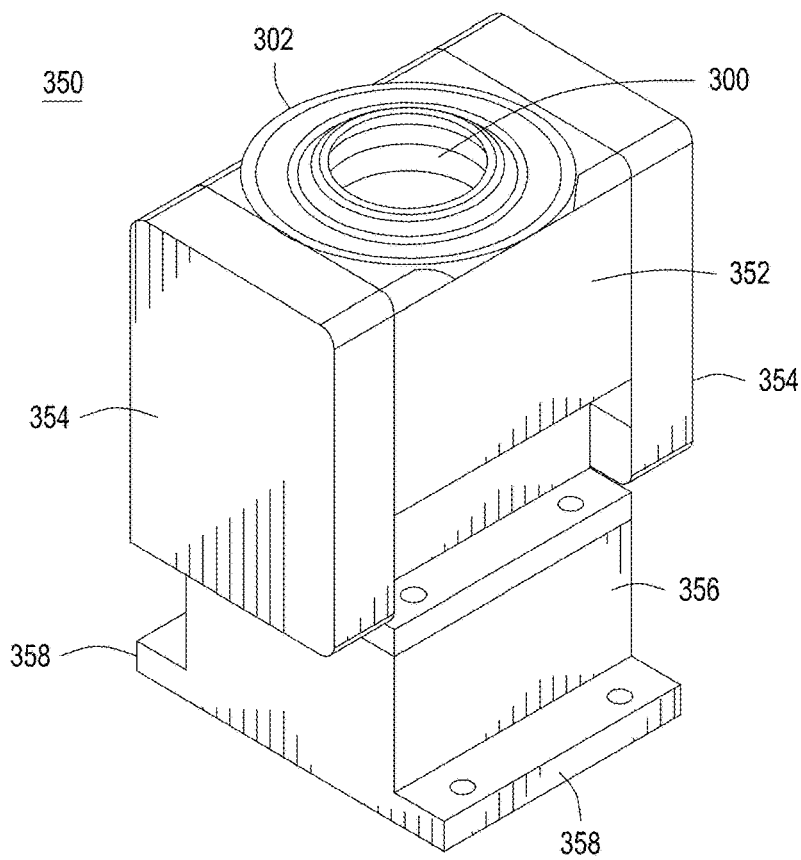
FIG. 3C is a perspective view of one embodiment of a rotating growth vial in a rotating growth module housing.
Figure 3D:
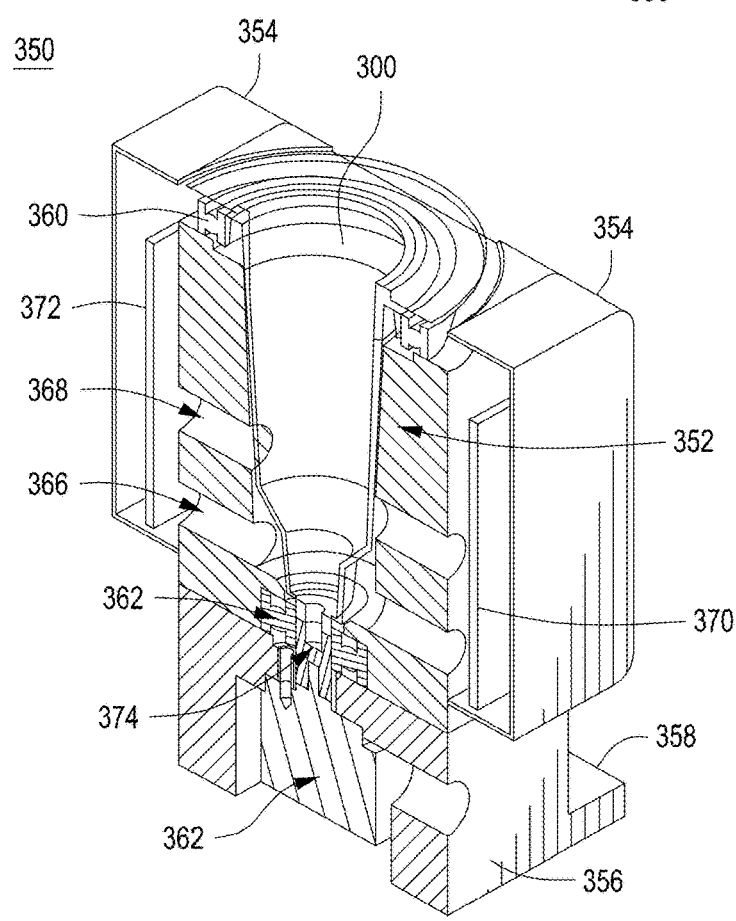
FIG. 3D depicts a cut-away view of the cell growth module from FIG. 3C.

FIG. 3C is a perspective view of one embodiment of a cell growth device 330. FIG. 3D depicts a cut-away view of the cell growth device 330 from FIG. 3C. In both figures, the rotating growth vial 300 is seen positioned inside a main housing 336 with the extended lip 302 of the rotating growth vial 300 extending above the main housing 336. Additionally, end housings 352, a lower housing 332 and flanges 334 are indicated in both figures. Flanges 334 are used to attach the cell growth device 330 to heating/cooling means or other structure (not shown). FIG. 3D depicts additional detail. In FIG. 3D, upper bearing 342 and lower bearing 340 are shown positioned within main housing 336. Upper bearing 342 and lower bearing 340 support the vertical load of rotating growth vial 300. Lower housing 332 contains the drive motor 338. The cell growth device 330 of FIG. 3C may comprise two light paths; a primary light path 344, and a secondary light path 350. Light path 344 corresponds to light path 310 positioned in the constricted portion of the tapered-to-constricted portion of the rotating growth vial 300, and light path 350 corresponds to light path 308 in the tapered portion of the tapered-to-constricted portion of the rotating growth via 316. Light paths 310 and 308 are not shown in FIG. 3D but may be seen in FIG. 3A. In addition to light paths 344 and 340, there is an emission board 348 to illuminate the light path(s), and detector board 346 to detect the light after the light travels through the cell culture liquid in the rotating growth vial 300.

Cell growth monitoring can be performed by imaging, for example, by allowing the microcarriers to settle and imaging the bottom of the rotating growth vial. Alternatively, an aliquot of the culture is removed and run through a flow cell for imaging. In yet another alternative, the cells may express a fluorescent protein and fluorescence is measured. In yet another alternative, the cell density may be measured by light absorbance at 250-350 nm at light path 310.

The motor 328 engages with drive mechanism 312 and is used to rotate the rotating growth vial 300. In some embodiments, motor 338 is a brushless DC type drive motor with built-in drive controls that can be set to hold a constant revolution per minute (RPM) between 0 and about 3000 RPM. Alternatively, other motor types such as a stepper, servo, brushed DC, and the like can be used. Optionally, the motor 338 may also have direction control to allow reversing of the rotational direction, and a tachometer to sense and report actual RPM. The motor is controlled by a processor (not shown) according to, e.g., standard protocols programmed into the processor and/or user input, and the motor may be configured to vary RPM to cause axial precession of the cell culture thereby enhancing mixing, e.g., to prevent cell aggregation, increase aeration, and optimize cellular respiration.

Main housing 336, end housings 352 and lower housing 332 of the cell growth device 330 may be fabricated from any suitable, robust material including aluminum, stainless steel, or other thermally conductive materials, including plastics. These structures or portions thereof can be created through various techniques, e.g., metal fabrication, injection molding, creation of structural layers that are fused, etc. Whereas the rotating growth vial 300 is envisioned in some embodiments to be reusable, but preferably is consumable, the other components of the cell growth device 330 are preferably reusable and function as a stand-alone benchtop device or as a module in a multi-module cell processing system.

Figure 3E:
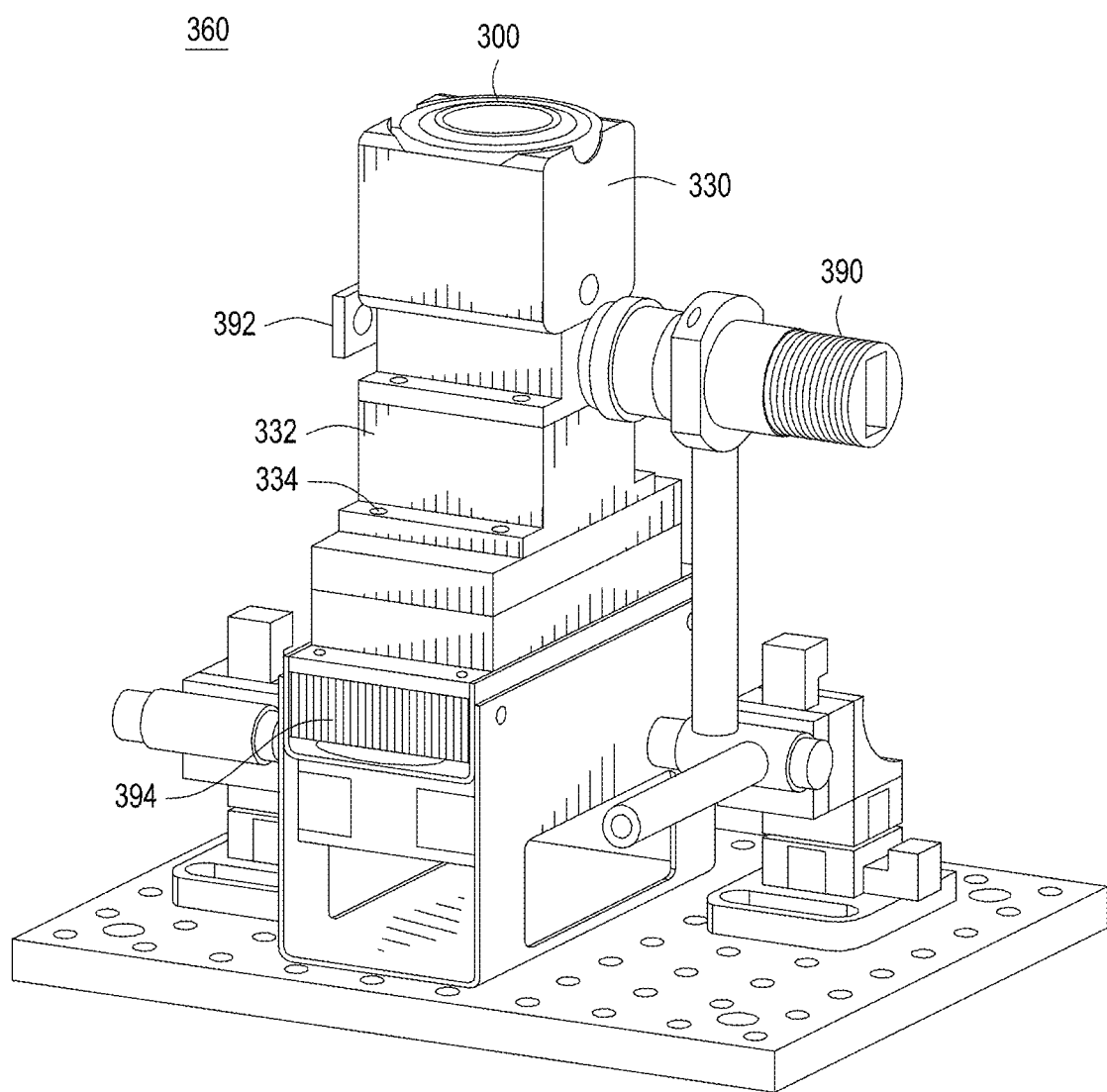
FIG. 3E illustrates the cell growth module of FIG. 3C coupled to LED, detector, and temperature regulating components.

FIG. 3E illustrates a cell growth device 330 as part of an assembly comprising the cell growth device 330 of FIG. 3C coupled to light source 390, detector 392, and thermal components 394. The rotating growth vial 300 is inserted into the cell growth device. Components of the light source 390 and detector 392 (e.g., such as a photodiode with gain control to cover 5-log) are coupled to the main housing of the cell growth device. The lower housing 332 that houses the motor that rotates the rotating growth vial 300 is illustrated, as is one of the flanges 334 that secures the cell growth device 330 to the assembly. Also, the thermal components 394 illustrated are a Peltier device or thermoelectric cooler. In this embodiment, thermal control is accomplished by attachment and electrical integration of the cell growth device 330 to the thermal components 394 via the flange 334 on the base of the lower housing 332. Thermoelectric coolers are capable of "pumping" heat to either side of a junction, either cooling a surface or heating a surface depending on the direction of current flow. In one embodiment, a thermistor is used to measure the temperature of the main housing and then, through a standard electronic proportional-integral-derivative (PID) controller loop, the rotating growth vial 300 is controlled to approximately +/−0.5° C. In yet another alternative, the detector is replaced with an imaging camera. The geometry of the constricted portion of the rotating growth vial 300 containing light path 310 is further tapered to collect settled cell aggregates or microcarriers coated with cells when rotation is paused. The stacked cell aggregates or microcarriers with cells are imaged. Total cell number can be derived from the height of the stacked cell aggregates. Total cell number can be derived from the combined height of the microcarriers coated with cells and the observed confluency of cells on a subset of microcarriers.

In use, cells are inoculated (cells can be pipetted, e.g., from an automated liquid handling system or by a user) into pre-filled growth media of a rotating growth vial 300 by piercing though the foil seal or film. The programmed software of the cell growth device 330 sets the control temperature for growth, typically 30° C., then slowly starts the rotation of the rotating growth vial 300. The cell/growth media mixture slowly moves vertically up the wall due to centrifugal force allowing the rotating growth vial 300 to expose a large surface area of the mixture to an $O_2$ or $CO_2$ environment. If enhanced mixing is required, e.g., to optimize growth conditions, the speed of the vial rotation can be varied to cause an axial precession of the liquid, and/or a complete directional change can be performed at programmed intervals.

In addition to imaging, other cell growth parameters can be measured. Other optional measures of cell growth may be made including spectroscopy using visible, UV, or near infrared (NIR) light, measuring, e.g., the concentration of nutrients and/or wastes in the cell culture and/or other spectral properties can be measured via, e.g., dielectric impedance spectroscopy, visible fluorescence, fluorescence polarization, or luminescence. Additionally, the cell growth device 330 may include additional sensors for measuring, e.g., dissolved oxygen, carbon dioxide, pH, conductivity, and the like. For additional details regarding rotating growth vials and cell growth devices see U.S. Pat. Nos. 10,435,662; and 10,443,031; and U.S. Ser. No. 16/552,981, filed 7 Aug. 2019; and Ser. No. 16/780,640, filed 3 Feb. 2020.

The Tangential Flow Filtration Module

An alternative to the rotating growth module is a tangential flow filtration (TFF) module as shown in FIGS. 4A-4G. The TFF module shown in FIGS. 4A-4G is a module that can grow, perform buffer exchange, concentrate cells and dissociate cells or detach cells from microcarriers so that the cells may be transfected or transduced with the nucleic acids needed for engineering or editing the cell's genome. The TFF module also supports cell transduction and cell transfection or reverse transfection.

Figure 4A:
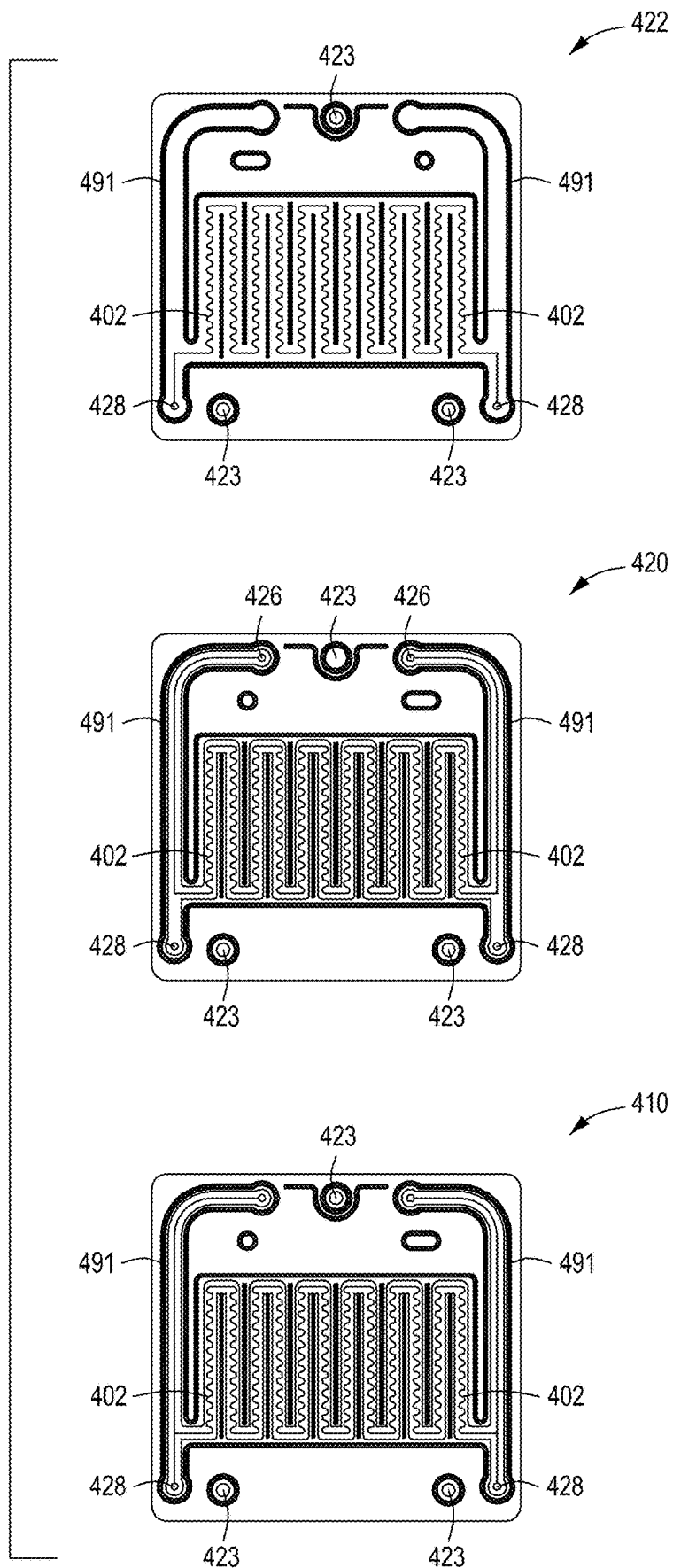
FIG. 4A depicts retentate (top) and permeate (middle) members for use in a tangential flow filtration module (e.g., cell growth and/or concentration module), as well as the retentate and permeate members assembled into a tangential flow assembly (bottom).

FIG. 4A shows a retentate member 422 (top), permeate member 420 (middle) and a tangential flow assembly 410 (bottom) comprising the retentate member 422, membrane 424 (not seen in FIG. 4A), and permeate member 420 (also not seen). In FIG. 4A, retentate member 422 comprises a tangential flow channel 402, which has a serpentine configuration that initiates at one lower corner of retentate member 422—specifically at retentate port 428—traverses across and up then down and across retentate member 422, ending in the other lower corner of retentate member 422 at a second retentate port 428. Also seen on retentate member 422 are energy directors 491, which circumscribe the region where a membrane or filter (not seen in this FIG. 4A) is seated, as well as interdigitate between areas of channel 402. Energy directors 491 in this embodiment mate with and serve to facilitate ultrasonic welding or bonding of retentate member 422 with permeate/filtrate member 420 via the energy director component 491 on permeate/filtrate member 420 (at right). Additionally, countersinks 423 can be seen, two on the bottom one at the top middle of retentate member 422. Countersinks 423 are used to couple and tangential flow assembly 410 to a reservoir assembly (not seen in this FIG. 4A but see FIG. 4B).

Permeate/filtrate member 420 is seen in the middle of FIG. 4A and comprises, in addition to energy director 491, through-holes for retentate ports 428 at each bottom corner (which mate with the through-holes for retentate ports 428 at the bottom corners of retentate member 422), as well as a tangential flow channel 402 and two permeate/filtrate ports 426 positioned at the top and center of permeate member 420. The tangential flow channel 402 structure in this embodiment has a serpentine configuration and an undulating geometry, although other geometries may be used. Permeate member 420 also comprises countersinks 423, coincident with the countersinks 423 on retentate member 420.

At bottom is a tangential flow assembly 410 comprising the retentate member 422 and permeate member 420 seen in this FIG. 4A. In this view, retentate member 422 is "on top" of the view, a membrane (not seen in this view of the assembly) would be adjacent and under retentate member 422 and permeate member 420 (also not seen in this view of the assembly) is adjacent to and beneath the membrane. Again countersinks 423 are seen, where the countersinks in the retentate member 422 and the permeate member 420 are coincident and configured to mate with threads or mating elements for the countersinks disposed on a reservoir assembly (not seen in FIG. 4A but see FIG. 4B).

A membrane or filter is disposed between the retentate and permeate members, where fluids can flow through the membrane but cells cannot and are thus retained in the flow channel disposed in the retentate member. Filters or membranes appropriate for use in the TFF module are those that are solvent resistant, are contamination free during filtration, and are able to retain the types and sizes of cells of interest. For example, in order to retain small cell types, pore sizes can be as low as 0.5 µm, however for other cell types, the pore sizes can be as high as 20 µm. Indeed, the pore sizes useful in the TFF module include filters with sizes from 0.50 and larger. The filters may be fabricated from any suitable non-reactive material including cellulose mixed ester (cellulose nitrate and acetate) (CME), polycarbonate (PC), polyvinylidene fluoride (PVDF), polyethersulfone (PES), polytetrafluoroethylene (PTFE), nylon, glass fiber, or metal substrates as in the case of laser or electrochemical etching.

The length of the channel structure 402 may vary depending on the volume of the cell culture to be grown. The length of the channel structure typically is from 60 mm to 300 mm, or from 70 mm to 200 mm, or from 80 mm to 100 mm. The cross-section configuration of the flow channel 402 may be round, elliptical, oval, square, rectangular, trapezoidal, or irregular. If square, rectangular, or another shape with generally straight sides, the cross section may be from about 10 to 1000 wide, or from 200 to 800 µm wide, or from 300 to 700 wide, or from 400 to 600 wide; and from about 10 to 1000 high, or from 200 to 800 high, or from 300 to 700 high, or from 400 to 600 high. If the cross section of the flow channel 302 is generally round, oval or elliptical, the radius of the channel may be from about 50 to 1000 in hydraulic radius, or from 5 µm to 800 in hydraulic radius, or from 200 to 700 in hydraulic radius, or from 300 to 600 wide in hydraulic radius, or from about 200 to 500 in hydraulic radius. Moreover, the volume of the channel in the retentate 422 and permeate 420 members may be different depending on the depth of the channel in each member.

Figure 4B:
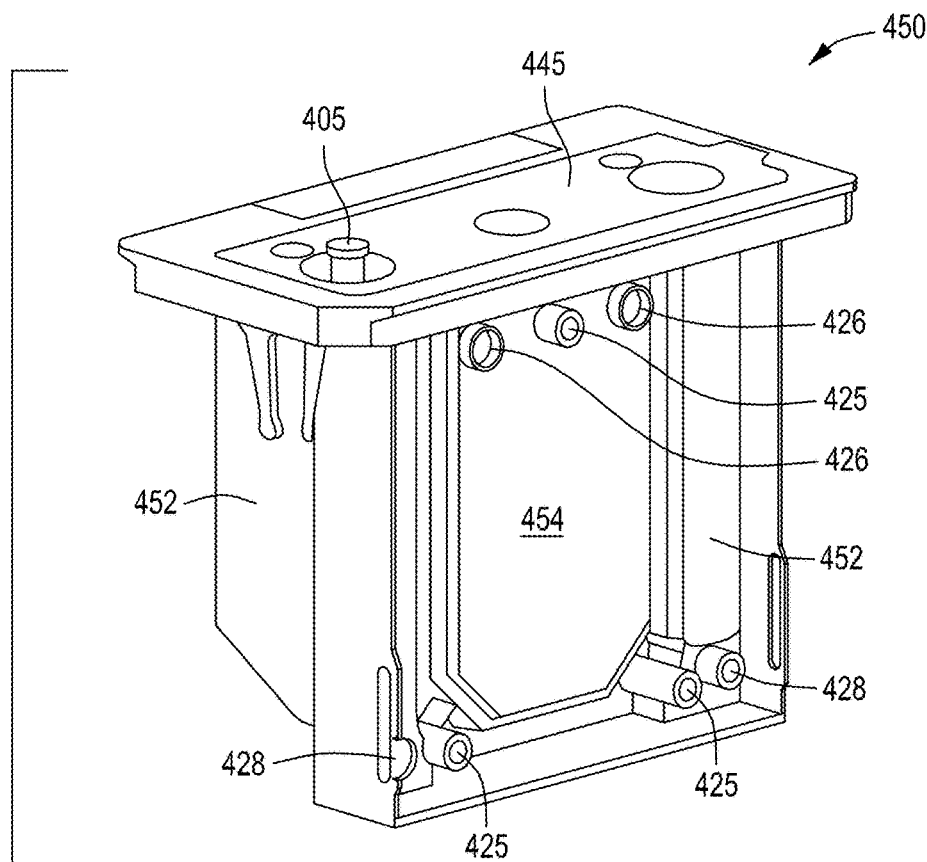
FIG. 4B depicts two side perspective views of a reservoir assembly of a tangential flow filtration module.
Figure 4B:
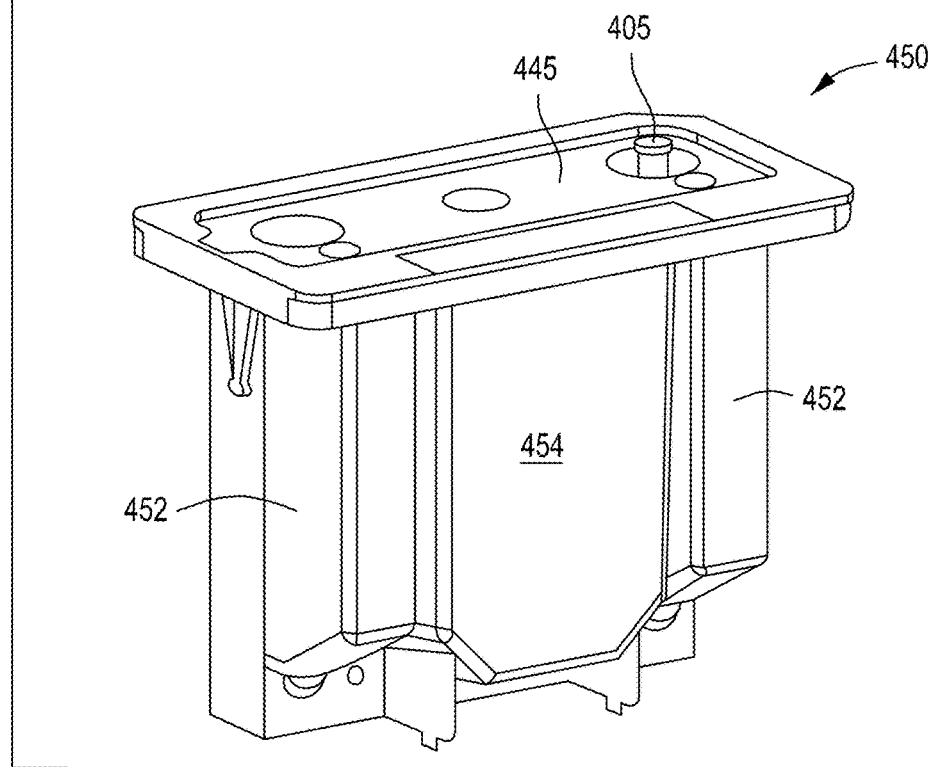

FIG. 4B shows front perspective (right) and rear perspective (left) views of a reservoir assembly 450 configured to be used with the tangential flow assembly 410 seen in FIG. 4A. Seen in the front perspective view (e.g., "front" being the side of reservoir assembly 450 that is coupled to the tangential flow assembly 410 seen in FIG. 4A) are retentate reservoirs 452 on either side of permeate reservoir 454. Also seen are permeate ports 426, retentate ports 428, and three threads or mating elements 425 for countersinks 423 (countersinks 423 not seen in this FIG. 4B). Threads or mating elements 425 for countersinks 423 are configured to mate or couple the tangential flow assembly 410 (seen in FIG. 4A) to reservoir assembly 450. Alternatively, or in addition, fasteners, sonic welding or heat stakes may be used to mate or couple the tangential flow assembly 410 to reservoir assembly 450. In addition is seen gasket 445 covering the top of reservoir assembly 450. Gasket 445 is described in detail in relation to FIG. 4E. At left in FIG. 4B is a rear perspective view of reservoir assembly 450, where "rear" is the side of reservoir assembly 450 that is not coupled to the tangential flow assembly. Seen are retentate reservoirs 452, permeate reservoir 454, and gasket 445.

The TFF module may be fabricated from any robust material in which channels (and channel branches) may be milled including stainless steel, silicon, glass, aluminum, or plastics including cyclic-olefin copolymer (COC), cyclo-olefin polymer (COP), polystyrene, polyvinyl chloride, polyethylene, polyethylene, polypropylene, acrylonitrile butadiene, polycarbonate, polyetheretheketone (PEEK), poly(methyl methylacrylate) (PMMA), polysulfone, and polyurethane, and co-polymers of these and other polymers. If the TFF module is disposable, preferably it is made of plastic. In some embodiments, the material used to fabricate the TFF module is thermally-conductive so that the cell culture may be heated or cooled to a desired temperature. In certain embodiments, the TFF module is formed by precision mechanical machining, laser machining, electro discharge machining (for metal devices); wet or dry etching (for silicon devices); dry or wet etching, powder or sandblasting, photostructuring (for glass devices); or thermoforming, injection molding, hot embossing, or laser machining (for plastic devices) using the materials mentioned above that are amenable to this mass production techniques.

Figure 4C:
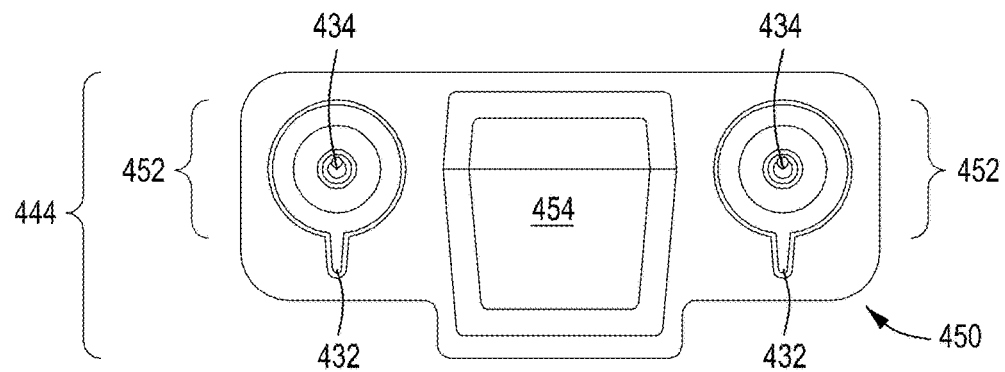
FIGS. 4C-4E depict an exemplary top, with fluidic and pneumatic ports and gasket suitable for the reservoir assemblies shown in FIG. 4B.
Figure 4D:
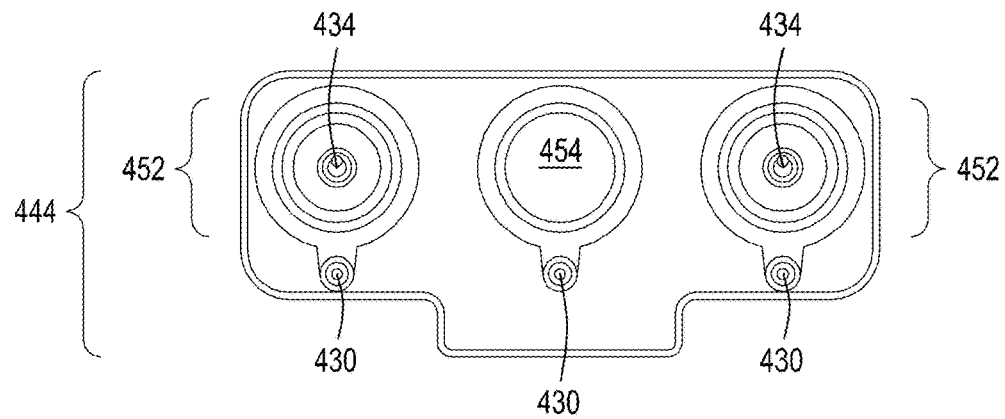
Figure 4E:
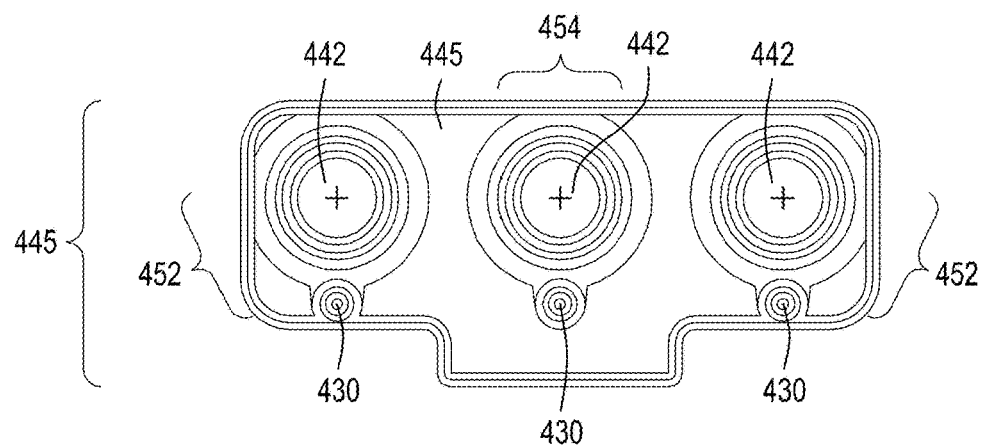

FIG. 4C depicts a top-down view of the reservoir assemblies 450 shown in FIG. 4B. FIG. 4D depicts a cover 444 for reservoir assembly 450 shown in FIGS. 4B and 4E depicts a gasket 445 that in operation is disposed on cover 444 of reservoir assemblies 450 shown in FIG. 4B. FIG. 4C is a top-down view of reservoir assembly 450, showing the tops of the two retentate reservoirs 452, one on either side of permeate reservoir 454. Also seen are grooves 432 that will mate with a pneumatic port (not shown), and fluid channels 434 that reside at the bottom of retentate reservoirs 452, which fluidically couple the retentate reservoirs 452 with the retentate ports 428 (not shown), via the through-holes for the retentate ports in permeate member 420 and membrane 424 (also not shown). FIG. 4D depicts a cover 444 that is configured to be disposed upon the top of reservoir assembly 450. Cover 444 has round cut-outs at the top of retentate reservoirs 452 and permeate/filtrate reservoir 454. Again, at the bottom of retentate reservoirs 452 fluid channels 434 can be seen, where fluid channels 434 fluidically couple retentate reservoirs 452 with the retentate ports 428 (not shown). Also shown are three pneumatic ports 430 for each retentate reservoir 452 and permeate/filtrate reservoir 454. FIG. 4E depicts a gasket 445 that is configures to be disposed upon the cover 444 of reservoir assembly 450. Seen are three fluid transfer ports 442 for each retentate reservoir 452 and for permeate/filtrate reservoir 454. Again, three pneumatic ports 330, for each retentate reservoir 452 and for permeate/filtrate reservoir 454, are shown.

The overall work flow for cell growth comprises loading a cell culture to be grown into a first retentate reservoir, preferably bubbling air or an appropriate gas through the cell culture, passing or flowing the cell culture through the first retentate port then tangentially through the TFF channel structure while collecting medium or buffer through one or both of the permeate ports 426, collecting the cell culture through a second retentate port 428 into a second retentate reservoir, optionally adding additional fresh or different medium to the cell culture and optionally bubbling air or gas through the cell culture, then repeating the process, all while measuring, e.g., the optical density of the cell culture in the retentate reservoirs continuously or at desired intervals. Again, cell growth monitoring can be performed by imaging, for example, by allowing the microcarriers to settle and imaging the bottom of the TFF retentate reservoir. Alternatively, an aliquot of the culture is removed and run through a flow cell for imaging. In yet another alternative, the cells may express a fluorescent protein and fluorescence is measured.

In the channel structure, the membrane bifurcating the flow channels retains the cells on one side of the membrane (the retentate side 422) and allows unwanted medium or buffer to flow across the membrane into a filtrate or permeate side (e.g., permeate member 420) of the device. Bubbling air or other appropriate gas through the cell culture both aerates and mixes the culture to enhance cell growth. During the process, medium that is removed during the flow through the channel structure is removed through the permeate/filtrate ports 426. Alternatively, cells can be grown in one reservoir with bubbling or agitation without passing the cells through the TFF channel from one reservoir to the other.

The overall workflow for cell concentration using the TFF module involves flowing a cell culture or cell sample tangentially through the channel structure. As with the cell growth process, the membrane bifurcating the flow channels retains the cells on one side of the membrane and allows unwanted medium or buffer to flow across the membrane into a permeate/filtrate side (e.g., permeate member 420) of the device. In this process, a fixed volume of cells in medium or buffer is driven through the device until the cell sample is collected into one of the retentate ports 428, and the medium/buffer that has passed through the membrane is collected through one or both of the permeate/filtrate ports 426. All types of prokaryotic and eukaryotic cells—both adherent and non-adherent cells—can be grown in the TFF module. Adherent cells may be grown on beads or other cell scaffolds suspended in medium that flow through the TFF module.

The medium or buffer used to suspend the cells in the TFF module may be any suitable medium or buffer for the type of cells being transformed or transfected, such as MEM, DMEM, IMDM, RPMI, Hanks', PBS and Ringer's solution, where the media may be provided in a reagent cartridge as part of a kit. For culture of adherent cells, cells may be disposed on microcarriers or other type of scaffold suspended in medium. The microcarriers of particular use typically have a diameter of 50-500 µm and have a density slightly greater than that of the culture medium thus facilitating an easy separation of cells and medium for, e.g., medium exchange yet the density must also be sufficiently low to allow complete suspension of the carriers at a minimum stirring rate in order to avoid hydrodynamic damage to the cells.

In both the cell growth and concentration processes, passing the cell sample through the TFF module and collecting the cells in one of the retentate ports 428 while collecting the medium in one of the permeate/filtrate ports 426 is considered "one pass" of the cell sample. The transfer between retentate reservoirs "flips" the culture. The retentate and permeate ports collecting the cells and medium, respectively, for a given pass reside on the same end of TFF module with fluidic connections arranged so that there are two distinct flow layers for the retentate and permeate/filtrate sides, but if the retentate port 428 resides on the retentate member of device/module (that is, the cells are driven through the channel above the membrane and the filtrate (medium) passes to the portion of the channel below the membrane), the permeate/filtrate port 426 will reside on the permeate member of device/module and vice versa (that is, if the cell sample is driven through the channel below the membrane, the filtrate (medium) passes to the portion of the channel above the membrane). Due to the high pressures used to transfer the cell culture and fluids through the flow channel of the TFF module, the effect of gravity is negligible.

At the conclusion of a "pass" in either of the growth and concentration processes, the cell sample is collected by passing through the retentate port 428 and into the retentate reservoir (not shown). To initiate another "pass", the cell sample is passed again through the TFF module, this time in a flow direction that is reversed from the first pass. The cell sample is collected by passing through the retentate port 428 and into retentate reservoir (not shown) on the opposite end of the device/module from the retentate port 428 that was used to collect cells during the first pass. Likewise, the medium/buffer that passes through the membrane on the second pass is collected through the permeate port 426 on the opposite end of the device/module from the permeate port 426 that was used to collect the filtrate during the first pass, or through both ports. This alternating process of passing the retentate (the concentrated cell sample) through the device/module is repeated until the cells have been grown to a desired optical density, and/or concentrated to a desired volume, and both permeate ports (i.e., if there are more than one) can be open during the passes to reduce operating time. In addition, buffer exchange may be effected by adding a desired buffer (or fresh medium) to the cell sample in the retentate reservoir, before initiating another "pass", and repeating this process until the old medium or buffer is diluted and filtered out and the cells reside in fresh medium or buffer. Note that buffer exchange and cell growth may (and typically do) take place simultaneously, and buffer exchange and cell concentration may (and typically do) take place simultaneously. For further information and alternative embodiments on TFFs see, e.g., U.S. Ser. No. 16/798, 302, filed 22 Feb. 2020.

Figure 4F:
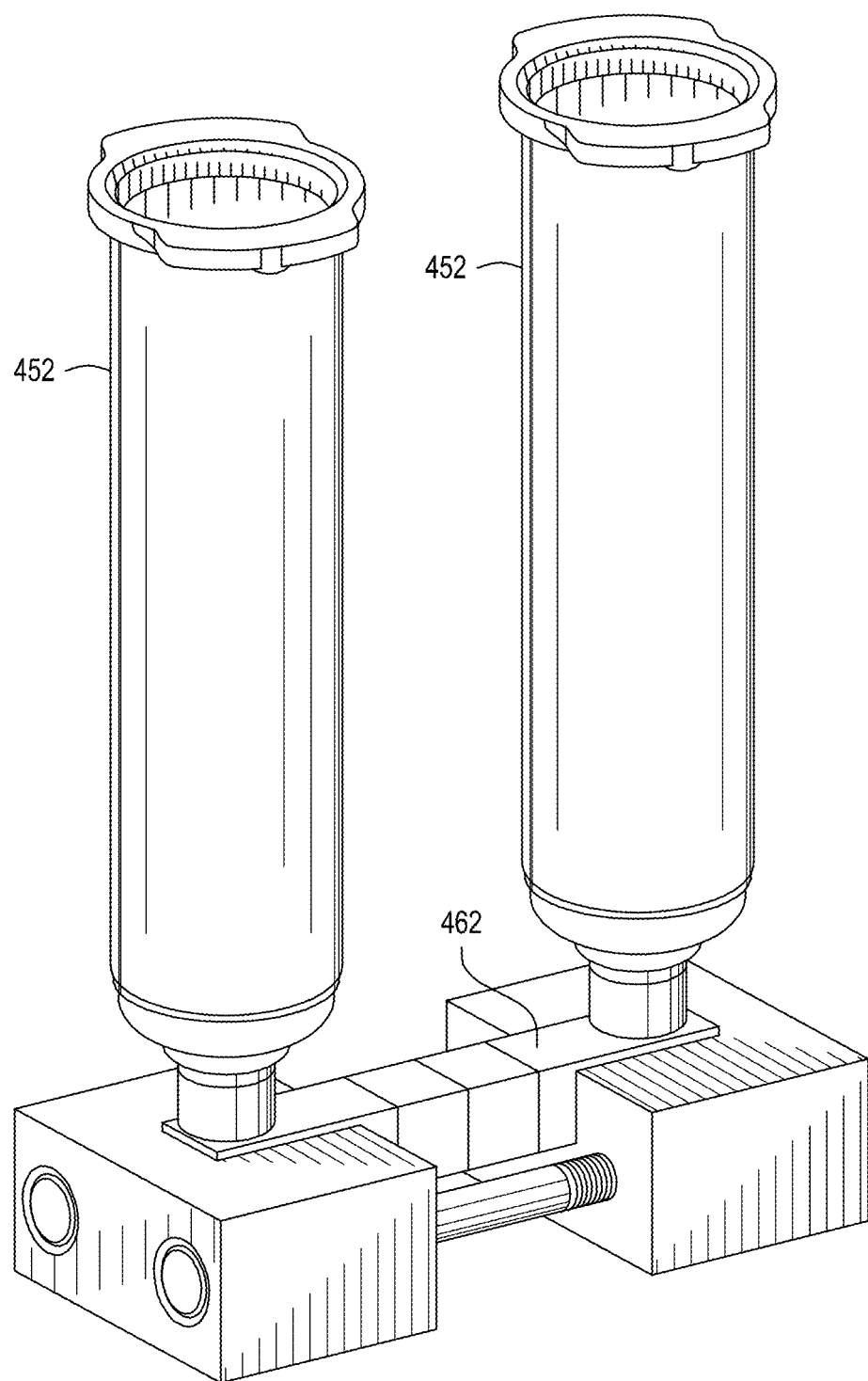
FIGS. 4F and 4G depict a retentate reservoir assembly comprising one or more strainers or sieves which may be used to dissociate cells in the tangential flow filtration module.
Figure 4G:
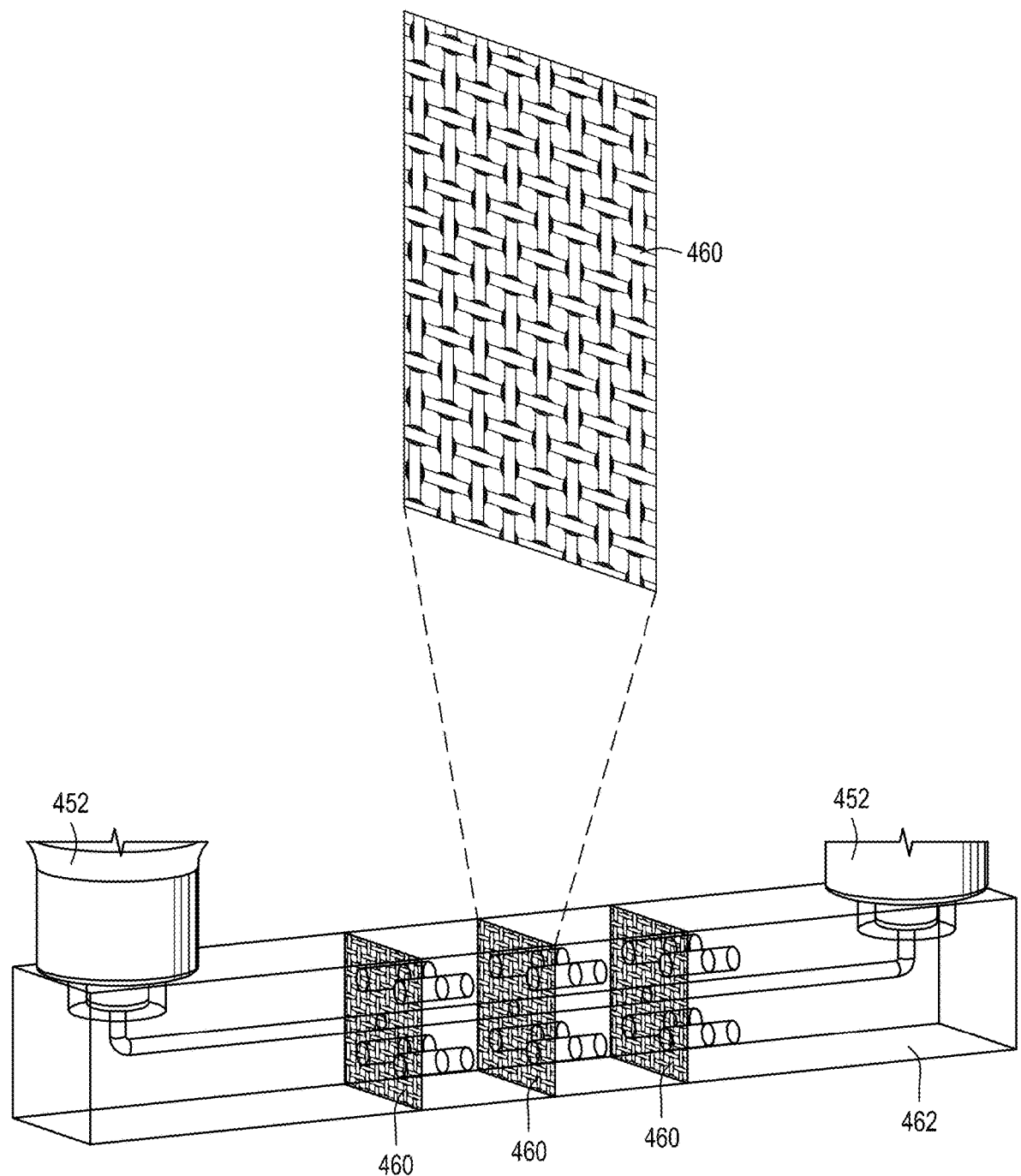

In addition, the TFF module may be modified to dissociate cells, as shown in FIGS. 4F and 4G. That is, the TFF may be modified such that the retentate reservoirs, in addition to being connected through the flow channel that courses through the TFF module, are connected directly by a conduit where the cells are passed from one retentate reservoir to another without being sent through the flow channel. In FIG. 4F, retentate reservoirs 452 are shown, connected by conduit 462. In conduit 462 are placed one to many (e.g., in FIG. 4G, there are three) strainers, frits or sieves 460 through which aggregates of cells are passed to dissociate the aggregates. As with the modified paddles or features in the rotating growth vial, strainers, frits or sieves 460 comprise pores or openings from 10 to 400 microns in size, or from 20 to 200 microns in size, or from 30 to 100 microns in size configured to dissociate the cell aggregates. That is, the TFF may be used to grow the cells—either as aggregates or on microcarriers—passage the cells to increase the number of cells, concentrate the cells and then finally the cells may be routed through the direct conduit between the retentate reservoirs to dissociate the cells for transfection/transduction.

The Bioreactor

In addition to the rotating growth vial module shown in FIGS. 3A-3E and described in the related text, and the tangential flow filtration module shown FIGS. 4A-4G and described in the related text, a bioreactor can be used to grow cells off-instrument or to allow for cell growth and recovery on-instrument; e.g., as one module of the multi-module automated instrument. Further, the bioreactor supports cell selection/enrichment, via expressed antibiotic markers in the growth process or via expressed antibodies coupled to magnetic beads and a magnet associated with the bioreactor. There are many bioreactors known in the art, including those described in, e.g., WO 2019/046766; 10,699,519; 10,633,625; 10,577,576; 10,294,447; 10,240,117; 10,179,898; 10,370,629; and 9,175,259; and those available from Lonza Group Ltd. (Basel, Switzerland); Miltenyi Biotec (Bergisch Gladbach, Germany), Terumo BCT (Lakewood, Colo.) and Sartorius GmbH (Gottingen, Germany).

Figure 5A:
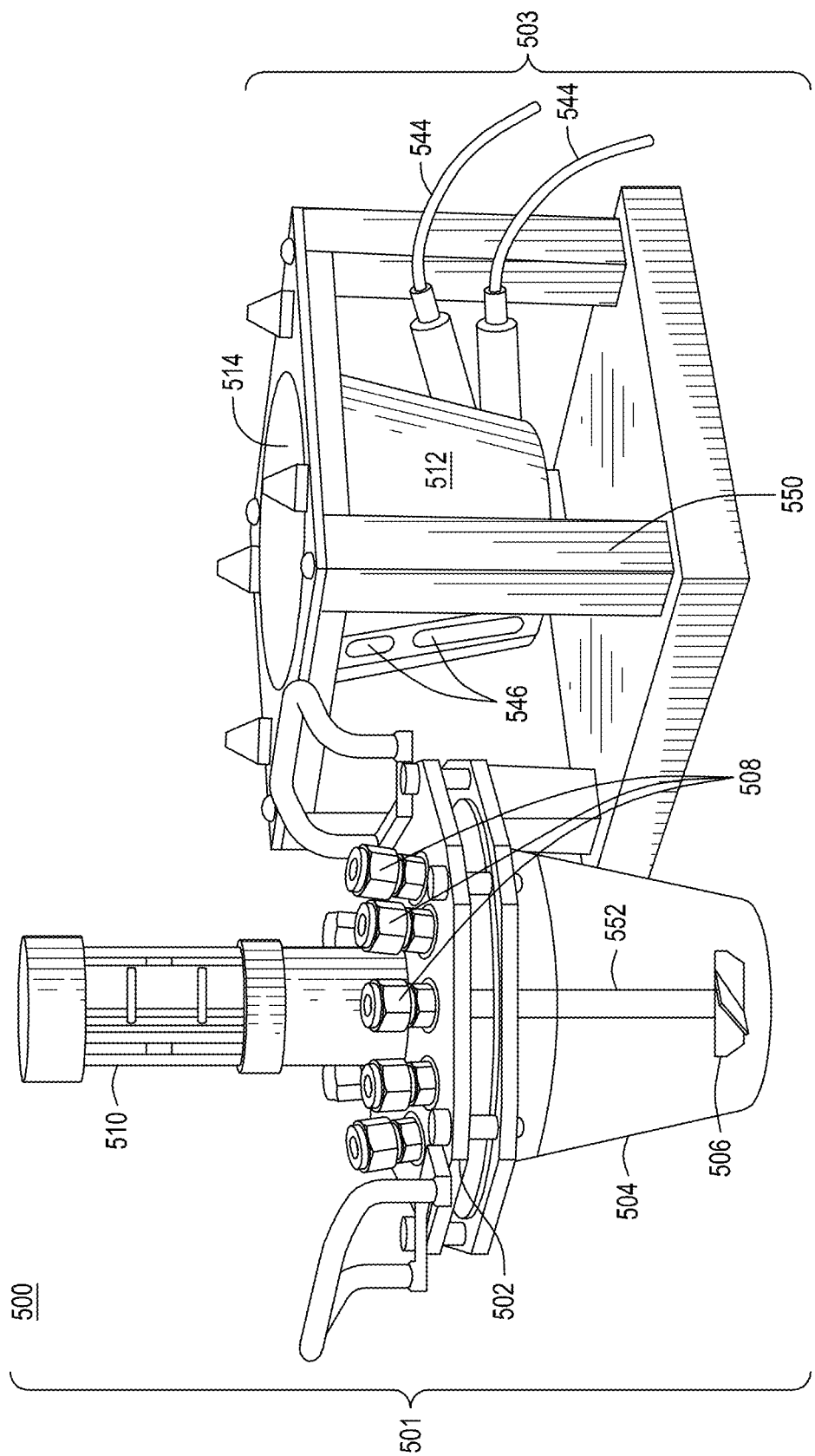
FIGS. 5A-5G depict various components of an embodiment of a bioreactor useful for growing and transducing mammalian cells by the methods described herein.

FIG. 5A shows one embodiment of a bioreactor assembly 500 for cell growth, growth monitoring, transduction, transfection, selection and editing in the automated multi-module cell processing instruments described herein. Unlike most bioreactors that are used to support fermentation or other processes with an eye to harvesting the products produced by organisms grown in the bioreactor, the present bioreactor (and the processes performed therein) is configured to grow cells, monitor cell growth (via, e.g., optical means or capacitance), passage cells, select cells, transfect or transduce cells, and support the editing, expansion and harvesting of edited cells. Bioreactor assembly 500 comprises a growth and transduction/transfection vessel 501 comprising a main body 504 with a lid assembly 502 comprising ports 508, including an optional motor integration port 510 driving impeller 506 via impeller shaft 552. Bioreactor assembly 500 comprises a growth vessel 501 comprising tapered a main body 504 with a lid assembly 502 comprising ports 508, including an optional motor integration port 510 driving impeller 506 via impeller shaft 552. The tapered shape of main body 504 of the vessel 501 along with, in some embodiments, dual impellers allows for working with a larger dynamic range of volumes, such as, e.g., up to 500 ml and as low as 100 ml for rapid sedimentation of the microcarriers. In addition, the low volume is useful for magnetic bead separation or enrichment as described above.

Bioreactor assembly 500 further comprises bioreactor stand assembly 503 comprising a main body 512 and vessel holder 514 comprising a heat jacket or other heating means (not shown, but see FIG. 5E) into which the main body 504 of vessel 501 is disposed in operation. The main body 504 of vessel 501 is biocompatible and preferably transparent—in some embodiments, in the UV and IR range as well as the visible spectrum—so that the growing cells can be visualized by, e.g., cameras or sensors integrated into lid assembly 502 or through viewing apertures or slots in the main body 512 of bioreactor stand assembly 503 (not shown in this FIG. 5A, but see FIG. 5E).

Bioreactor assembly 500 supports growth of cells from a 500,000 cell input to a 10 billion cell output, or from a 1 million cell input to a 25 billion cell output, or from a 5 million cell input to a 50 billion cell output or combinations of these ranges depending on, e.g., the size of main body 504 of vessel 501, the medium used to grow the cells, whether the cells are adherent or non-adherent. The bioreactor that comprises assembly 500 supports growth of both adherent and non-adherent cells, wherein adherent cells are typically grown of microcarriers as described in detail above and supra or as spheroids. Alternatively, another option for growing mammalian cells in the bioreactor described herein is growing single cells in suspension using a specialized medium such as that developed by ACCELLTA™ (Haifa, Israel). As described above, cells grown in this medium must be adapted to this process over many cell passages; however, once adapted the cells can be grown to a density of >40 million cells/ml and expanded 50-100× in approximately a week, depending on cell type.

Main body 504 of vessel 501 preferably is manufactured by injection molding, as is, in some embodiments, impeller 506 and the impeller shaft (not shown). Impeller 506 also may be fabricated from stainless steel, metal, plastics or the polymers listed infra. Injection molding allows for flexibility in size and configuration and also allows for, e.g., volume markings to be added to the main body 504 of vessel 501. Additionally, material from which the main body 504 of vessel 501 is fabricated should be able to be cooled to about 4° C. or lower and heated to about 55° C. or higher to accommodate cell growth. Further, the material that is used to fabricate the vial preferably is able to withstand temperatures up to 55° C. without deformation. Suitable materials for main body 504 of vessel 501 include those described for the rotating growth vial described in relation to FIGS. 3A and 3B and the TFF device described in relation to FIG. 4A-4E, including cyclic olefin copolymer (COC), glass, polyvinyl chloride, polyethylene, polyetheretherketone (PEEK), polypropylene, polycarbonate, poly(methyl methacrylate) (PMMA), polysulfone, poly(dimethylsiloxane), cyclo-olefin polymer (COP), and co-polymers of these and other polymers. Preferred materials include polypropylene, polycarbonate, or polystyrene. The material used for fabrication may depend on the cell type to be grown, transduced and transfected, and is conducive to growth of both adherent and non-adherent cells and to workflows involving microcarrier-based growth, viral transduction and transfection. The main body 504 of vessel 501 may be reusable or, alternatively, may be manufactured and configured for a single use. In one embodiment, main body 504 of vessel 501 may support cell culture volumes of 25 ml to 500 ml, but may be scaled up to support cell culture volumes of up to 3 L.

The bioreactor stand assembly comprises a stand or frame 550, a main body 512 which holds the vessel 501 during operation. The stand/frame 550 and main body 512 are fabricated from stainless steel, other metals, or polymer/plastics. The bioreactor main body further comprises a heat jacket (not seen in FIG. 5A, but see FIG. 5E) to maintain the bioreactor main body 504—and thus the cell culture—at a desired temperature. Essentially, the stand assembly can host a set of sensors and cameras to monitor cell culture.

Figure 5B:
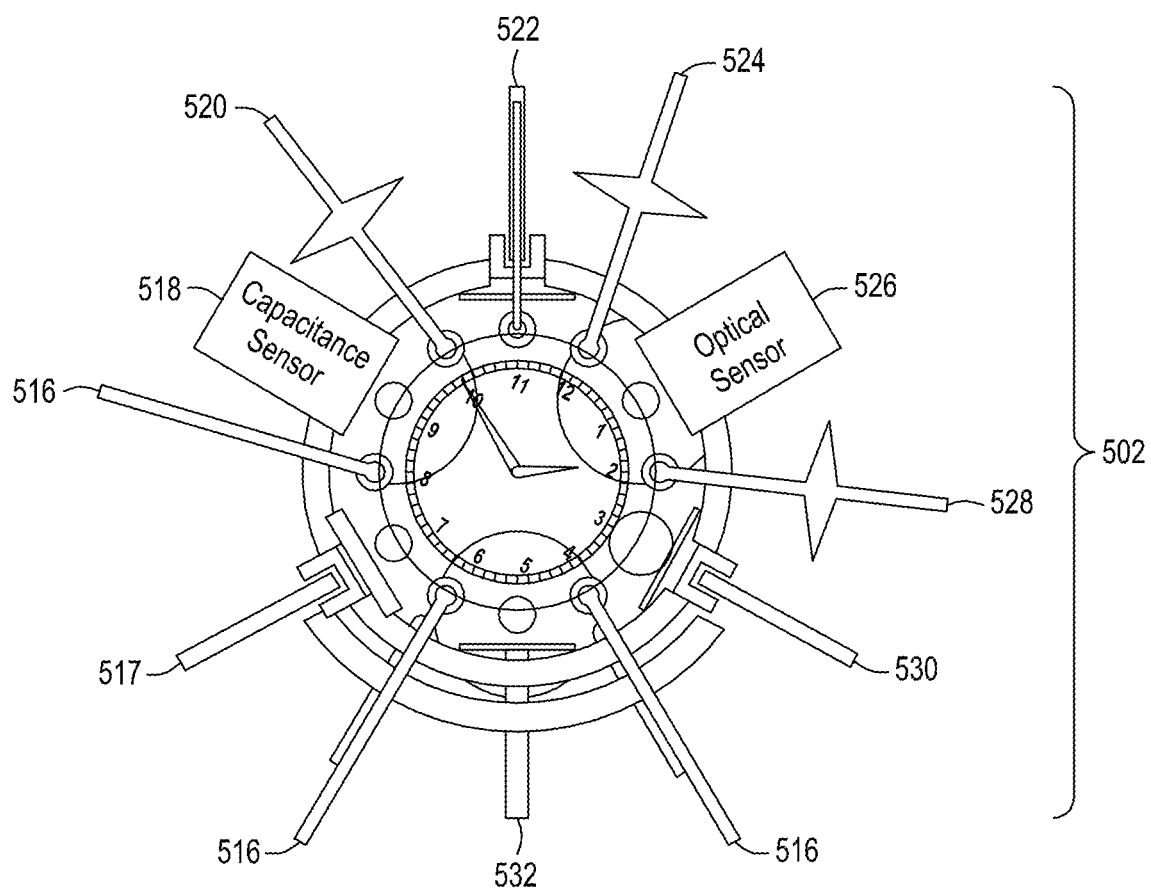

FIG. 5B depicts a top-down view of one embodiment of vessel lid assembly 502. Vessel lid assembly 502 is configured to be air-tight, providing a sealed, sterile environment for cell growth, transduction, selection, transfection and editing as well as to provide biosafety, particularly when conducting viral transduction by maintaining a closed system. Vessel lid assembly 502 and the main body 504 of vessel 501 can be sealed via fasteners such as screws, using biocompatible glues, or the two components may be ultrasonically welded. Vessel lid assembly 502 is some embodiments is fabricated from stainless steel such as S316L stainless steel but may also be fabricated from metals, other polymers (such as those listed supra) or plastics. As seen in this FIG. 5B—as well as in FIG. 5A—vessel lid assembly 502 comprises a number of different ports to accommodate liquid addition and removal; gas addition and removal; for insertion of sensors to monitor culture parameters (described in more detail infra); to accommodate one or more cameras or other optical sensors; to provide access to the main body 504 of vessel 501 by, e.g., a liquid handling device; and to accommodate a motor for motor integration to drive one or more impellers 506. Exemplary ports depicted in FIG. 5B include three liquid-in ports 516 (at 4 o'clock, 6 o'clock and 8 o'clock), one liquid-out port 522 (at 11 o'clock), a capacitance sensor 518 (at 9 o'clock), one "gas in" port 524 (at 12 o'clock), one "gas out" port 520 (at 10 o'clock), an optical sensor 526 (at 1 o'clock), a rupture disc 528 at 2 o'clock, a self-sealing port 530 (at 3 o'clock) to provide access to the main body 504 of growth vessel 501; and (a temperature probe 532 (at 5 o'clock).

The ports 508 shown in vessel lid assembly 502 in this FIG. 5B are exemplary only and it should be apparent to one of ordinary skill in the art given the present disclosure that, e.g., a single liquid-in port 516 could be used to accommodate addition of all liquids to the cell culture rather than having a liquid-in port for each different liquid added to the cell culture. Similarly, there may be more than one gas-in port 524, such as one for each gas, e.g., $O_2$, $CO_2$ that may be added. In addition, although a temperature probe 532 is shown, a temperature probe alternatively may be located on the outside of vessel holder 514 of bioreactor stand assembly 503 separate from or integrated into heater jacket 548 (not seen in this FIG. 5B, but see FIG. 5E). A self-sealing port 530, if present, allows access to the main body 504 of vessel 501 for, e.g., a pipette, syringe, or other liquid delivery system via a gantry (not shown). As shown in FIG. 5A, additionally there may be a motor integration port to drive the impeller(s), although in other configurations of vessel 501 may alternatively integrate the motor drive at the bottom of the main body 504 of vessel 501. Vessel lid assembly 502 may also comprise a camera port for viewing and monitoring the cells.

Additional sensors include those that detect $O_2$ concentration, a $CO_2$ concentration, culture pH, lactate concentration, glucose concentration, biomass, and optical density. The sensors may use optical (e.g., fluorescence detection), electrochemical, or capacitance sensing and either be reusable or configured and fabricated for single use. Sensors appropriate for use in the bioreactor are available from Omega Engineering (Norwalk CT); PreSens Precision Sensing (Regensburg, Germany); C-CIT Sensors AG (Waedenswil, Switzerland), and ABER Instruments Ltd. (Alexandria, Va.). In one embodiment, optical density is measured using a reflective optical density sensor to facilitate sterilization, improve dynamic range and simplify mechanical assembly. The rupture disc, if present, provides safety in a pressurized environment, and is programmed to rupture if a threshold pressure is exceeded in the bioreactor. If the cell culture in the bioreactor vessel is a culture of adherent cells, microcarriers may be used as described supra. In such an instance, the liquid-out port may comprise a filter such as a stainless steel or plastic (e.g., polyvinylidene difluoride (PVDF), nylon, polypropylene, polybutylene, acetal, polyethylene, or polyamide) filter or frit to prevent microcarriers from being drawn out of the culture during, e.g., medium exchange, but to allow dead cells to be withdrawn from the vessel.

As described supra, the microcarriers used for initial cell growth can be nanoporous (where pore sizes are typically <20 nm in size), microporous (with pores between >20 nm to <1 μm in size), or macroporous (with pores between >1 μm in size, e.g. 20 μm) and the microcarriers are typically 50-200 μm in diameter; thus the pore size of the filter or frit in the liquid-out port will differ depending on microcarrier size. The microcarriers used for cell growth depend on cell type and desired cell numbers, and typically include a coating of a natural or synthetic extracellular matrix or cell adhesion promoters (e.g., antibodies to cell surface proteins or poly-L-lysine) to promote cell growth and adherence. Microcarriers for cell culture are widely commercially available from, e.g., Millipore Sigma, (St. Louis, Mo., USA); ThermoFisher Scientific (Waltham, Mass., USA); Pall Corp. (Port Washington, N.Y., USA); GE Life Sciences (Marlborough, Mass., USA); and Corning Life Sciences (Tewkesbury, Mass., USA). As for the extracellular matrix, natural matrices include collagen, fibrin and vitronectin (available, e.g., from ESBio, Alameda, Calif., USA), and synthetic matrices include MATRIGEL® (Corning Life Sciences, Tewkesbury, Mass., USA), GELTREX™ (ThermoFisher Scientific, Waltham, Mass., USA), CULTREX® (Trevigen, Gaithersburg, Md., USA), biometic hydrogels available from Cellendes (Tubingen, Germany); and tissue-specific extracellular matrices available from Xylyx (Brooklyn, N.Y., USA); further, denovoMatrix (Dresden, Germany) offers screenMATRIX™, a tool that facilitates rapid testing of a large variety of cell microenvironments (e.g., extracellular matrices) for optimizing growth of the cells of interest.

Figure 5C:
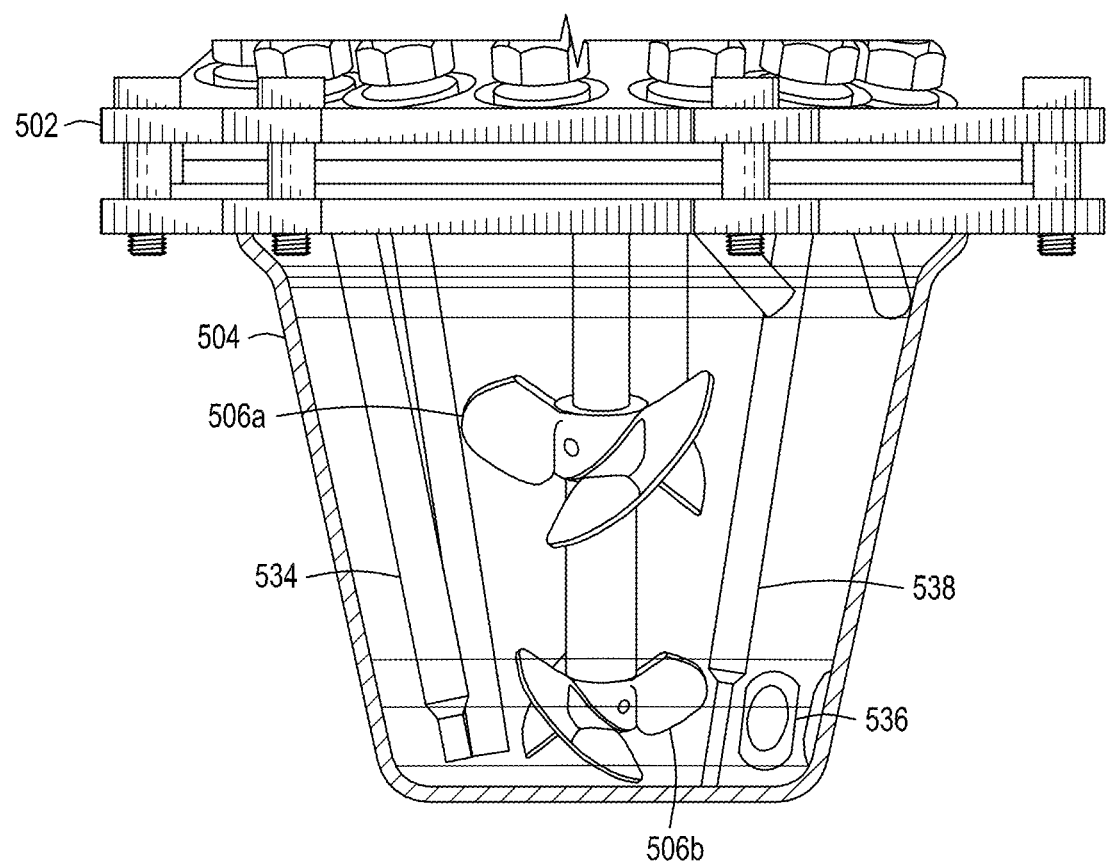

FIG. 5C is a side view of the main body 504 of vessel 501. A portion of vessel lid assembly 502 can be seen, as well as two impellers 506a and 506b. Also seen are a lactate/glucose sensor probe 534, a pH, $O_2$, $CO_2$ sensor 536 (such as a PRESENS™ integrated optical sensor (Precision Sensing GmbH, (Regensburg, Germany)), and a viable biomass sensor 538 (such as, e.g., the FUTURA PICO™ capacitance sensor (ABER, Alexandria Va.)). In some embodiments, flat regions are fabricated onto the main body 504 of vessel 501 to reduce optical loss, simplify spot placement and simplify fluorescent measurement of pH, $dO_2$, and $dCO_2$.

Figure 5D:
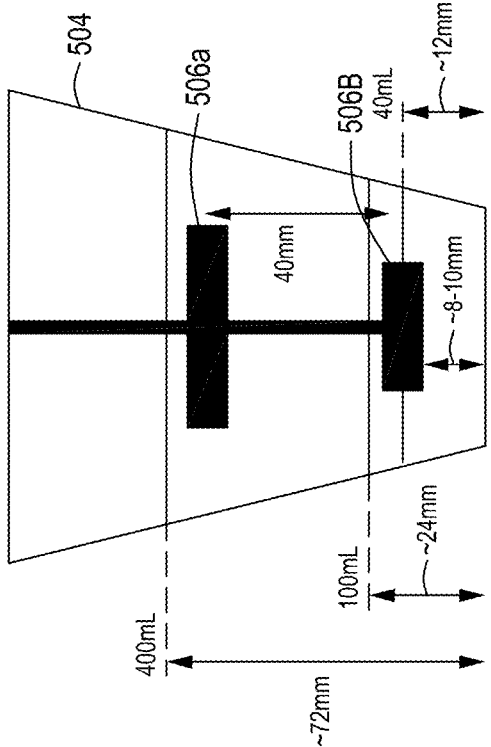
Figure 5D:
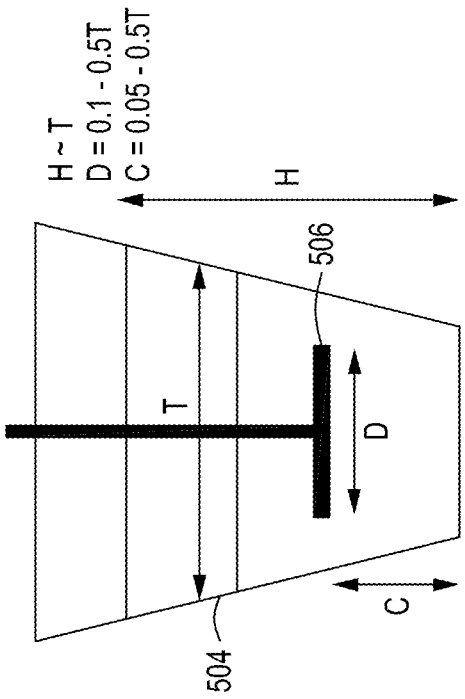
Figure 5D:
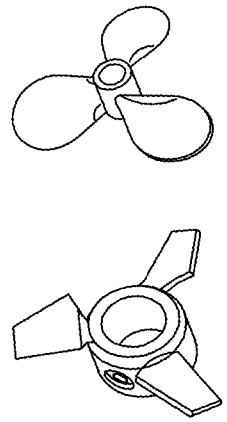
Figure 5D:

FIG. 5D shows exemplary design guidelines for a one-impeller embodiment (left) and a two-impeller embodiment (right) of the main body 504 of vessel 501, including four exemplary impeller configurations. The embodiment of the INSCRIPTA™ bioreactor vessel 501 main body 504 as shown in this FIG. 5D has a total volume of 820 ml and supports culture volumes from 25 ml to 500 ml. As mentioned above, the impellers (and impeller shaft) may be injection molded or may be fabricated from stainless steel, other biocompatible metals, polymers or plastics and preferably comprised polished surfaces to facilitate sterilization. The impeller may be configured as a turbine-, pitched-blade-, hydrofoil- or marine-type impeller. In a two-impeller configuration, the impellers may be of the same type or different types. In the bioreactors described herein (the "INSCRIPTA™ bioreactors") and used to generated the data in Examples IV-XI, agitation is provided at 0-100 rpm, or 40-80 rpm, or approximately 70 rpm during cell growth (depending on the cell type being cultured); however, lower or higher revolutions per minute may be used depending on the volume of the main body 504 of vessel 501, the type of cells being cultured, whether the cells are adherent and being grown on microcarriers or the cells are non-adherent, and the size and configuration of the impellers. The impeller may turn in a clockwise direction, a counter-clockwise direction or the impeller may change direction (oscillate) or stop at desired intervals, particularly during cell detachment from the microcarriers. Also, intermittent agitation may be applied, e.g., agitating for 10 minutes every 30 minutes, or agitating for 1 minute every 5 minutes or any other desired pattern. Additionally, impeller rpm is often increased (e.g., up to 4000 rpm) when the cells are being detached from microcarriers. Although the present embodiment of INSCRIPTA™ bioreactor utilizes one or more impellers for cell growth, alternative embodiments of the INSCRIPTA™ bioreactor described herein may utilize bubbling or other physical mixing means.

Also seen in FIG. 5D is an equation that gives a range for exemplary bioreactor dimensions base on the height (H) and thickness (T) of the main body of vessel 504. For example, D=0.25–05*T means the impeller diameter could be one quarter or one half of the main body of vessel 504 thickness, T. C is the clearance of the impeller from the bottom of the main body of vessel 504, which can be 0.15 to 0.5 times the thickness. It should be apparent to one of ordinary skill in the art given the present disclosure that these numbers are just one embodiment and the ranges may be larger. The bioreactor vessel 501 main body 504 comprises an 8-10 mm clearance from the bottom of the main body 504 of vessel 501 to the lower impeller 506b and the lower impeller 506 and the upper impeller 506a are approximately 40 mm apart.

Figure 5E:
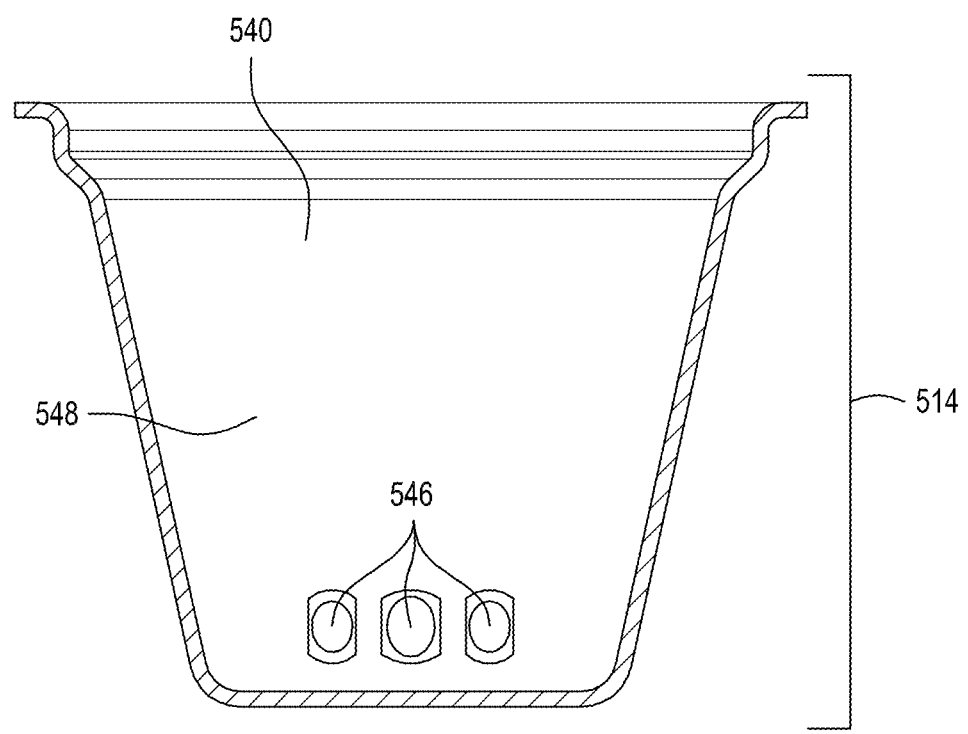
Figure 5F:
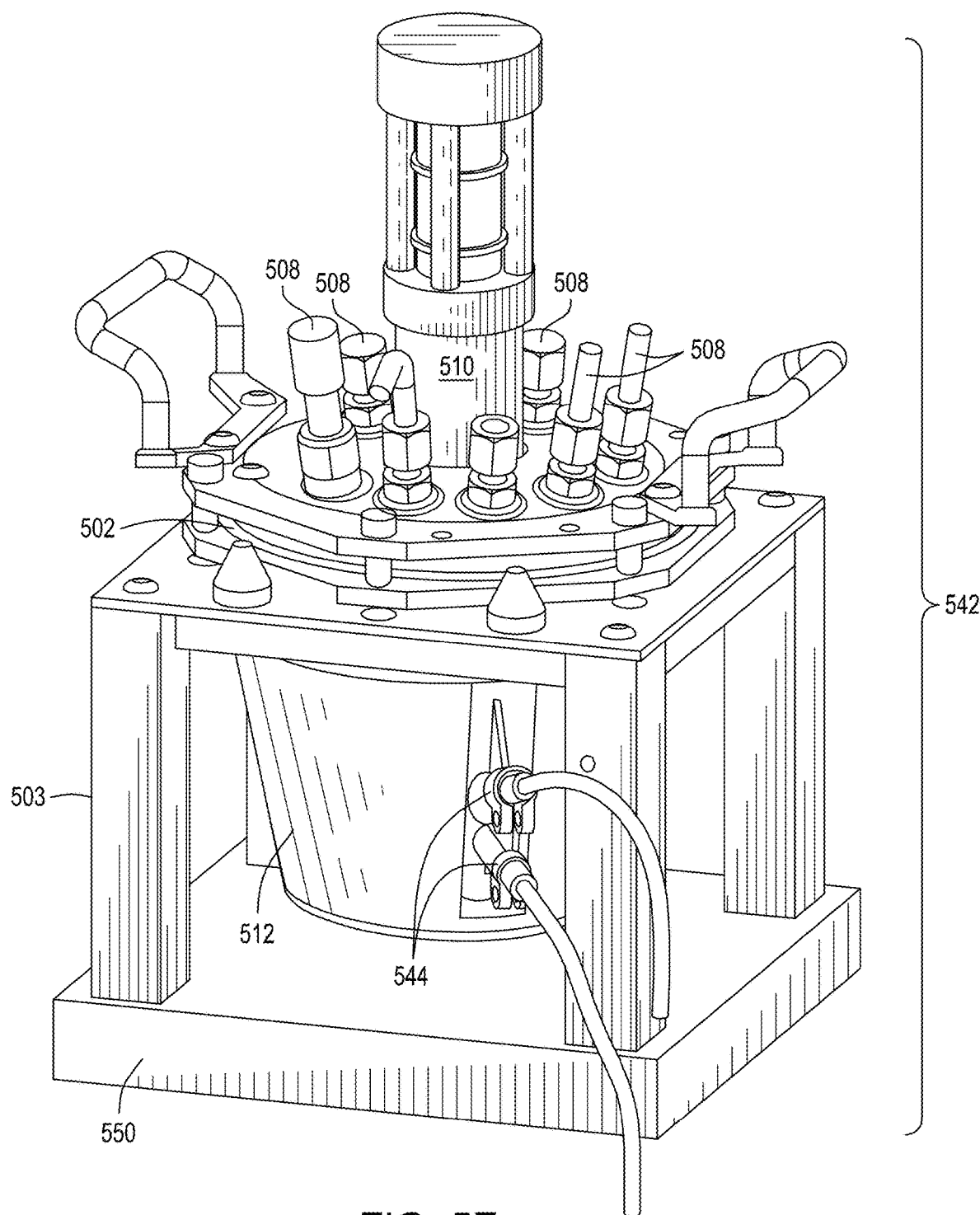
Figure 5G:
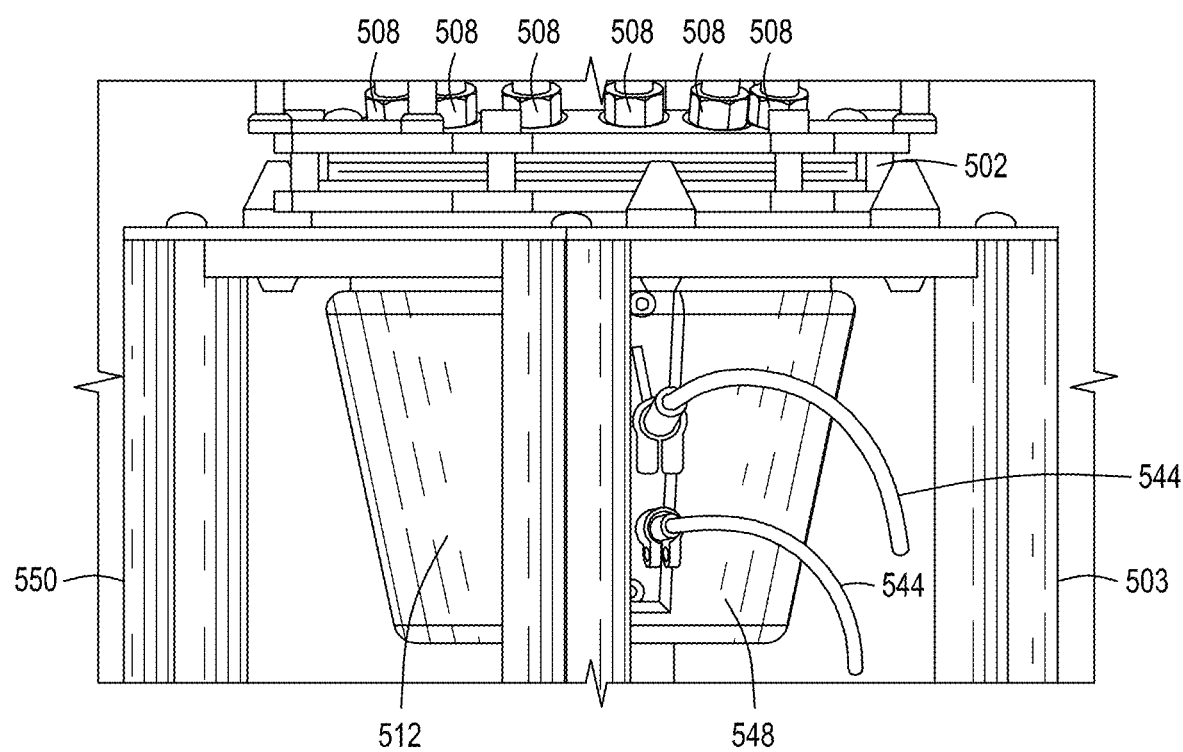

FIG. 5E is a side view of the vessel holder portion 514 of the bioreactor stand main body 512 of the bioreactor stand assembly 503. Inner surface 540 of vessel holder 514 is indicated and shown are camera or fiber optic ports 546 for monitoring, e.g., cell growth and viability; $O_2$ and $CO_2$ levels, and pH. The vessel holder portion 514 of the bioreactor stand main body 512 may also provide illumination using LED lights, such as a ring of LED lights (not shown). FIG. 5F is a side perspective view of the assembled bioreactor without sensors 542. Seen are vessel lid assembly 502, bioreactor stand assembly 503, bioreactor stand main body 512 into which the main body 504 of vessel 501 (not seen in FIG. 5E) is inserted. FIG. 5G is a lower side perspective view of bioreactor assembly 500 showing bioreactor stand assembly 503, bioreactor stand main body 512, vessel lid assembly 502 and two camera mounts 544. Surrounding bioreactor stand main body 512 is heater jacket 548.

Figures 2, 5H:
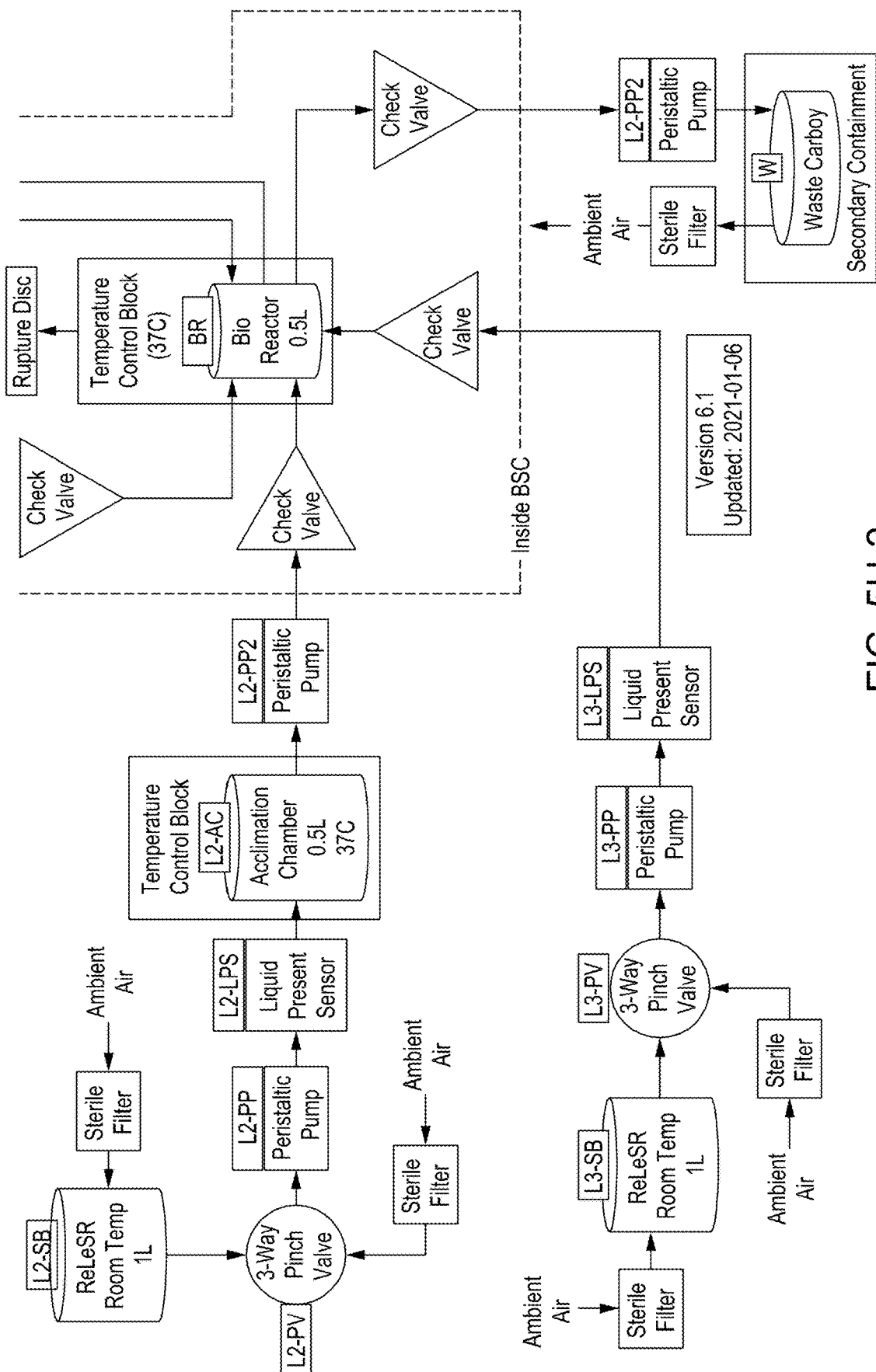

FIG. 5H is an exemplary diagram of the bioreactor fluidics. Fluidics and pneumatics are designed to establish a cell culture environment conducive for mammalian cell growth, including iPSCs. Fluidic circuits are designed to deliver and/or remove cell medium, buffers, microcarriers and additional reagents needed for growth, maintenance, selection and passaging of the cells in the automated closed culture instrument. The pneumatic circuits are designed to deliver the appropriate gas mixture and humidity for the chosen cell type, and may comprise line-in filters to prevent any contaminants from reaching the bioreactor.

Figure 5I:
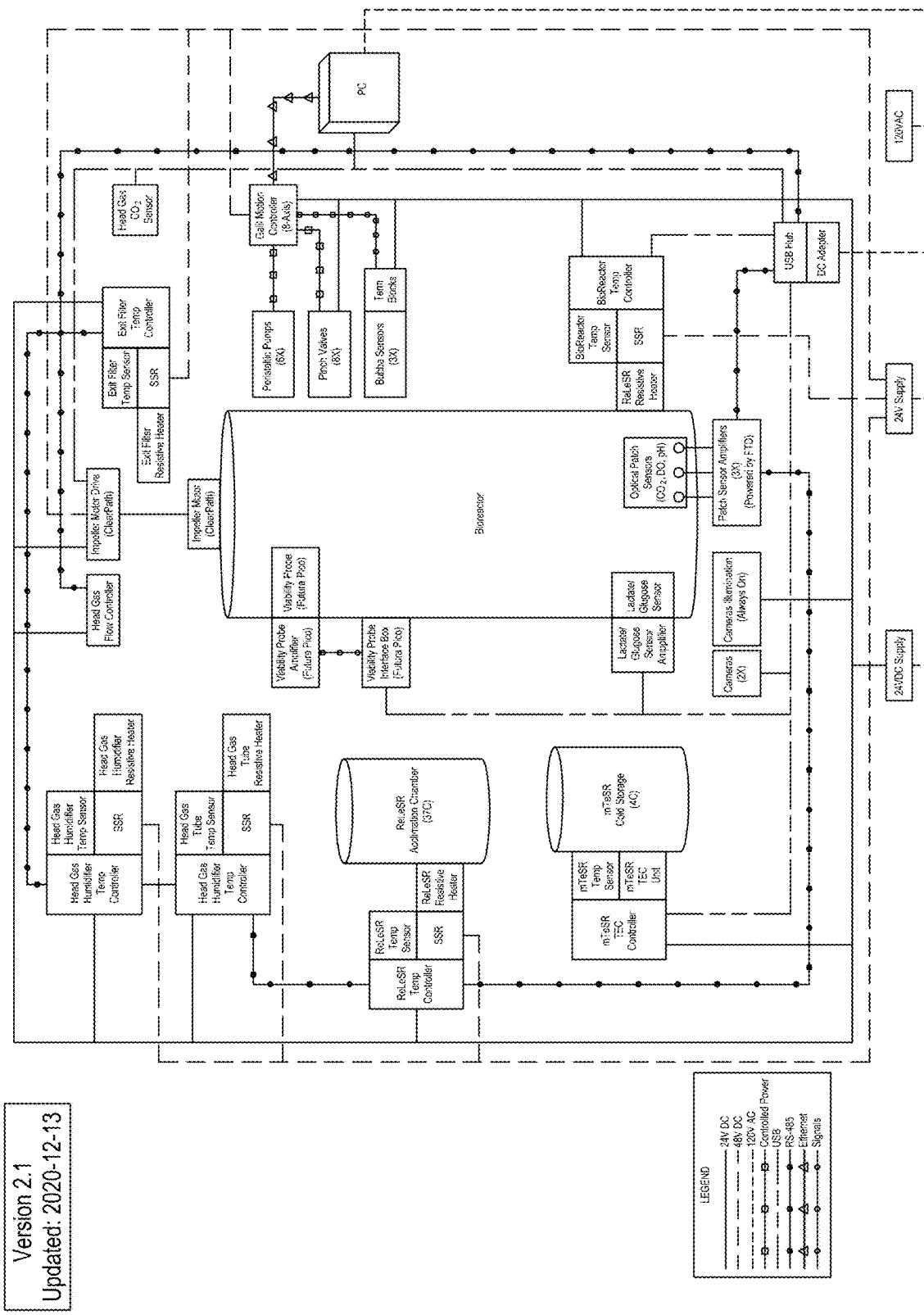
FIG. 5I depicts an exemplary control system block diagram for the bioreactor described in relation to FIGS. 5A-5G.

FIG. 5I is a block diagram for an exemplary bioreactor control system. The control system is designed to control and automate the fluidics, pneumatics and sensor function in a closed system and without human intervention. In one embodiment, the control system is based on state-machines with a user editable state order and parameters using Json and jsonette config files. State-machines allow for dynamic control of several aspects of the bioreactor with a single computer.

In use, the bioreactor described herein is used for cell growth and expansion—either before or after the cells are transfected in droplets—as well as for medium exchange and cell concentration. Medium/buffer exchange is in one embodiment accomplished using gravitational sedimentation and aspiration via a filter in the liquid-out port where the filter is of an appropriate size to retain microcarriers (see, e.g., Example VII, infra). In one embodiment used with the present bioreactor, a frit with pore size 100 was used and microcarriers with diameters of 120-225 were used in the cell culture. Sedimentation was accomplished in approximately 2-3 minutes for a 100 ml culture and 4-5 minutes for a 500 ml culture. The medium was aspirated at >100 ml/min rate. In addition to clearing the medium from the main body 504 of vessel 501, dead cells were removed as well. If sedimentation is used, the microcarriers do not typically accumulate on the filter; however, if accumulation is detected, the medium in the liquid-out port can be pushed back into main body 504 of vessel 501 in a pulse. In some embodiments—particularly those where sedimentation is not used—a cycle of aspiration, release (push back), aspiration and release (push back) may be performed. Experimental results show that medium exchange (aspiration) at ~200 ml/min does not impact cell growth (see FIG. 13).

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example I

Viral Editing in HEK Cells

Figure 6:
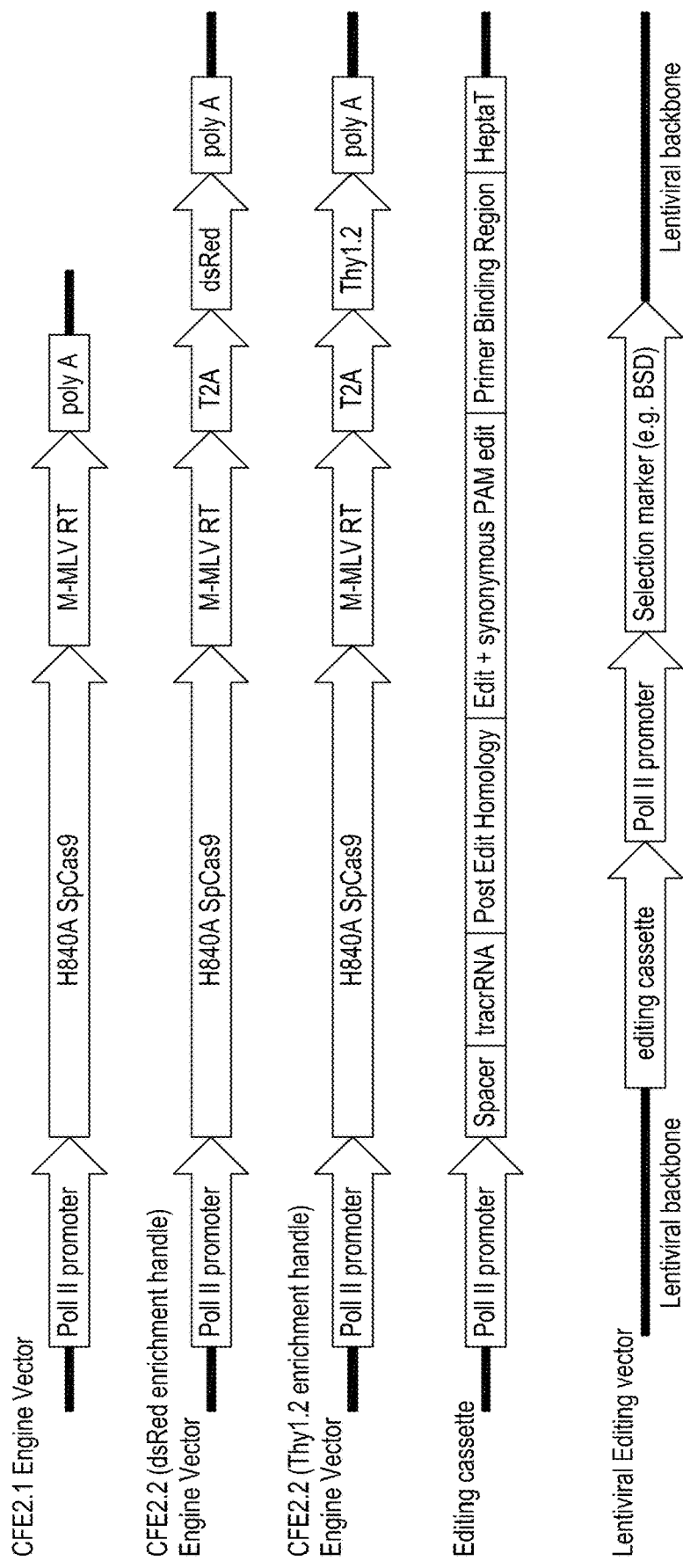
FIG. 6 shows exemplary vector maps for engine vector, editing cassette and editing vector constructs used in viral delivery experiments.

The constructs used for viral delivery experiments are shown in FIG. 6. CREATE Fusion Editing (CFE) plasmids contain the SpCas9 nickase fused to M-MLV Reverse transcriptase (RT) followed by a T2A self-cleaving peptide and an enrichment handle. The enrichment handle can be a fluorescent marker (e.g., dsRed) or a cell receptor (e.g., Thy1.2). Fluorescent markers are compatible with cell sorting whereas cell surface receptors are compatible with cell sorting and magnetic enrichment of cells.

The editing cassette, which can be ordered as an oligo, contains a U6 promoter followed by the gRNA (20 nt spacer and 76 nt tracrRNA) and a 3' extension of the gRNA. The extensions contain the post-edit homology region, the donor DNA, a synonymous PAM change and a primer binding region. The Lentiviral plasmid that the editing cassette is cloned into also contains a Pol II promoter-driven selection marker of interest e.g., blasticidin.

Figure 7A:
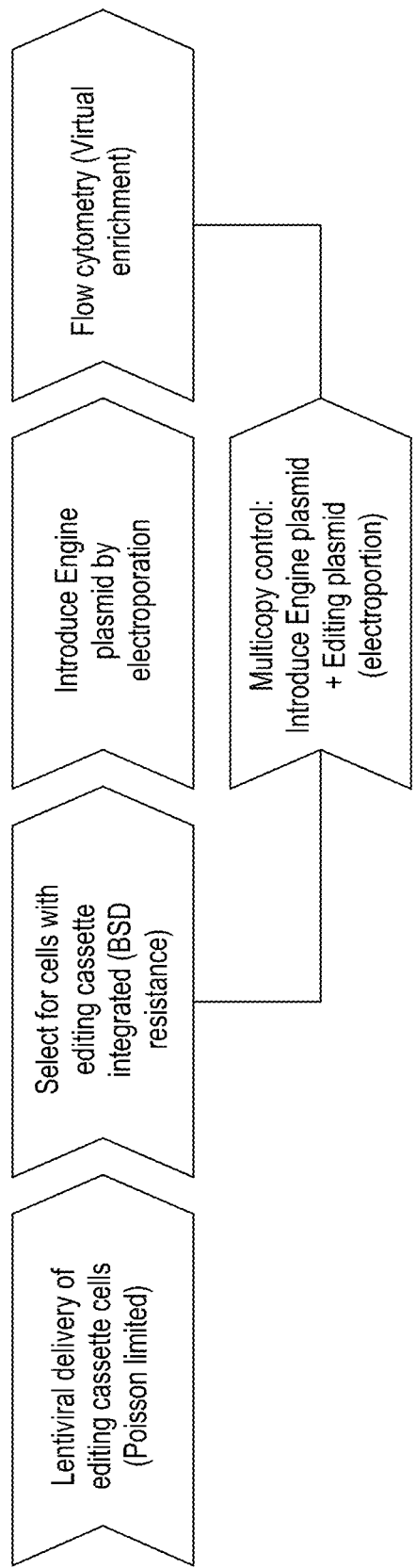
FIG. 7A depicts the workflow for a GFP to BFP proof of concept experiment for viral delivery of editing cassettes.

FIG. 7A shows the workflow of a GFP-to-BFP proof-of-concept experiment for viral delivery of the viral editing cassette vector. The GFP gRNA was cloned into a lentiviral backbone containing a PGK promoter-driven BSD selection marker. This plasmid was used to produce lentivirus in HEK293T cells. Briefly, 1000 ng of Lentiviral transfer plasmid containing the editing cassette along with 1500 ng of Lentiviral Packaging plasmids (ViraSafe Lentivirus Packaging System, Cell BioLabs) were transfected into HEK293T cells using Lipofectamine LTX in 6-well plates. Media containing the lentivirus was collected 72 hrs post transfection.

The resulting lentivirus was used to transduce HEK293T-GFP cells at an MOI of <0.1. Briefly, the day before transduction, 200,000 HEK293T cells were seeded in six well plates. Different volumes of editing cassette lentivirus (10 to 1000 µL) were added to HEK293T cells in six well plates along with 10 µg/mL of Polybrene. Forty-eight hours after transduction, media with 15 µg/mL of Blasticidin was added to the wells. The cells were maintained in selection for one week. Following selection, the well with lowest number of surviving cells was selected. After selection, CFE plasmid (e.g., the engine plasmid) was electroporated into cells using the Neon transfection system. Briefly, 400 ng of total plasmid DNA was mixed with 100,000 cells in Buffer R in a total of 15 µL volume. A 10 µL Neon tip was used to electroporate cells using 2 pulses of 20 ms and 1150 v. Cells were analyzed on the flow cytometer four days after transfection. Virtual enrichment of dsRed (or RFP+) positive cells was performed during the analysis.

Figure 7C:
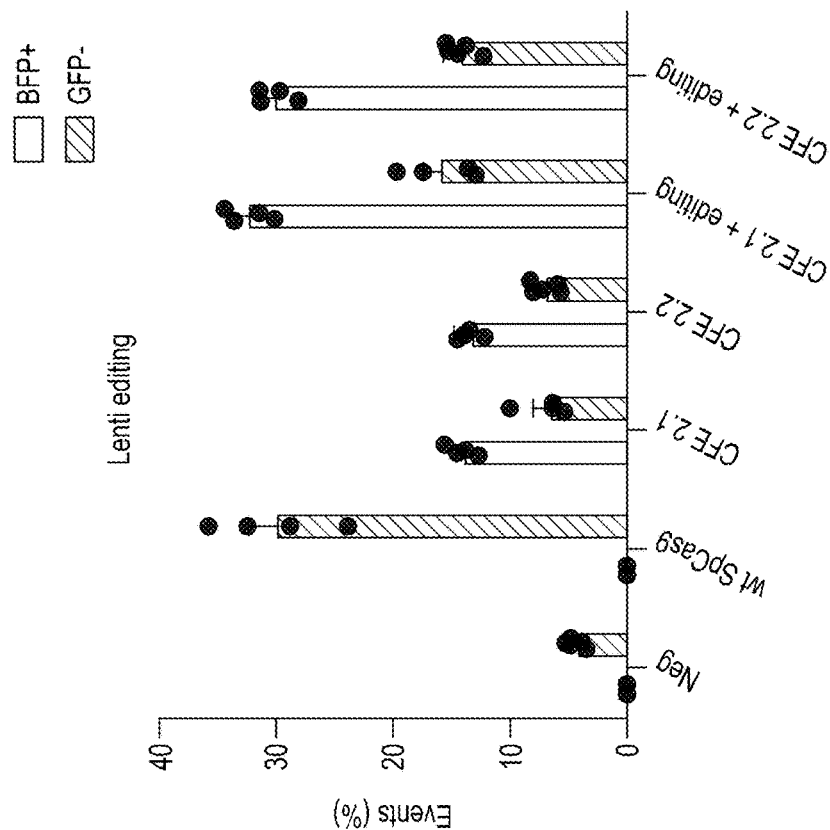
FIGS. 7B, 7C and 7D are three bar graphs showing the results obtained for unenriched editing rates in the GFP to BFP system.
Figure 7B:
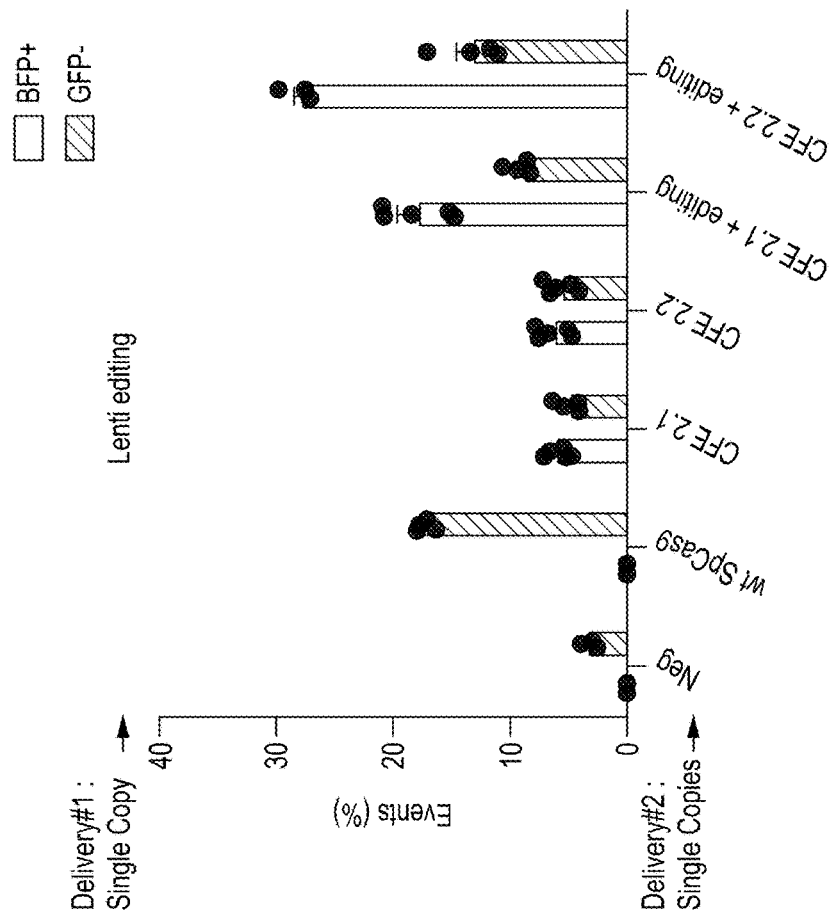
Figure 7D:
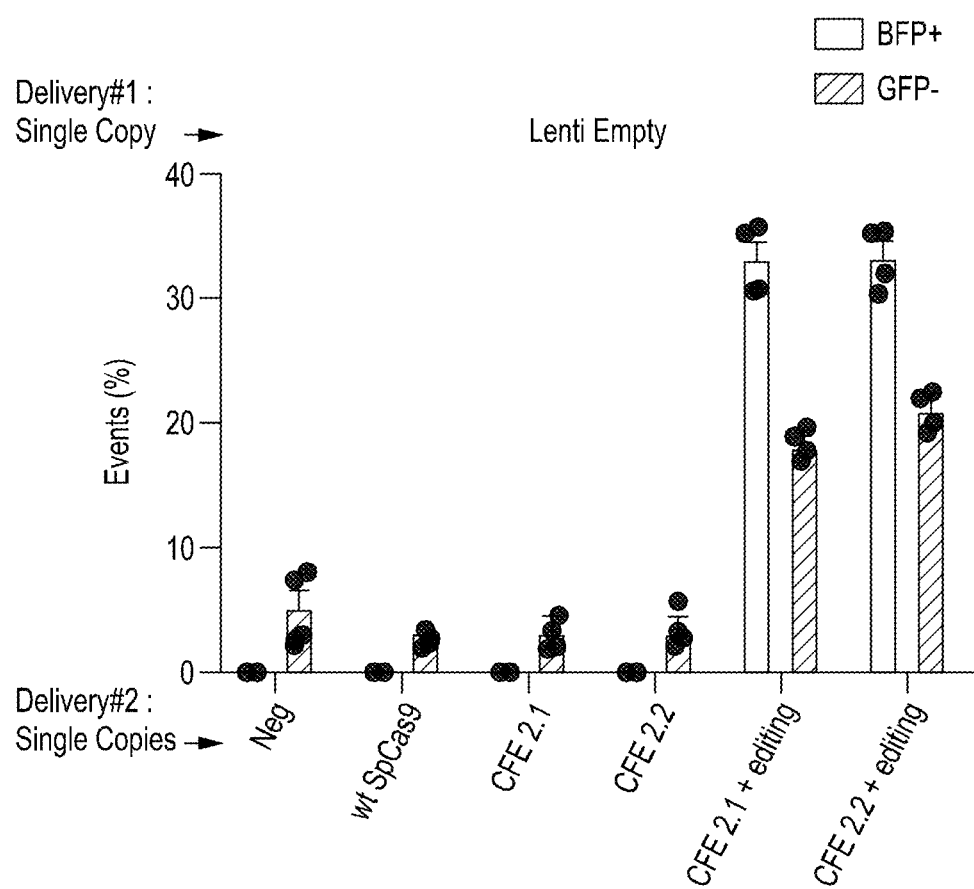
Figures 7E, 7F:
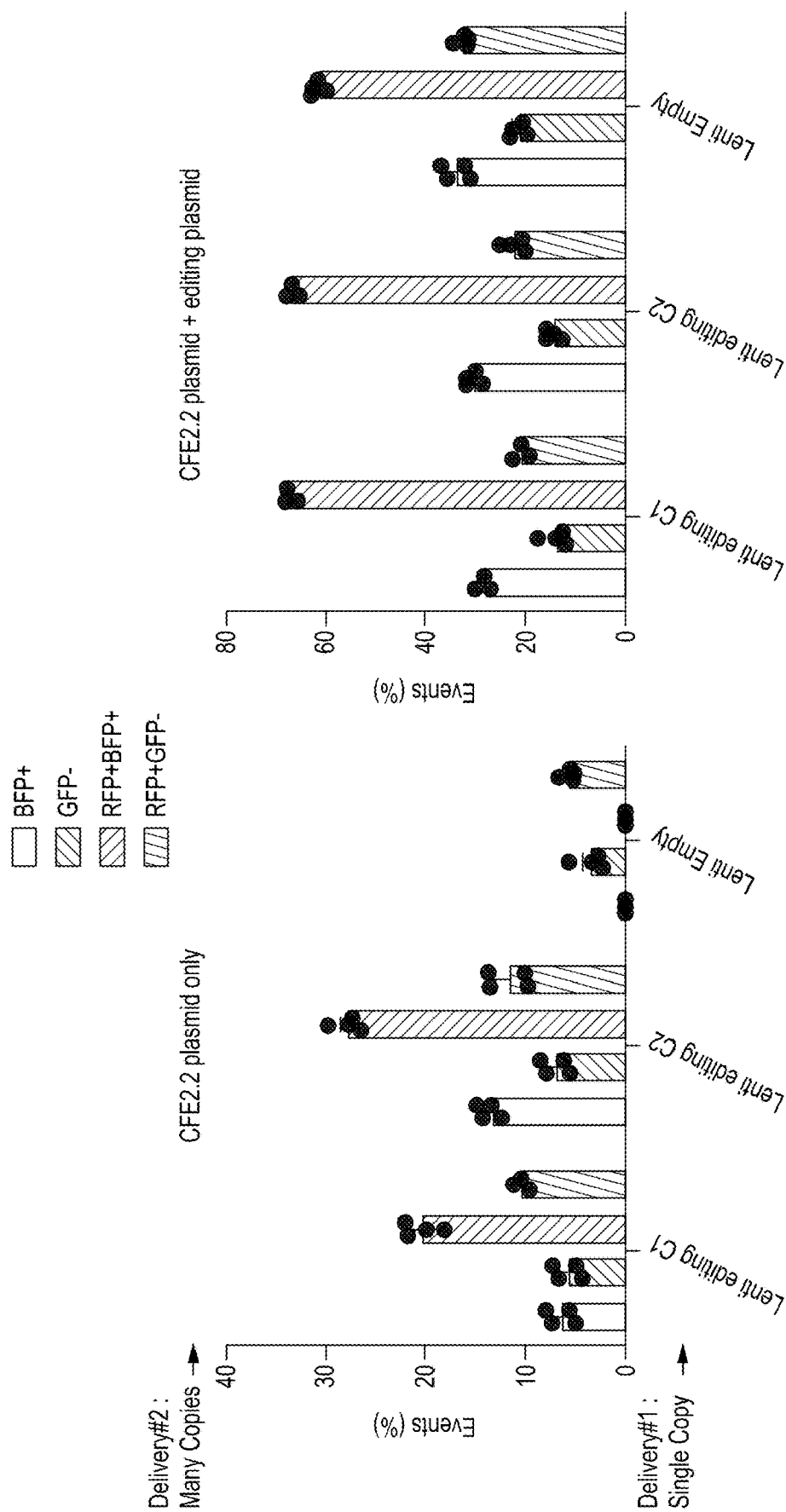
FIGS. 7E and 7F show in two bar graphs the results obtained for enriched editing rates in the GFP to BFP system.

FIGS. 7B, 7C, and 7D show the unenriched editing rates in the GFP-to-BFP system. Two GFP gRNA clones were used as biological replicates for lentiviral delivery. An empty gRNA backbone was used as a negative control. The cells were analyzed on a flow cytometer 96 hrs post transfection. >1000 single cells were collected for each well. The cells were then analyzed to reveal the proportion of cells that were RFP+, BFP+(edited cells), GFP-(imprecisely edited cells). The RFP+cells, which represent the cells that express engine plasmid at the 96-hour time point, were further analyzed to reveal enriched editing rates (RFP+BFP+, RFP+GFP-). Single copy viral delivery of gRNA resulted in editing rates of 5-13% with less than 5% indels. However, the corresponding plasmid delivery of gRNA results in editing rates of ~30-35% suggesting single copy delivery of gRNA results in 3-fold lower editing rates relative to partitioned plasmid delivery. WT SpCas9 results in 20-30% indels and less than 1% editing. FIGS. 7E and 7F shows the enriched editing rates in the GFP-to-BFP system. Single copy viral delivery of gRNA results in enriched editing rates of 20-30% which is an increase of 3-4 fold relative to unenriched editing rates. The corresponding plasmid delivery of gRNA still gives 2-3-fold higher editing.

In a workflow comprising editing at endogenous target sites using lentiviral delivery of gRNAs, the gRNAs were cloned into a lentiviral backbone containing a PGK promoter-driven BSD selection marker. These plasmids were used to produce lentivirus in HEK293T cells, as described above. The resulting lentivirus was used to transduce HEK293T cells at an MOI of <0.1. Successfully transduced cells were selected for the integrated GFP gRNA by selecting for blasticidin resistance. After selection, an engine plasmid was transfected into cells using the PolyFect. Briefly, reverse transfections were performed by mixing 100 ng of plasmid, 25 µL of OptiMeM media, 1 µL of PolyFect (Qiagen, Hilden, Germany) and 20,000 HEK293T in 100 uL of DMEM complete media. Ninety-six hours after transfection, cells were lysed and prepared for amplicon sequencing. Amplicon sequencing was performed 96 hours post transfection. The cells were lysed by incubating at 56° C. with 1 µg/mL Proteinase K for 30 minutes followed by incubation at 90° C. for 10 minutes. 1 µL of the resulting lysate was used as a template to amplify 150 bp amplicons with 2× Hot Start Q5 mastermix (NEB, Ipswich, Mass. USA). A second PCR was performed to add sequencing barcodes and adapters. The wells were then pooled, and size selected by gel purification. The library was then sequenced by NextSeq. The sequencing data was then analyzed using Inscripta's Amplicon Analysis tool to generate percent of reads with WT, Indels and edited alleles.

Figure 8B:
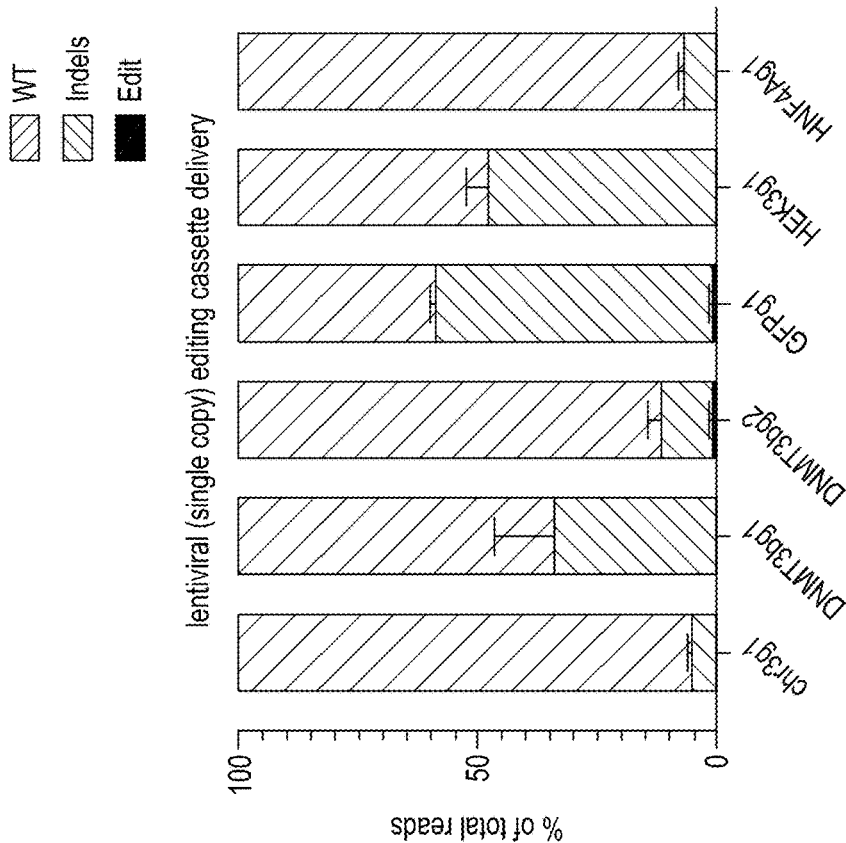
FIGS. 8A and 8B comprise bar graphs which compare single copy lentiviral and multi-copy plasmid delivery of editing cassettes targeting endogenous loci.
Figure 8A:
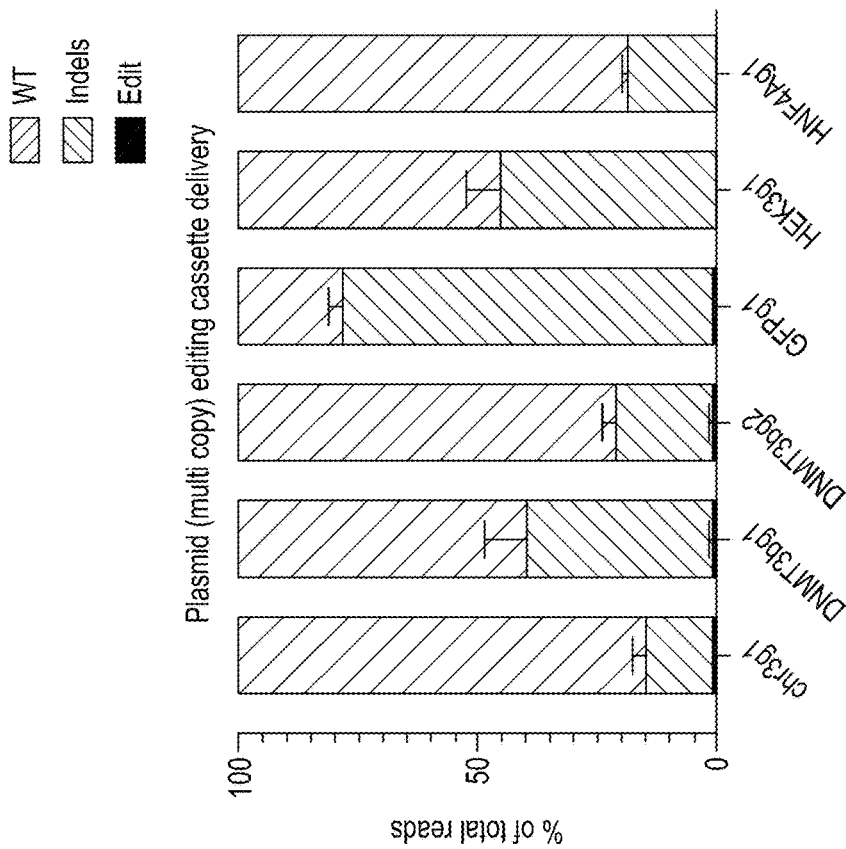
Figure 8D:
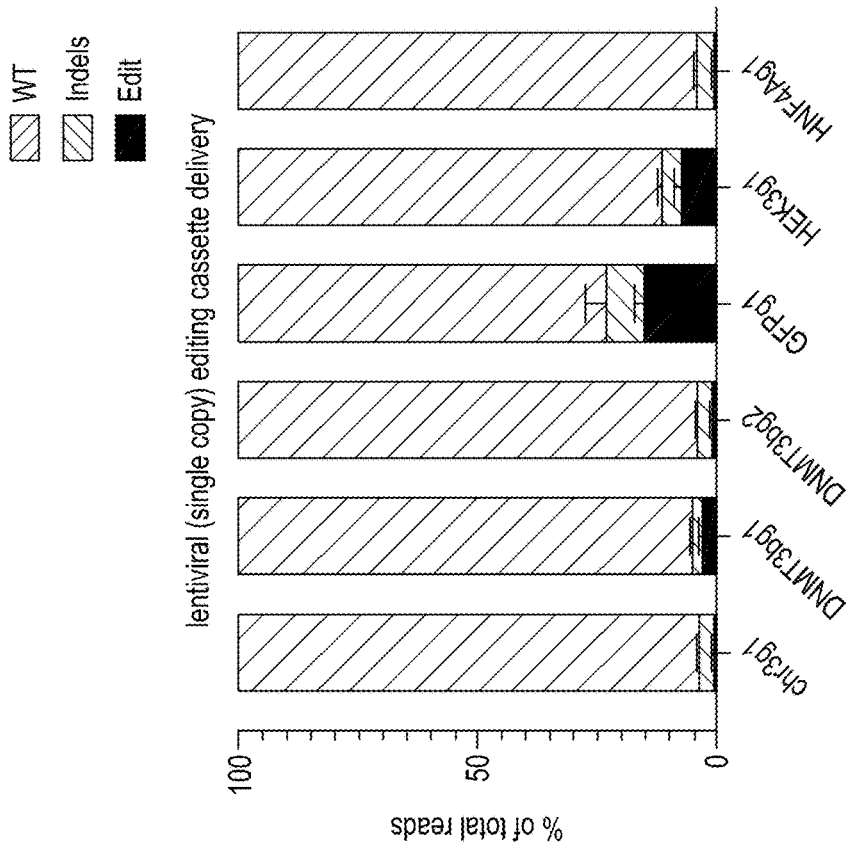
FIGS. 8C, 8D, 8E, and 8F compare single-copy lentiviral and multi-copy plasmid delivery of editing cassettes targeting endogenous loci.
Figure 8C:
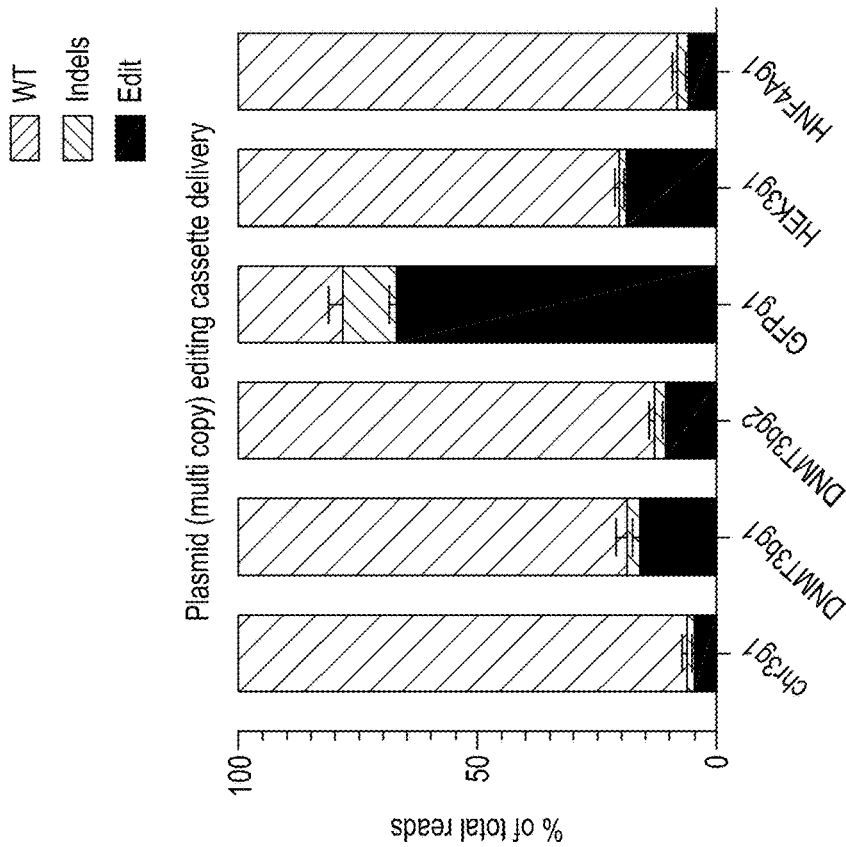
Figure 8F:
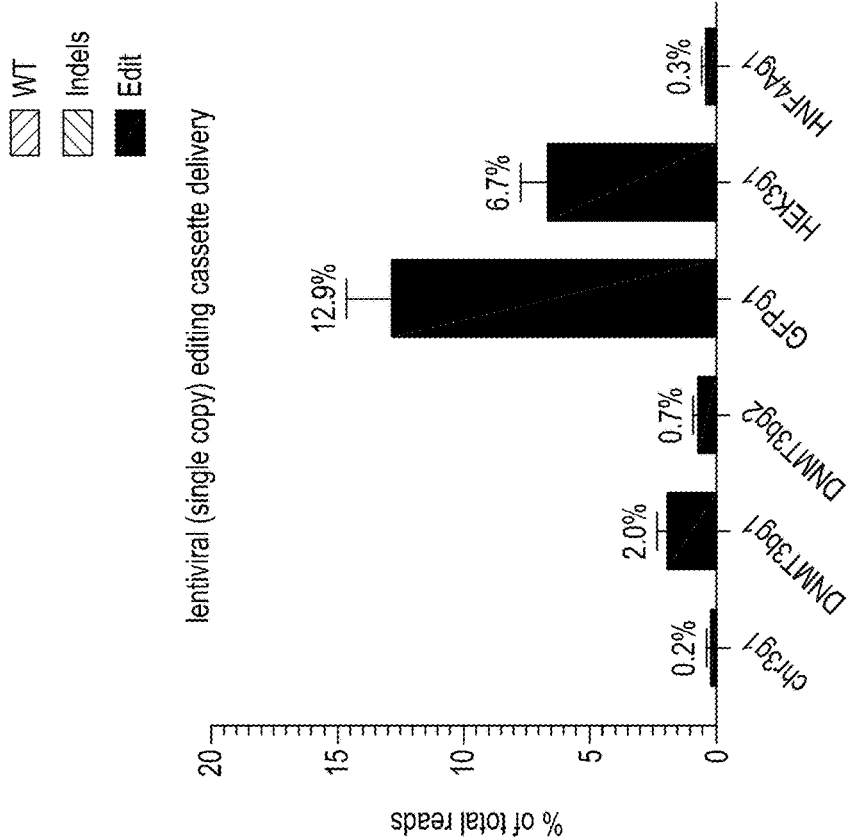
Figure 8E:
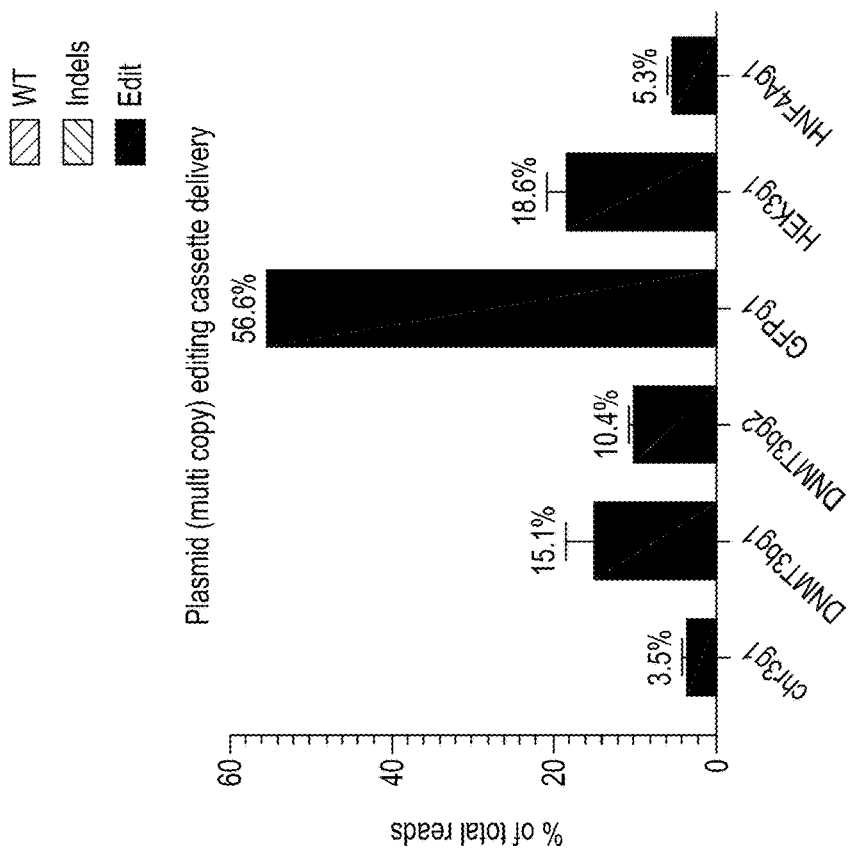

FIGS. 8A and 8C show a comparison of single copy lentiviral and multi-copy plasmid delivery of gRNAs targeting endogenous loci with WT SpCas9. As expected, <1% precise editing is observed and varying levels of indels are observed depending on the target site. Interestingly, the indel rates between plasmid delivery and lentiviral delivery very similar, with no decrease in indels with single copy lentiviral delivery of gRNA.

FIGS. 8C, 8D, 8E and 8F compare single copy lentiviral and multi-copy plasmid delivery of gRNAs targeting endogenous loci with CFE2.2. At all sites tested, unenriched indel rates were below 5%. The unenriched editing rates on the other hand ranged from 3.5% to 56.6% with multicopy delivery and 0.2% to 12.9% with single copy lentiviral delivery. Single copy lentiviral delivery results in lower editing relative to partitioned multi copy delivery. Thus, while gRNA single copy delivery by lentivirus results in lower editing rates relative to multi copy plasmid delivery, lentiviral delivery can be used for pooled scalable editing workflow. The multi copy plasmid delivery is only compatible with fully partitioned editing workflows such as solid wall partitions or droplet partitions.

Example II

Viral Transduction in iPSCs

On day 1, the cells were plated in mTeSR+medium (mTeSR™Plus serum-free, feeder-free cell culture medium (STEMCELL Technologies Canada INC., Vancouver, BC). (mTeSR+medium was used throughout the following procedure.) For transduction on the day of plating (after at least 4 hours after plating), 50K cells were plated per well in a 24-well plate, and 10K cells were plated per well in a 96-well plate. For transduction the day after plating, 25K cells were plated per well in a 24-well plate and 5K cells were plated per well in a 96-well plate.

On day 2 (or day 1 for "day of" transductions), the medium was replaced with fresh medium (no antibiotics). For concentrated virus, cells were transduced at 1:50 (2 µl of virus in 100 µl medium) and for single copy, cells were transduced at 1:10K-1.15K (dilute virus 1000-fold, add 10-6.67 µl of virus (respectively) in 100 µl medium. For unconcentrated virus, to achieve multicopy, cells were transduced at 1× (low volume, 50 µl of undiluted viruse in a 96-well plate). For unconcentrated virus, to achieve single copy, cells were transduced at 1:200 (virus was diluted 4-fold with mTeSR+, with 2 µl of virus to 100 µl medium).

On day 3, the virus was removed after 14-16 hours and fresh medium was added (no antibiotics). On day 4, the medium was replaced with medium containing antibiotics. Antibiotics that were required for maintaining the parental cell line was replaces, and selection was begun for transduced cells. On day 5, medium was replaced in wells, and on day 6, the cell cultures were split, if needed. Medium was replaced with fresh medium with antibiotics if no splitting was required. Blasticidin required 5-10 days for selection, puromycin required 2-3 days for selection. On days 7-8, cell culture continued as normal, medium was changed (with antibiotics) if needed.

On day 9, the cells were plated for tranfections. The medium was aspirated and 50 µl TrypLE™ SELECT (ThermoFisher Scientific, Waltham, Mass., USA) was added to each well. The cells were incubated for 2 minutes at room temperature. The TrypLE™ SELECT (ThermoFisher Scientific, Waltham, Mass., USA) was aspirated and the cell cultures were incubated at 37° C. for 5 minutes. 80 µl medium (+antibiotics, +Rocki (ROCK Inhibitor Y-27632, STEMCELL Technologies Canada INC., Vancouver, BC), +CloneR™ (STEMCELL Technologies Canada INC., Vancouver, BC)) to every well of a new 96-well plate. An additional 100 µl medium (+antibiotics, +Rocki (ROCK Inhibitor Y-27632, STEMCELL Technologies Canada INC., Vancouver, BC), +CloneR™ (STEMCELL Technologies Canada INC., Vancouver, BC)) was added to every well after incubation. The cells were triturated and 20 µl of the cells were transferred to a new plate containing 80 µl fresh medium. The plate designations were as follows:

- 1 plate of CFE (CREATE Fusion Editing) mRNA transfection (in triplicate)+1 replicate for mCherry or Cas9—for NGS
- 1 plate of CFE mRNA transfection (in triplicate)+1 replicate for mCherry or Cas9—for Thy1.2 transfection efficiency
- 1 plate for ddPCR—grow for 3 days before harvesting
- 1 plate for RT-qPCR—transfer cells to a PCR plate containing 100 µL of PBS, centrifuge, aspirate supernatant and follow RT-qPCR workflow or freeze at −80° C.

On day 10, the medium was replaced (without antibiotics for the transfection plates) and the cells were transfected. On day 11, Thy1.2/mCherry transfection efficiency was measured. The medium on the transfection plates was replaced with selection antibiotics and transfection efficiency was measured by staining cells for Thy1.2. The cells in the ddPCR plate were harvested if 100% confluent by aspirating the medium and following a ddPCR protocol for analyzing copy number. On day 13, the transfection plates were harvested for next-generation sequencing. The medium was aspirated from the plate and the cells were harvested using a DNAdvance DNA Extraction kit (Beckman Coulter Lifesciences, Brea Calif.).

Example III

Assessing Feasibility of iPSCs Grown and Transduced on Microcarriers

Figure 9:
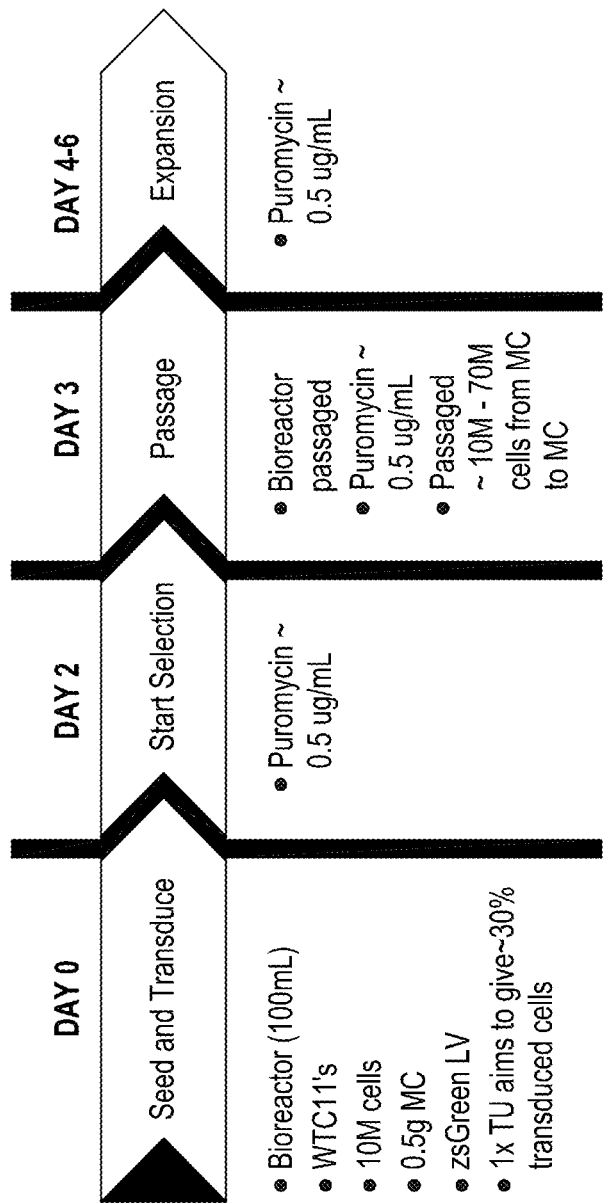
FIG. 9 is a simplified transduction workflow for transduction in the INSCRIPTA™ bioreactor.

FIG. 9 is a simplified workflow for transducing iPSCs on the INSCRIPTA™ bioreactor. On day 0 (the day of transduction), the cells were seeded on laminin L-521 (5 µg/ml) coated microcarriers (27 mg) at 40 cell/microcarrier in mTeSR+medium (mTeSR™Plus serum-free, feeder-free cell culture medium (STEMCELL Technologies Canada INC., Vancouver, BC))+Rocki (ROCK Inhibitor Y-27632, STEMCELL Technologies Canada INC., Vancouver, BC) in 2 mL total volume. Note, mTeSR+medium was used throughout the following procedure. To find optimal viral delivery parameters, cells were transduced at 0, 1, 4, 12 and 24 h after seeding at various lentiviral dilutions (1:250, 1:1000, 1:4000; e.g., 1:250 2 µl of virus for 500 uL medium). On day 1, the virus was removed after 14-16 hours and fresh medium was added (no antibiotics). On day 2, the medium was replaced with medium containing antibiotics zeocin and puromycin. Zeocin required 3-5 days for selection, puromycin required 2-3 days for selection. Following selection, the cells were detached from the microcarriers. Briefly, the microcarriers were transferred to a 5 ml centrifuge tube and allowed to settle. Media was aspirated and the microcarriers were washed with 1 ml PBS.

Figure 10A:
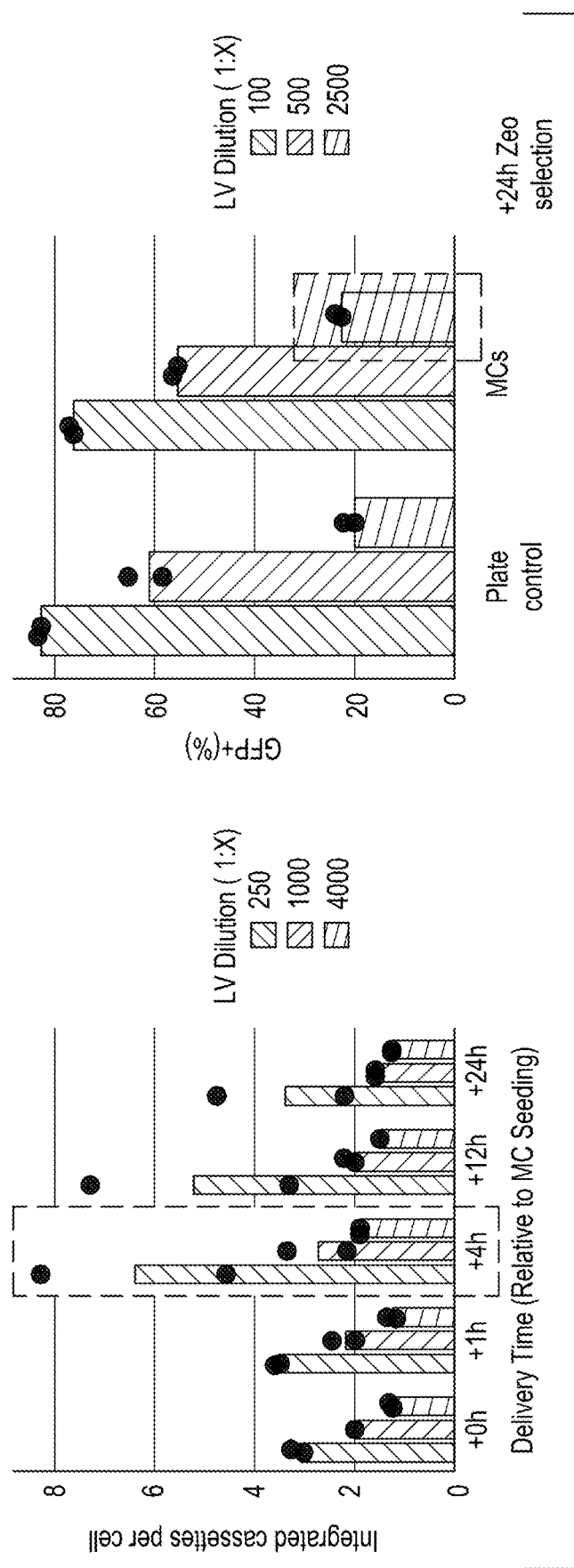
FIG. 10A shows two bar graphs with data demonstrating that transduction is feasible on cells grown on microcarriers.

After wash, the cells were allowed to settle again, and PBS was aspirated. 1 ml TrypLE™ SELECT (ThermoFisher Scientific, Waltham, Mass., USA) was added into the tube, and the cells on the microcarriers were incubated at 37° C. for 6 minutes. The TrypLE was aspirated, and 1 ml fresh media was added to the microcarriers. The cells were detached from the microcarriers by pipetting using a P1000 µlpette (PIPETMAN®). The microcarriers and cells were separated using a 100 mesh cell strainer. An aliquot of detached cells were used in ddPCR assay (Bio-Rad Laboratories, Hercules Calif.) for detecting integrated cassettes per cell and in FACS assays to detect transduced (GFP+) cells using flow cytometry (BD FACSMelody™) (Becton Dickinson, Inc., Franklin Lakes, N.J.) following manufacturer protocols. The results are shown in FIG. 10A. The bar graph at right shows the results of the optimization experiment where cells were seeded on microcarriers at 40 cells/microcarrier and transduced with GFP-lentivirus at various dilutions and delivery times relative to microcarrier seeding. The bar graph at left shows the results of the optimization experiment where cells were seeded on microcarriers at 40 cells/microcarrier and transduced with GFP-lentivirus at 4 hours after seeding. Microcarriers that were transduced with 1:2500 dilution were further used downstream for selection and expansion.

Example IV

Transduction Efficiency and Expansion of iPSCs on Microcarriers

Figure 10B:
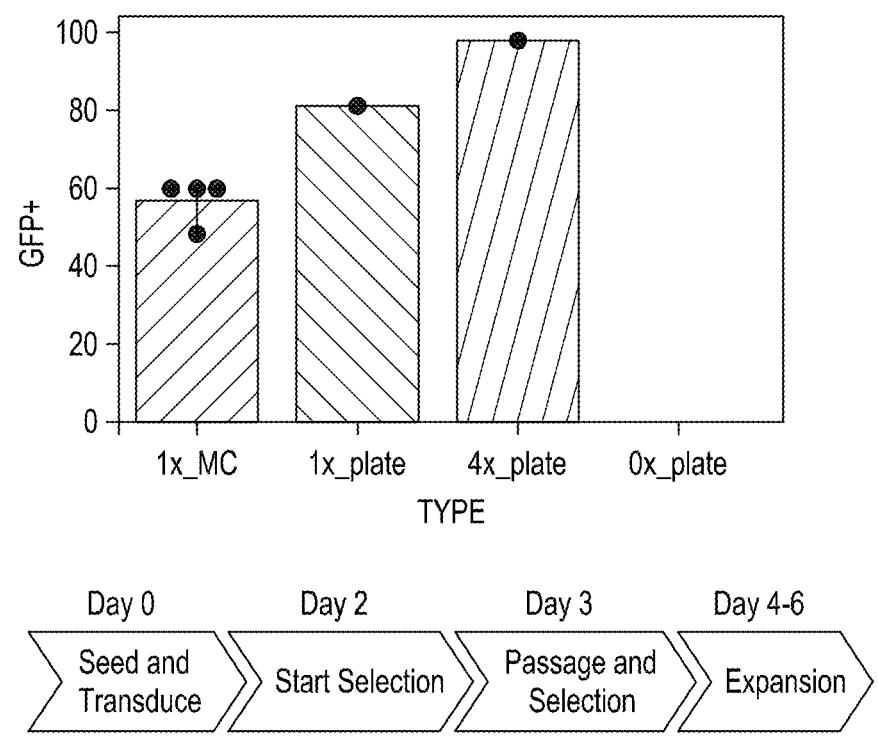
FIG. 10B is a bar graph showing a transduction efficiency of approximately 60%.

On day 0 (day of transduction), ~10M cells were seeded on 0.5 g laminin L-521 (10 µg/ml) coated microcarriers in mTeSR+medium (mTeSR™Plus serum-free, feeder-free cell culture medium (STEMCELL Technologies Canada INC., Vancouver, BC))+CloneR (STEMCELL Technologies Canada INC., Vancouver, BC). During seeding, cells were transduced with zsGreen lentivirus at a multiplicity of infection (MOI) of 0.5-1.0. On day 1, the virus was removed after 14-16 hours and fresh medium was added (no antibiotics, no CloneR). On day 2, the medium was replaced with medium containing antibiotics zeocin and puromycin. Zeocin required 3-5 days for selection, puromycin required 2-3 days for selection. Following selection, cells were passaged onto a new microcarriers using impeller based passaging protocol described elsewhere. An aliquot of detached cells were analyzed using flow cytometer (BD FACSMelody™, Becton Dickinson, Inc., Franklin Lakes, N.J.) to determine the percentage of transduced cells (zsGreen+). FIG. 10B shows the transduction efficiency on both tissue culture plates and on the microcarriers. Note that transduction efficiency was approximately 60% for the cells on the microcarriers.

Figure 10C:
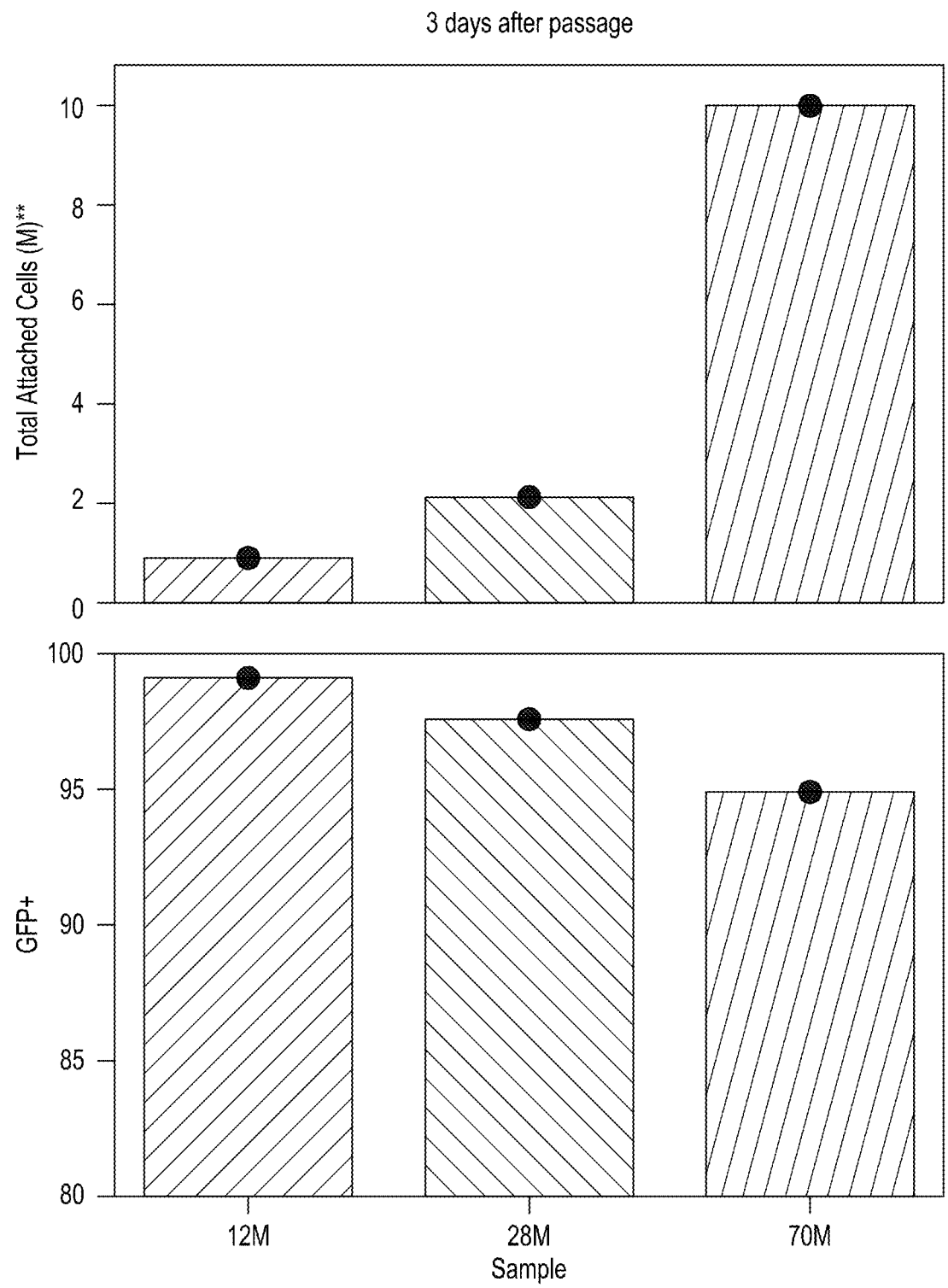
FIG. 10C comprises two bar graphs, one showing data demonstrating that cell expansion after passaging under selection is dependent on re-seeding density, and the second demonstrating that cells maintain a high level of GFP phenotype.

Next, various cell numbers were used to identify optimal cell seeding number (12M, 28M, 70M). After passaging, cells were maintained in mTeSR+medium+CloneR+antibiotics for selection. On day 4, media was refreshed with antibiotics but without CloneR. On days 5-7, cells were maintained as normal, changing medium as needed (with antibiotics). On day 7, cells were detached again using impeller-based detachment protocol, counted to determine total number of cells, and analyzed using flow cytometry to determine the percentage of transduced cells. FIG. 10C shows in the top bar graph the total number of attached cells after passaging for each cell seeding number (12M, 28M, 70M), and FIG. 10C shows in the bottom bar graph the number of expanded cells that retained the GFP+phenotype.

Example V

Complete Workflow and Improved Transfection Efficiency of iPSCs on Microcarriers The essential steps of the editing workflow, namely ability to transduce the cells with guide RNA via lentivirus and transect the cells with editing enzyme, was demonstrated on iPSCs grown on microcarriers by using GFP lentiviral transduction and mCherry mRNA transfection as an analogous workflow. All essential steps of the editing workflow are demonstrated on iPSCs grown on microcarriers by using GFP lentiviral transduction and mCherry mRNA transfection as an analogous workflow to actual editing. On day 0 (the day of transduction), the cells were seeded on laminin L-521 (5 µg/ml) coated microcarriers (27 mg) at 40 cell/microcarrier in mTeSR+medium (mTeSR™ Plus serum-free, feeder-free cell culture medium (STEMCELL Technologies Canada INC., Vancouver, BC))+CloneR (STEMCELL Technologies Canada INC., Vancouver, BC) in 2 ml total volume in 6-well plates (mTeSR+medium was used throughout the following procedure.) Cells were transduced at 4 hours after seeding at 1:2500 lentiviral dilution. On day 1, the virus was removed after 14-16 hours and fresh medium was added (no antibiotics). On day 2, the medium was replaced with medium containing antibiotics zeocin and puromycin. Zeocin required 3-5 days for selection, puromycin required 2-3 days for selection. On day 3, cells were detached from the microcarriers as described above. An aliquot of detached cells was used in FACS assays (BD FACSMelody™, Becton Dickinson, Inc., Franklin Lakes, N.J.) to determine the percentage of transduced (GFP+) cells by following the manufacturer protocols.

Figure 10D:
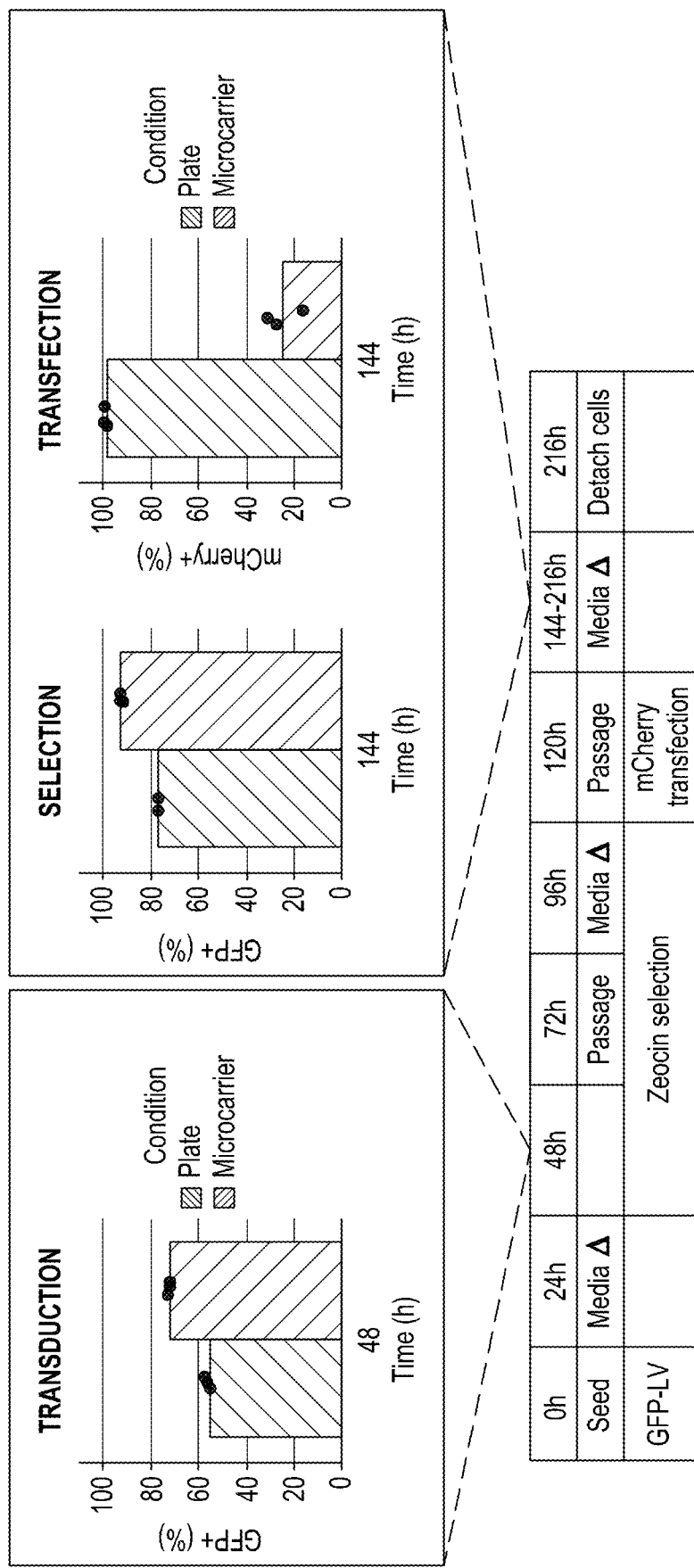
FIG. 10D shows a complete lentiviral editing workflow with iPSCs grown on microcarriers.

Detached cells were re-seeded on fresh laminin coated microcarriers to continue zeocin selection. On day 5, cells were detached again and re-seeded on fresh microcarriers in fresh mTeSR+ and transfected 4 hours after seeding with mCherry mRNA as described in Example II supra. The results shown in FIG. 10D demonstrate that iPSCs were transduced with GFP lentivirus on microcarriers with comparable percentage of GFP+cells across plate and microcarrier cultures, where more than 20% of which were also successfully transfected with mCherry. The transfection efficiency was dependent on reagent delivery time, cell seeding density and lipofection (transfection reagent) mass, and was further improved to >80% by optimal choice of these parameters (e.g., cell seeding at 20 cells/MC, transfection at the time of seeding instead of 4 h after seeding).

Example VI

GFP to BFP Editing of iPSCs on Microcarriers via Transduction and Transfection

Viral transduction of iPSCs with CFgRNA GFP-to-BFP editing cassette: On day 1, the cells were plated in mTeSR+ medium (mTeSR™Plus serum-free, feeder-free cell culture medium (STEMCELL Technologies Canada. INC., Vancouver, BC)). (mTeSR+ medium was used throughout the following procedure.) For transduction on the day of plating (after at least 4 hours after plating), 50K cells were plated per well in a 24-well plate. For transduction the day after plating, 25K cells were plated per well in a 24-well plate.

On day 2 (or day 1 for "day of" transductions), the medium was replaced with fresh medium (no antibiotics). Cells were transduced with virus diluted at 1:50 (2 µl of virus in 100 µl medium) for multicopy integration, 1:10K-1.1.5K (dilute virus 1000-fold, add 10-6.67 µl of virus (respectively) in 100 medium) for single copy integration.

On day 3, the virus was removed after 14-16 hours and fresh medium was added (no antibiotics). On day 4, the medium was replaced with medium containing antibiotics. Antibiotics that were required for maintaining the parental cell line was replaced, and selection was begun for transduced cells. On day 5, medium was replaced in wells, and on day 6, the cell cultures were split, if needed. Medium was replaced with fresh medium with antibiotics if no splitting was required. Blasticidin required 5-10 days for selection, puromycin required 2-3 days for selection. On days 7-14, cell culture continued as normal, medium was changed (with antibiotics) if needed, and cultures were expanded to 6-well plates for standard maintenance by seeding 250K-500K cells per well with 2 mL of growth medium.

On day 15, the cells were seeded onto plates or microcarriers for tranfections. The medium was aspirated and 1 mL TrypLE™ SELECT (ThermoFisher Scientific, Waltham, Mass., USA) was added to each well. The cells were incubated for 2 minutes at room temperature. The TrypLE™ SELECT (ThermoFisher Scientific. Waltham, Mass., USA) was aspirated and the cell cultures were incubated at 37° C. for 5 minutes. 1 ml of medium (+antibiotics, +ROCK Inhibitor Y-27632, STEMCELL Technologies Canada INC., Vancouver, BC), +CloneR™ (STEMCELL Technologies Canada INC., Vancouver, BC)) was added to each well. Cells were triturated, counted, and diluted with additional medium (+antibiotics, +ROCK Inhibitor Y-27632, (STEMCELL Technologies Canada INC., Vancouver, BC), +CloneR™ (STEMCELL Technologies Canada INC., Vancouver, BC)) to a final concentration of 400K cells per ml, and transferred to new plates for transfections. 50 µl, 125 µl, or 1.5 mL of cell suspension was added per well for 96-well planar transfections, 24-well planar transfections, and 6-well microcarrier transfections, respectively. For planar transfections, and additional 50 µl or 125 µl of medium was added per well for 96-well and 24-well cultures, respectively. For microcarrier cultures, a 1.5 ml suspension of Laminin-521 (STEMCELL Technologies Canada INC., Vancouver, BC)) coated Enhanced Attachment Surface Microcarriers (CORNING Inc, New York, USA) (42 mg/ml) was added to each well of the 6-well plates. For microcarrier cultures, the 6-well plates were agitated on an orbital shaker (1.2 cm orbit) at 70 RPM. All cultures were incubated at 7° C. for 4 hours before transfection with CFE (CREATE Fusion Editing) lipoplexes.

Transfection of iPSCs with CFE mRNA: Lipofectarnin-eSTEM (Thermofisher Scientific, Waltham, Mass., USA) was diluted in OptiMEM ((Thermofisher Scientific, Waltham, Mass., USA) to 15% v/v solution. CFE mRNA coding for raCherry+(TriLink Biotechnologies, San Diego, Calif., USA) was diluted in OptiMEM (Thermofisher Scientific, Waltham, Mass., USA) to 50 ng/µl solution. The diluted LipofectamineSTEM was added to the diluted OptiMEM solution and incubated at room temperature for 10 minutes to form CFE lipopiexes. 10 µl, 60 µl, and 300 µl of CFE lipoplex solution was then added 96-well, 24-well, or 6-well iPSC cultures for transfection.

Figure 10E:
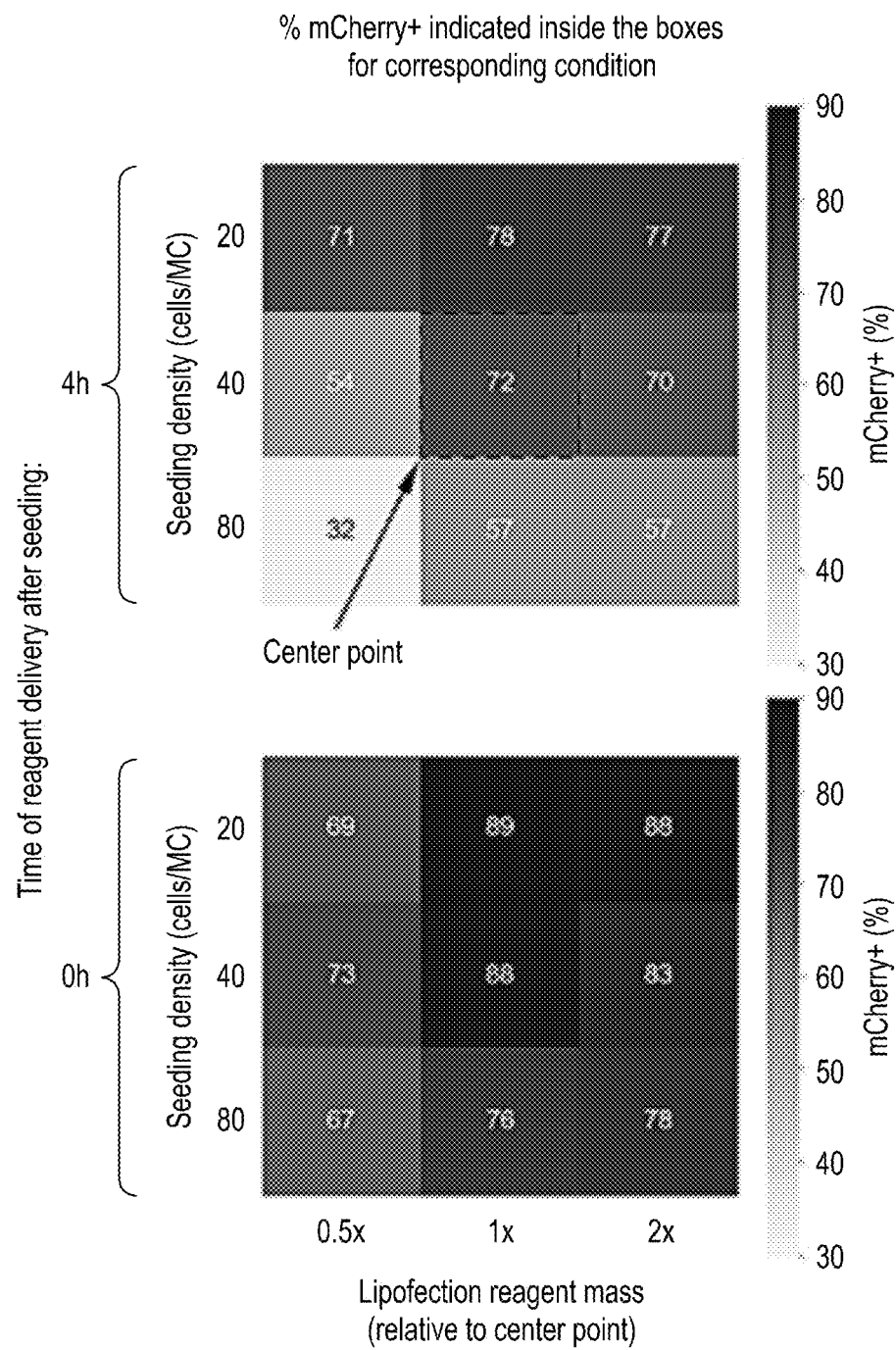
FIG. 10E shows two heat maps demonstrating that transfection efficiency is improved by optimizing cell seeding density, reagent delivery time and transfection reagent mass.
Figure 10F:
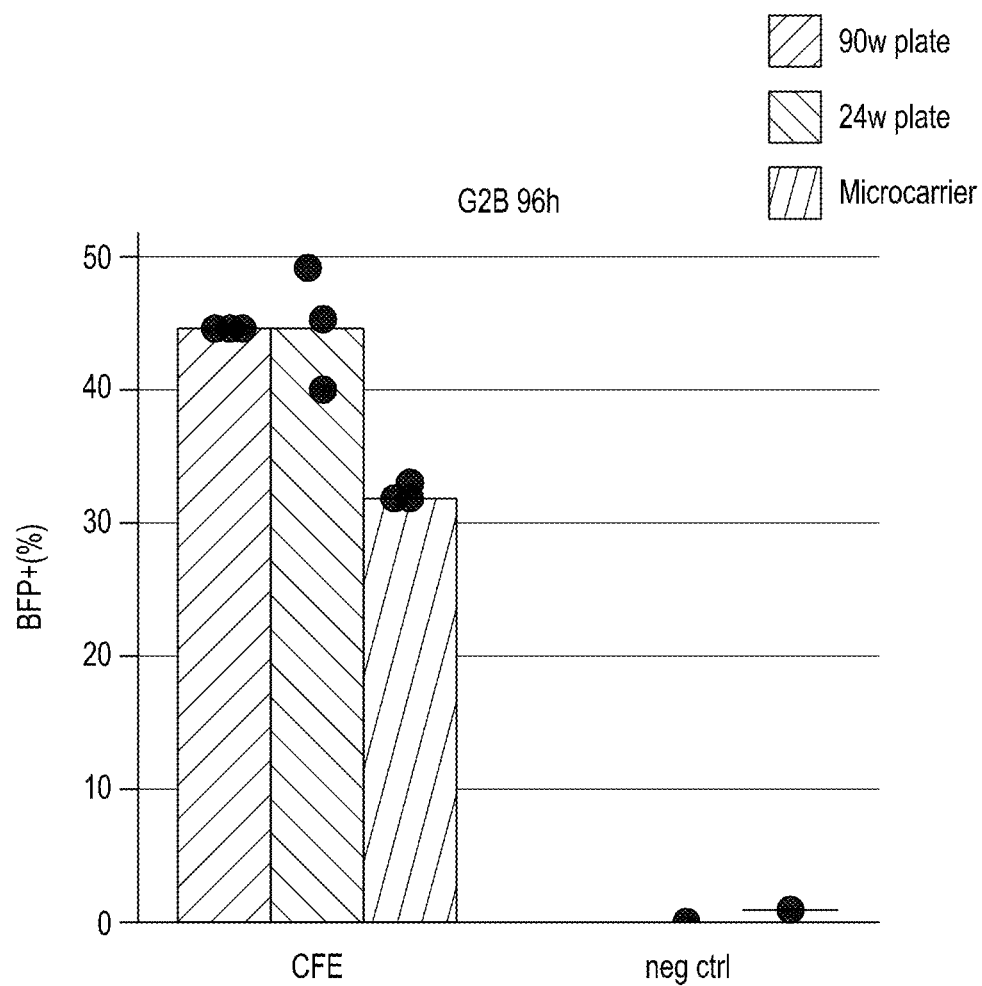
FIG. 10F is a bar graph showing the results of GFP to BFP editing on microcarriers.

On day 16, the transfection medium was replaced with fresh medium. On days 17-19, medium was exchanged if needed. On day 20, cells were lifted for flow cytometry analysis to determine the level of mCherry+ cells (See FIG. 10E). Medium was aspirated and 50 µl, 125 or 1.5 ml ThypLE™ SELECT (ThermoFisher Scientific, Waltham, Mass., USA) was added to each well of 96-well, 24-well, or 6-well plates, respectively. The cells were incubated for 2 minutes at room temperature. The TrypLE™ SELECT (ThermoFisher Scientific, Waltham, Mass., USA) was aspirated and the cell cultures were incubated at 37° C. for 10-15 minutes. Cells were resuspended in flow cytometry buffer (PBS 4-2% FBS+1 mM EDTA) and analyzed on an Attune Nxt flow cytometer (ThermoFisher Scientific, Waltham, Mass., USA) to determine the level of green-to-blue cell editing detected after 96 hours (see FIG. 10F).

Example VII

Biocompatibility of Bioreactor Materials

Biocompatibility of bioreactor relevant materials were screened in plate cultures using conditioned media. mTeSR™ Plus serum-free, feeder-free cell culture medium (STEMCELL Technologies Canada INC., Vancouver, BC) was incubated with the material of interest (i.e., stainless steel and polycarbonate) for at least 72 hours at 4° C. for conditioning the cell culture media. WTC11 iPSCs were seeded on 6-well plates and conditioned media was used to grow cells in standard incubators at 37° C., 5% $CO_2$ and >95% relative humidity. Control cultures were grown similarly to the tested conditions except the medium was not conditioned with any materials and the medium was kept at 4° C. for 72 hours before the start of cultures.

Cells were seeded on Matrigel coated 6-well plates (CORNING® BIOCOAT™ MATRIGEL® 6-well plates (Corning, Inc., Glendale Ariz.)) and cultured with their respective conditioned (tested sample) or unconditioned media (control) and CloneR™ (STEMCELL Technologies Canada INC., Vancouver, BC) for the first 24 hours. After the first 24 hours, cell media was exchanged with fresh conditioned (tested sample) or unconditioned media (control) without CloneR, and maintained up to 72 hours where cells reached confluency. Cell counts and viabilities were assessed at 12-hours, 36-hour and 60-hour time points after lifting cells from the Matrigel CORNING® BIOCOAT™ MATRIGEL® 6-well plates (Corning, Inc., Glendale Ariz.)) plates using ReIesR™ reagent (following the manufacturer's instructions) (STEMCELL Technologies Canada INC., Vancouver, BC) and the cells were quantified on a NucleoCounter NC-200 (Chemometec, Allerod, Denmark) automated cell counting instrument following the manufacturer's instructions.

Figure 11A:
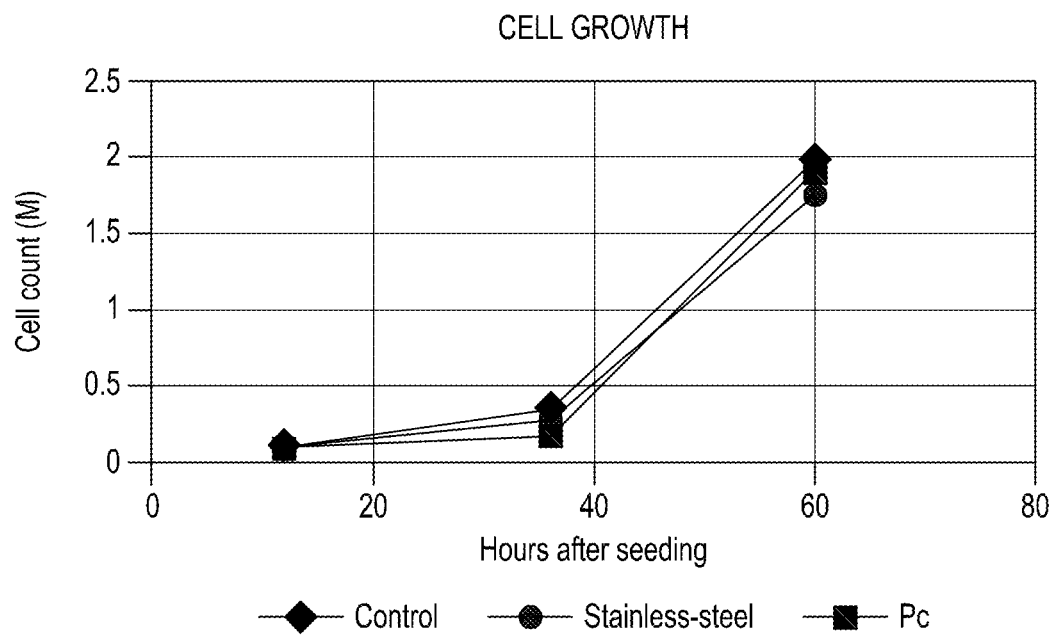
FIGS. 11A and 11B are graphs demonstrating that the materials comprising the components of the bioreactor are biocompatible.
Figure 11B:
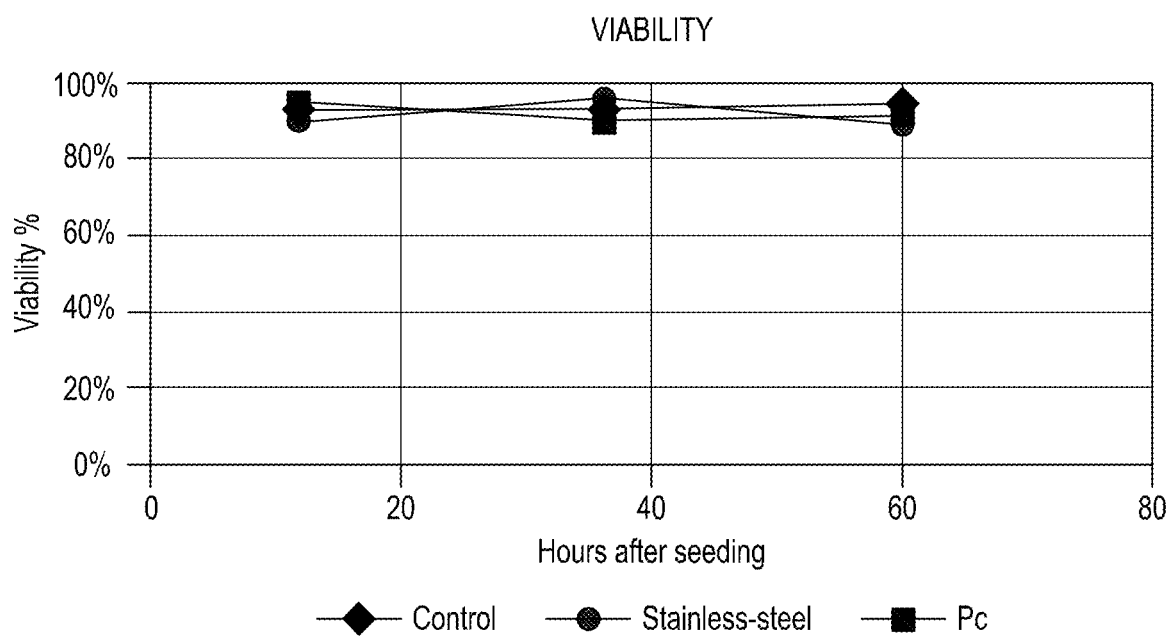

FIGS. 11A and 11B show the results of these experiments. FIGS. 11A and 11B demonstrate neither growth nor viability is impacted by the choice of materials for fabrication of the main body 504 of vessel 501 (polycarbonate), vessel lid assembly 502 (stainless steel), impeller 506 (stainless steel or polycarbonate), or medium exchange frit (stainless steel). All components were sterilized before conditioning.

Example VIII

Optimal Working Volume

The bioreactor described herein was tested for optimal working volume. For sensor operation, minimum optimal volume was set to 100 ml with sensor clearance at 10 mm from the bottom of the main body of the vessel. 10 million WTC11 iPSCs were seeded on 0.5 g of 10 µg/ml laminin L-521 coated Enhanced Attachment microcarriers (Corning, Inc., Glendale Ariz.) in 40 ml and 100 ml mTeSR™Plus serum-free, feeder-free cell culture medium (STEMCELL Technologies Canada INC., Vancouver, BC) and CloneR (STEMCELL Technologies Canada INC., Vancouver, BC in CORNING® spinner flasks (Corning, Inc., Glendale Ariz.). Impeller agitation was set to 70 rpm using a CHIMAREC™ direct stirrer (ThermoFisher Scientific, Waltham Mass.). A first media exchange was performed at 24 hours, and then at every 48th hour with fresh mTeSR™Plus serum-free, feeder-free cell culture medium (STEMCELL Technologies Canada INC., Vancouver, BC) (no CloneR). The cells attached to the microcarriers were quantified at 12-hour and 36-hour time points on a NucleoCounter NC-200 (Chemometec, Allerod, Denmark) automated cell counting instrument following the manufacturer's instructions. Cell counts indicated similar cell seeding efficiencies at 40 ml and 100 ml seeding volumes (data not shown).

Example IX

Assessing Growth in Bioreactor to Traditional Plating and Spinner Flask Culture Experiments were performed to assess whether cell growth in the INSCRIPTA™ bioreactor described herein is equivalent to traditional plate and spinner flask culture conditions. Ten million WTC11 iPSCs were seeded on 0.5 g of 10 µg/ml laminin L-521 coated Enhanced Attachment microcarriers (Corning, Inc., Glendale, Ariz.) in 100 ml mTeSR™Plus serum-free, feeder-free cell culture medium (STEMCELL Technologies Canada INC., Vancouver, BC) and CloneR (STEMCELL Technologies Canada INC., Vancouver, BC) in the INSCRIPTA™ bioreactor and in CORNING® spinner flasks (Corning, Inc., Glendale, Ariz.). Impeller agitation was performed at 70 rpm for both the INSCRIPTA™ bioreactor and CORNING® spinners. A control culture was also seeded on Matrigel coated 6-well plates (CORNING® BIOCOAT™ MATRIGEL® 6-well plates (Corning, Inc., Glendale, Ariz.)) using 500 k cells per one well. The cells were maintained at 37° C., 5% $CO_2$ and >95% relative humidity throughout the culture period. The first media exchange was performed at 24 hours, and then at every 48th hour with fresh mTeSR™Plus serum-free, feeder-free cell culture medium (STEMCELL Technologies Canada INC., Vancouver, BC) (no CloneR) using 100 ml for microcarrier cultures and 2 ml per well for 6-well plates. Cell counts were quantified at 12-hour, 36-hour and 60-hour time points on a NucleoCounter NC-200 (Chemometec, Allerod, Denmark) automated cell counting instrument following the manufacturer's instructions.

Figure 12:
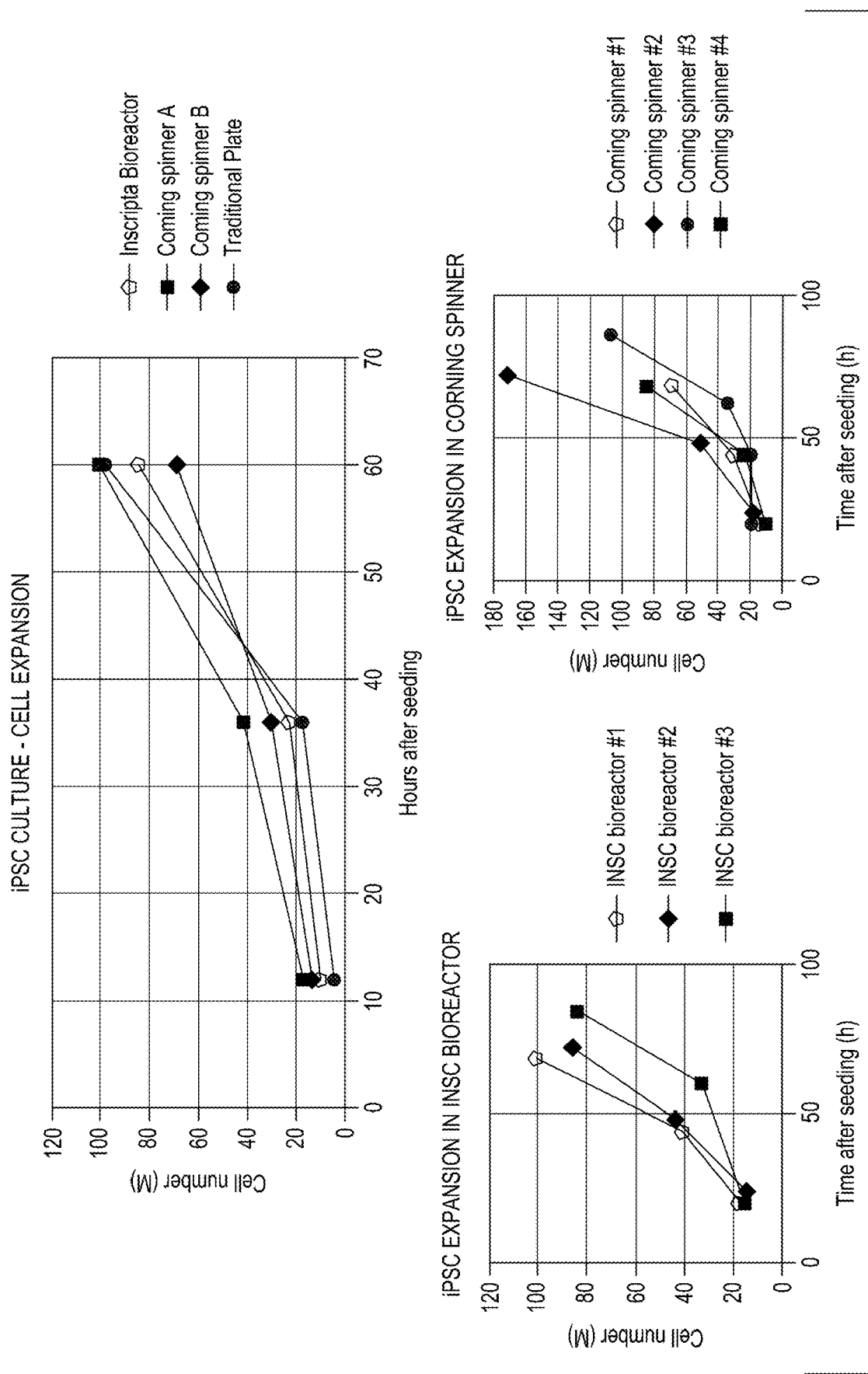
FIG. 12 comprises three graphs demonstrating that iPSC culture and cell expansion in the bioreactor described herein is comparable to cell culture and expansion in a CORNING® spinner flask and in a traditional cell culture plate.

The results are shown in FIG. 12. The graph at top shows similar numbers of iPSC cells at 10, 20, 30, 40, 50, 60, and 70 hours after seeding. The graph at bottom right shows similar results were obtained for iPSC cell expansion in three different INSCRIPTA™ bioreactors. The graph at bottom left shows the results obtained for iPSC cell expansion in four different CORNING® spinner flasks. Growth curves plotted using these cell counts indicated similar cell growth curves under the conditions tested. The 6-well plate control counts were scaled assuming an initial cell seeding number of 10 million cells for comparison. Additional INSCRIPTA™ bioreactors and CORNING® spinner flasks were seeded on different days using the same methods to compare cell growth curve variations and showed similar variation across INSCRIPTA™ bioreactors and CORNING® spinners.

Example X

Effect of Medium Exchange

Figure 13:
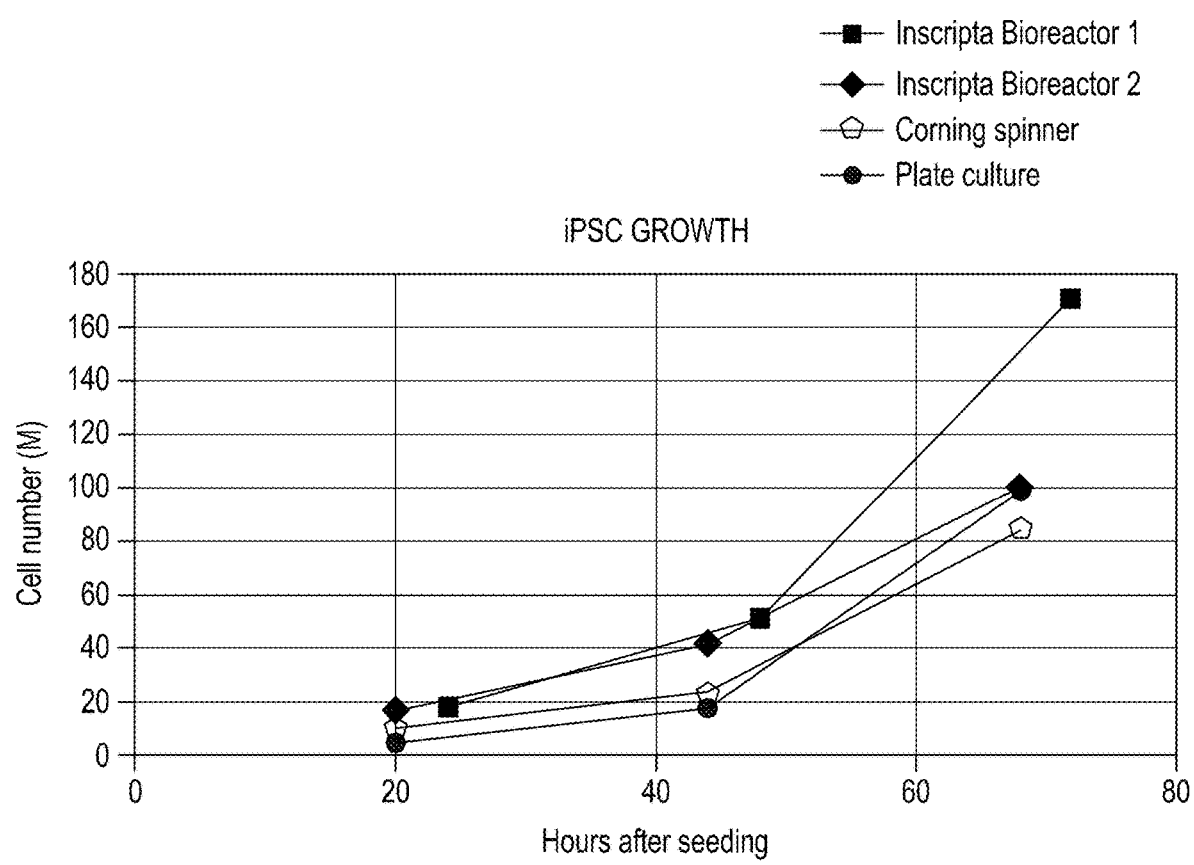
FIG. 13 is a graph showing that media exchange at ~200 ml/minute does not impact cell growth.

Ten million WTC11 iPSCs were seeded on 0.5 g of 10 µg/ml laminin L-521 coated Enhanced Attachment microcarriers (Corning, Inc., Glendale, Ariz.) in 100 ml mTeSR™Plus serum-free, feeder-free cell culture medium (STEMCELL Technologies Canada INC., Vancouver, BC) and CloneR (STEMCELL Technologies Canada INC., Vancouver, BC) in INSCRIPTA™ bioreactors and CORNING® spinner flasks. Impeller agitation was performed at 70 rpm for both the INSCRIPTA™ bioreactors and the CORN- ING® spinners. A 6-well plate control culture was also seeded on CORNING® BIOCOAT™ MATRIGEL® 6-well plates (Corning, Inc., Glendale, Ariz.) was also seeded using 500 k cells per one well. The cells were maintained at 37° C., 5% $CO_2$ and >95% relative humidity throughout the culture period. A first media exchange was performed at 24 hours, and then at every 48th hour with fresh mTeSR™Plus serum-free, feeder-free cell culture medium (STEMCELL Technologies Canada INC., Vancouver, BC) (no CloneR) using 100 ml for microcarrier cultures and 2 ml per well for 6-well plates. Media exchanges on the INSCRIPTA™ bioreactors were performed using a frit system as follows: Impeller agitation was stopped and the microcarriers were allowed to settle gravitationally for 5 minutes. After settling, >90% of the spent media was aspirated from the INSCRIPTA™ bioreactor through a frit connected to a peristaltic pump operating at 200 ml/min flow rate. The frit consisted of ~100 micron pores while the microcarriers ranged from 120-225 micron in diameter. As such, microcarriers were retained in the bioreactor but spent media and dead cells were aspirated out of the bioreactor vessel. As a comparison, media exchange in CORNING® spinner flasks and 6-well plates were performed using a serological pipette connected to an aspirator (BVC Professional Aspiration System (Vacuubrand, Essex, Conn.)). In all conditions, fresh media was added manually using a serological pipette. Cell counts were quantified at 20-hour, 44-hour and 68-hour time points on a NucleoCounter NC-200 (Chemometec, Allerod, Denmark) automated cell counting instrument following the manufacturer's instructions. The results are shown in FIG. 13. Growth curves plotted using these cell counts indicated that the media exchange approach through a frit does not have any noticeable impact on cell growth. The 6-well plate control counts were scaled assuming an initial cell seeding number of 10 million cells for comparison. During the process there was no accumulation of microcarriers on the frit in the liquid-out port.

Example XI

Effect of Impeller Shear on Cell Viability and Reproducibility

Cell detachment from microcarriers may be achieved using an impeller agitation-based approach as follows: 10M cells were seeded on 0.5 g of 10 μg/ml laminin L-521 coated microcarriers (Corning, Inc., Glendale, Ariz.), and expanded in the INSCRIPTA™ bioreactor at 100 ml mTeSR™Plus serum-free, feeder-free cell culture medium (STEMCELL Technologies Canada INC., Vancouver, BC) at 37° C., 5% $CO_2$, and >95% relative humidity as described above. Once the cells reached >50 million cells as determined by cell counting, the microcarriers were allowed to settle gravitationally for 5 minutes, and >90% of the spent media was aspirated. 100 ml phosphate buffered saline (PBS) was added to microcarriers for washing and aspirated after 5 minutes. 100 ml RelesR (STEMCELL Technologies Canada INC., Vancouver, BC) was added to the microcarriers and incubated at 37° C. for 6 minutes. After 6 minutes, >90% of the RelesR (STEMCELL Technologies Canada INC., Vancouver, BC) was aspirated and 100 ml of cell media was added to the microcarriers to quench any RelesR.

At this stage, impeller agitation was performed by rotating the impeller at 2700 rpm in the clockwise direction for 15 seconds first, and then at 2700 rpm in the counterclockwise direction for 15 seconds. This bi-directional agitation for a total of 30 seconds duration was defined as "one round" or "one cycle". Up to five rounds/cycles of impeller agitation was tested in terms of cell detachment efficiency. After detachment, the cell and microcarrier suspension was transferred to a conical vessel. Cells and microcarriers were separated using gravitational settling where the microcarriers settle faster than the cells due to their larger diameter. In another approach, the cell and microcarrier suspension was passed through a strainer with 100 micron mesh size (e.g., CORNING® Sterile Cell strainer-100 micron, Corning, Inc., Glendale, Ariz.) to separate the cells from the microcarriers. As control, a 1 ml aliquot of microcarrier culture was detached using a P1000 μlpette (PIPETMAN®) by passing the microcarriers through the pipette 5 times. After detachment, post detachment viability and the number of detached cells were quantified for assessing detachment efficiency.

Figure 14:
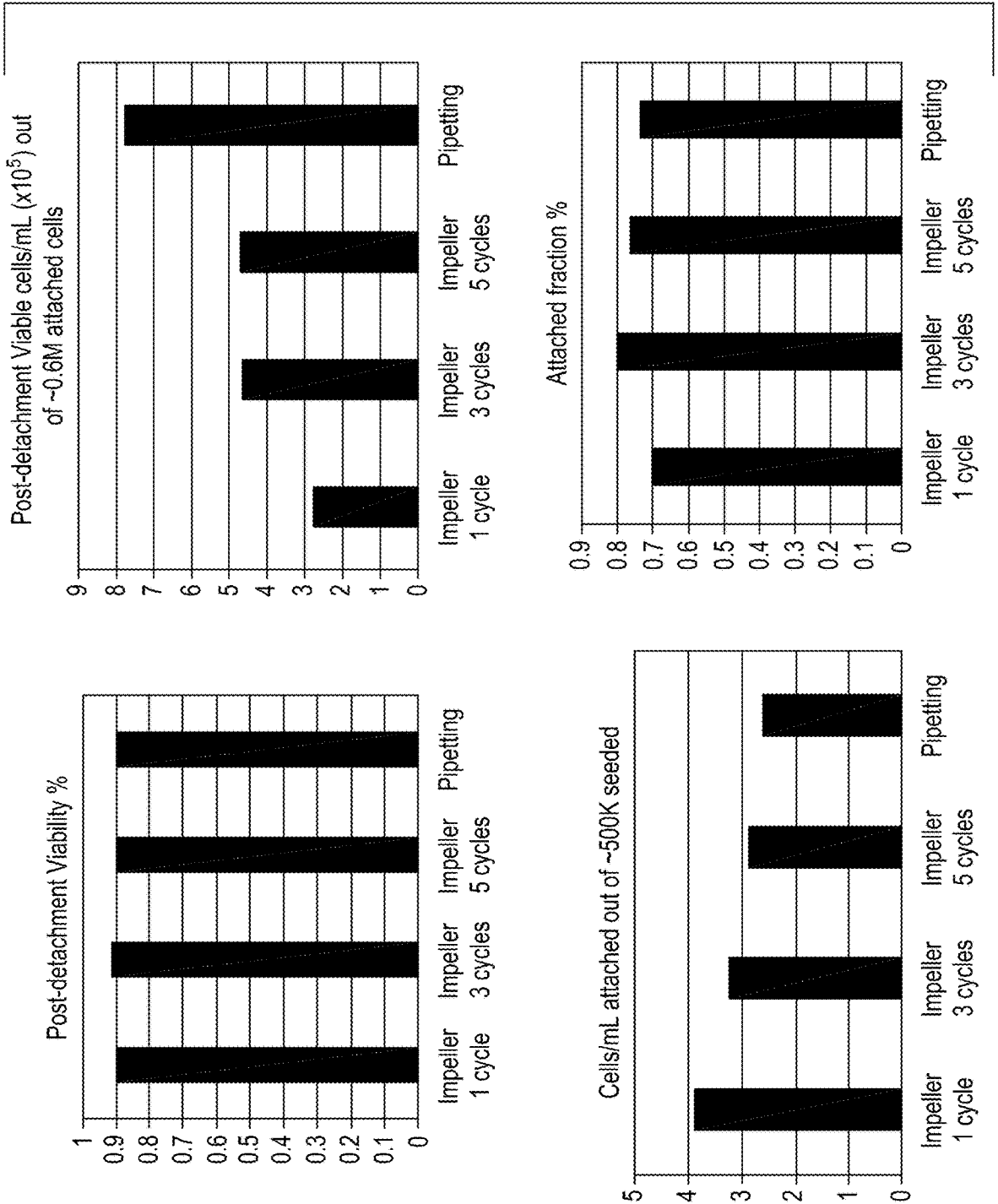
FIG. 14 is a series of four graphs demonstrating that up to five rounds of impeller shear is tolerated by iPSCs with no negative effects on re-seeding.
Figure 15:
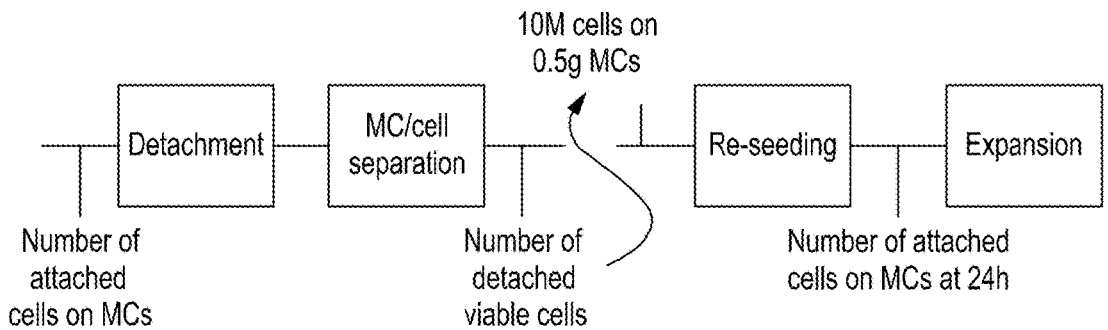
FIG. 15 shows a workflow at upper right, a table reporting percent efficiency at various steps in the workflow at lower right, and a graph showing the replicates measuring the percent efficiency at various steps in the workflow at left.
Figure 15:
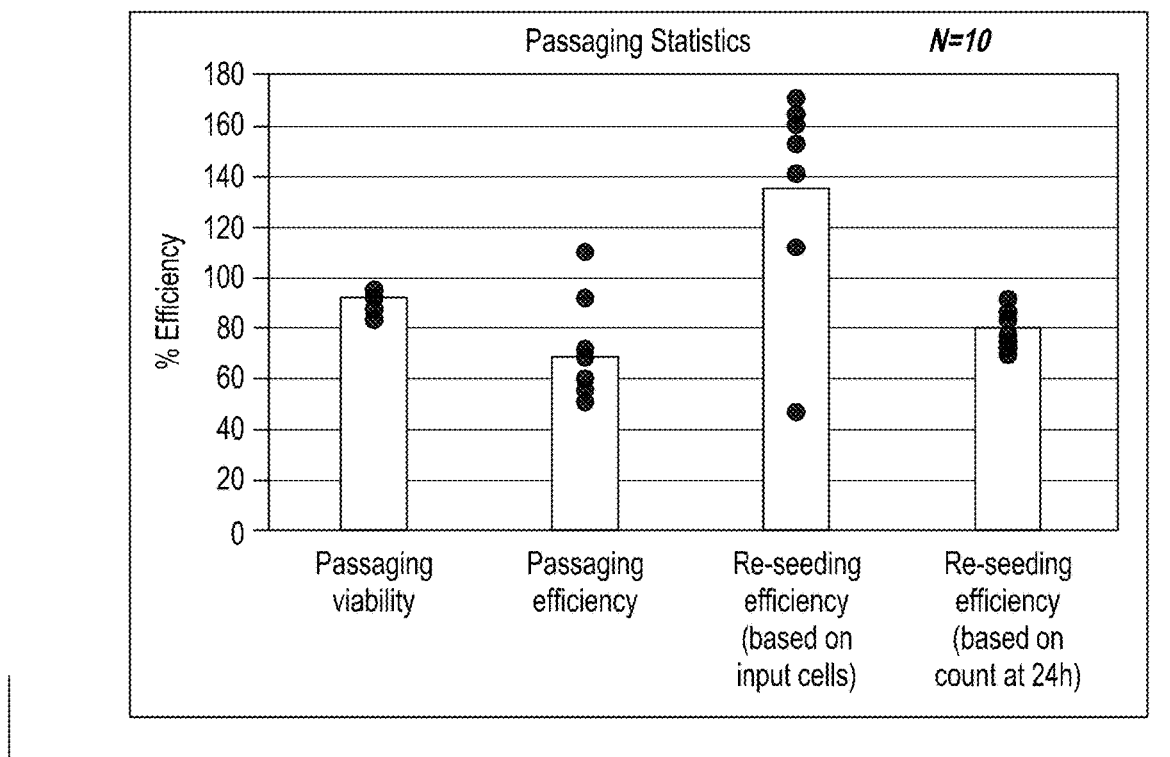

The results are shown in FIG. 15. The graph at top left of FIG. 14 shows the percent post-detachment of the cells. The graph right in FIG. 14 shows the number of viable cells/ml ($\times 10^5$) out of ~0.6M attached cells. The graph at bottom left in FIG. 14 shows the number of cells/ml attached out of ~500K seeded. Finally, the graph at bottom right in FIG. 14 shows the attached fraction of cells after each cycle. Note that viability remained around 90% after all of the first, third and fifth cycles. The cells were effectively detached from the microcarriers using the impeller agitation approach and showed >90% post-detachment viability after up to 5 rounds of impeller agitation, which was similar to the control. The re-seeding efficiency of cells detached with impeller agitation were also similar to the control case where ≥70% of the detached cells were able to re-seed.

Reproducibility of impeller agitation-based passaging was tested. Ten million cells were seeded on 0.5 g of 10 μg/ml laminin L-521 coated microcarriers (Corning, Inc., Glendale, Ariz.), and expanded in the INSCRIPTA™ bioreactor in 100 ml mTeSR™Plus serum-free, feeder-free cell culture medium (STEMCELL Technologies Canada INC., Vancouver, BC) at 37° C., 5% $CO_2$, and >95% relative humidity as described above. Once the cells reached >50 million cells as determined by cell counting, the microcarriers were allowed to settle gravitationally for 5 minutes and >90% spent media was aspirated. 100 ml phosphate buffered saline (PBS) was added to the microcarriers for washing and was aspirated after 5 minutes. 100 ml RelesR (STEMCELL Technologies Canada INC., Vancouver, BC) were added to the microcarriers and incubated at 37° C. for 6 minutes. After 6 minutes, >90% of the RelesR was aspirated and 100 ml of cell media was added to the microcarriers to quench any RelesR. At this stage impeller agitation was performed by rotating the impeller at 2700 rpm in clockwise direction for 15 seconds first, and then at 2700 rpm in counterclockwise direction for 15 seconds. This bi-directional agitation for a total of 30 seconds duration was defined as "one round" or "one cycle". Three rounds/cycles of impeller agitation were used to detach the cells from microcarriers. After detachment, the cell and microcarrier suspension was transferred to a conical vessel. The cells and the microcarriers were separated using gravitational settling where the microcarriers settle faster than cells due to their larger diameter. Detached cells were re-seeded on fresh microcarriers at 10 million cells per 0.5 g of CORNING® laminin coated microcarriers (Corning, Inc., Glendale, Ariz.), and re-seeding efficiencies were determined based on cell counts at 24 hours after seeding. Passaging and re-seeding efficiencies are quantified and shown in the FIG. 15. FIG. 15 at top shows a simplified workflow for this process, as well as at middle a table showing the efficiency of each step, and at bottom a bar graph of passaging statistics for the indicated steps. The results indicate that impeller-based passaging is reproducible and allows for re-seeding of 30-65% of cells that were on the microcarriers prior to detachment.

Example XII

Cell Re-Seeding and Expansion after Impeller Passaging

Figure 16:
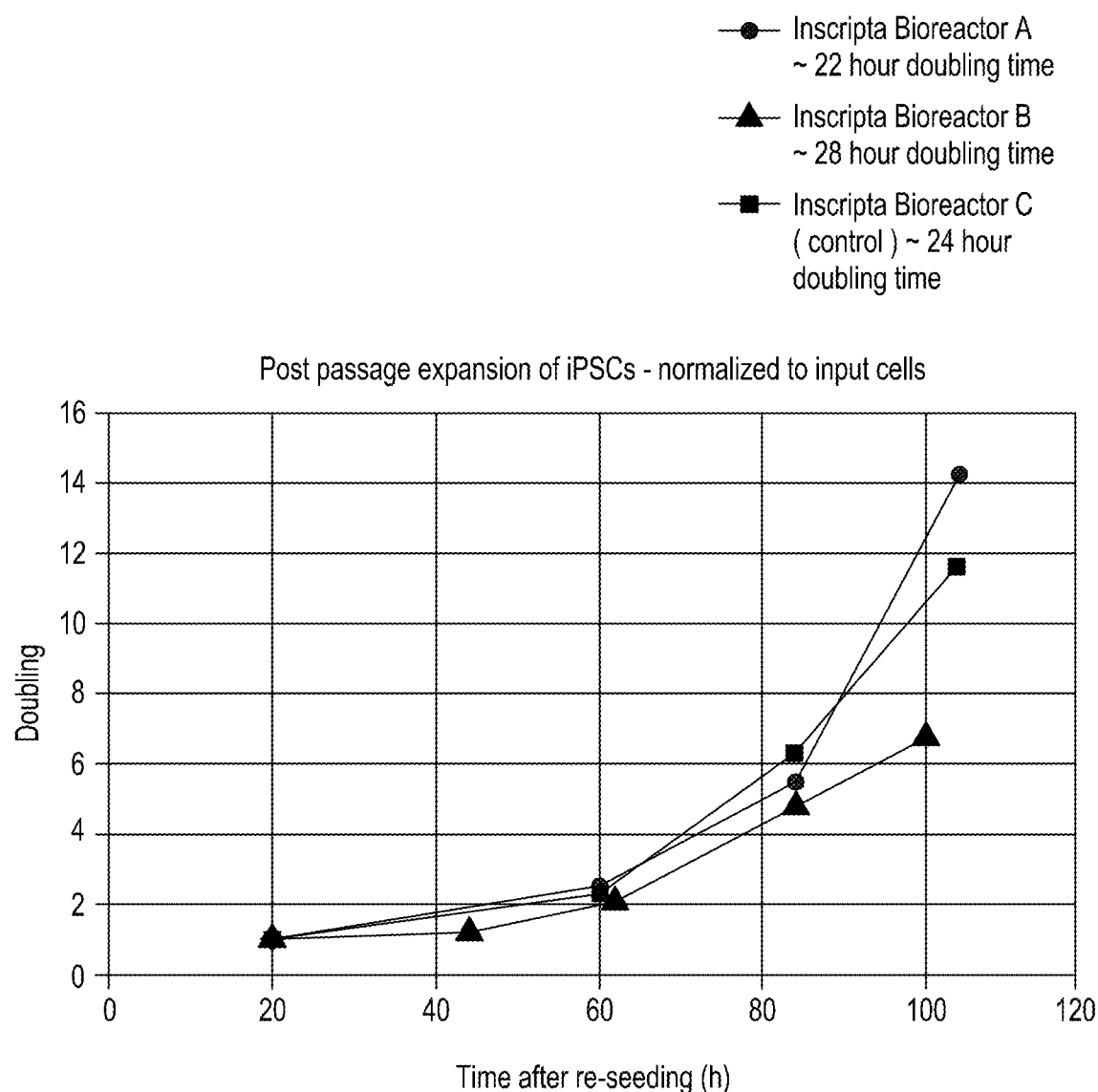
FIG. 16 is a graph showing that cell seeding and expansion are both unaffected by the impeller-shear based passaging protocol.

Cell seeding and expansion after impeller passaging was tested. Ten million WTC11 cells were seeded on 0.5 g of 10 µg/ml laminin L-521 coated microcarriers (Corning, Inc., Glendale, Ariz.), and expanded in the INSCRIPTA™ bioreactor in 100 ml mTeSR™Plus serum-free, feeder-free cell culture medium (STEMCELL Technologies Canada INC., Vancouver, BC) at 37° C., 5% $CO_2$, and >95% relative humidity as described above. Once the cells reached >50 million cells as determined by cell counting, the impeller passaging protocol was implemented as described above. After detachment, 10M detached cells were re-seeded on 0.5 g of fresh laminin coated microcarriers (Corning, Inc., Glendale, Ariz.) and expanded as described above. As a control, an INSCRIPTA™ bioreactor was seeded with cells detached from T75 flasks detached using standard protocols. Cell counts were quantified at 20-hour, 44-hour and 68-hour time points on a NucleoCounter NC-200 (Chemometec, Allerod, Denmark) automated cell counting instrument following the manufacturer's instructions. The results are shown in FIG. 16. FIG. 16 is a graph of triplicate results demonstrating that cell seeding and expansion are unaffected by impeller-shear passaging.

Example X

Ability of Cells to Maintain Stemness

The ability of the iPSCs to retain sternness during culture and passaging was tested. Ten million cells were seeded on 0.5 g of 10 µg/ml laminin L-521 coated microcarriers (Corning, Inc., Glendale, Ariz.), and expanded in an INSCRIPTA™ bioreactor in mTeSR™ Plus serum-free, feeder-free cell culture medium (STEMCELL Technologies Canada INC., Vancouver, BC) at 37° C., 5% $CO_2$, and >95% relative humidity as described above. Once the cells reached >50 million cells as determined by cell counting, the impeller passaging protocol was implemented and 10M detached cells were re-seeded onto fresh 0.5 g laminin coated microcarriers (Corning, Inc., Glendale, Ariz.). This process was repeated two more times and the cells were stained after final detachment using antibodies (BIOLEGEND®, San Diego, Calif.) specific to three sternness expression markers (TRA-1-60, OCT-3/4 and SOX-2) following the manufacturer's instructions, followed by analysis using flow cytometry (BD FACSMelody™) (Becton Dickinson, Inc., Franklin Lakes, N.J.). Cells grown and impeller passaged on the INSCRIPTA™ bioreactors showed expression of sternness markers similar to the cells grown on Matrigel (CORNING® BIOCOAT™ MATRIGEL® 6-well plates (Corning, Inc., Glendale, Ariz.)) and laminin coated plates (CORNING® BIOCOAT™ laminin plates (Corning, Inc., Glendale, Ariz.)).

Sternness antibody staining was performed in the following manner, with the equipment and materials listed in Table 1:

TABLE 1

Foxp3/Transcription Factor Fixation/Permeabilization Concentrate and Diluent, ThermoFisher Scientific, cat. # 00-5521-00
eBioscience™ Flow Cytometry Staining Buffer, ThermoFisher Scientific, cat. # 00-4222-26
Anti-SOX2 (Brilliant Violet 421): Biolegend, cat. # 656114
Anti-OCT3/4 (Alexa488): Biolegend, cat. # 653706
Anti-TRA-1-60 (PE-Cy7): Biolegend, cat. # 330620
Anti-CD44 (PE-Cy5): ThermoFisher Scientific, cat. # 15-0441-82
Anti-CD13 (PE-Cy7): Biolegend, cat. # 301712
Anti-NESTIN (Alexa488): Biolegend, cat. # 656812
Anti-SSEA4 (V450): BD Biosciences, cat. # 561156
FACSMelody™ flow cytometer (Becton Dickinson, Inc., Franklin Lakes, NJ)

In a first step, a single-cell suspension was prepared and centrifuged 5 minutes at 200×g. The cells were then washed in an appropriate volume of DPBS and centrifuged again for 5 minutes at 200×g. The supernatant was discarded and the pellet was vortexed to dissociate the pellet. Fresh Foxp3 fixation/permeabilization working solution (ThermoFisher Scientific, Waltham Mass.) was prepared by mixing one part Foxp3 fixation/permeabilization concentrate with three parts Foxp3 fixation/permeabilization diluent and 1 ml was added to each tube and each tube was then vortexed. The vortexed cells and fixation/permeabilization working solution were incubated for 30-60 minutes in the dark at room temperature. A 1× working solution of permeabilization buffer was prepared by mixing 1 part 10× permeabilization buffer with 9 parts $dH_2O$ and 2 ml was added to each sample. The cells were centrifuged at 400-600×g for 5 minutes at room temperature and the supernatant was discarded. The cell pellet was resuspended in 1× permeabilization buffer for a total volume of approximately 100 µl. The cells were diluted so that there were no more than 10,000 cells/µl, and 1M cells were transferred to a fresh tube. The appropriate amount of directly-conjugated antibody was dispensed into each tube. The cells were incubated for >30 minutes in the dark at room temperature. Two ml of 1× permeabilization buffer was added to each tube and the samples were centrifuged at 400-600×g for 5 minutes at room temperature and the supernatant was discarded. The stained cells were suspended in flow cytometry staining buffer.

Figure 17:
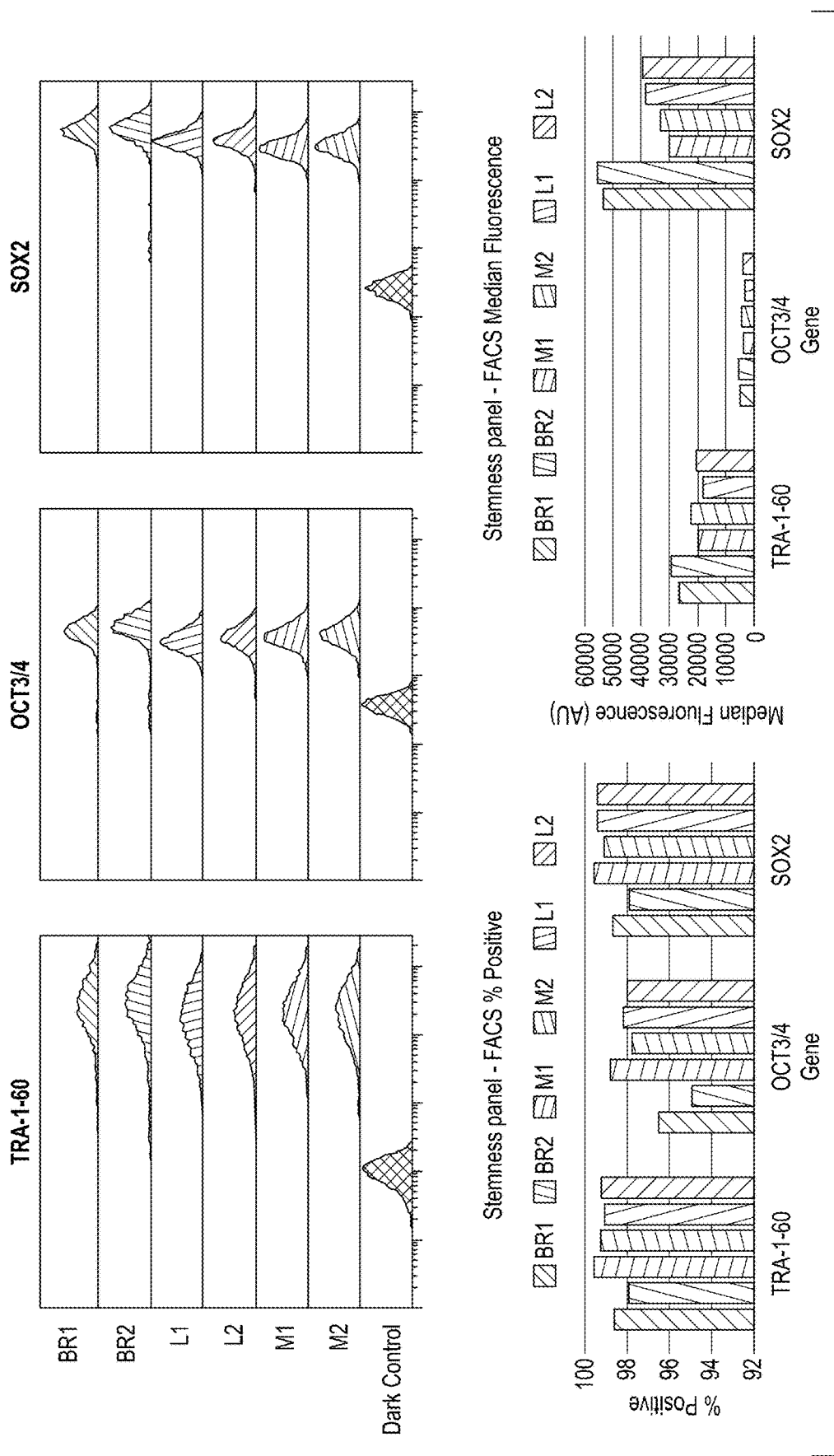
FIG. 17 at top are histograms showing the fluorescent expression distribution measured via flow cytometry of the cell population for individual stemness marker expression.

The results are shown in FIG. 17. FIG. 17 at top are histograms showing the fluorescent expression distribution measured via flow cytometry of the cell population for individual stemness marker expression. The x-axis shows the fluorescence signal and the y-axis shows cell count. BR1 indicates results for INSCRIPTA™ bioreactor 1, BR2 indicates results for INSCRIPTA™ bioreactor 2 (replicate), L1 indicates CORNING® BIOCOAT™ laminin plates (Corning, Inc., Glendale, Ariz.), L2 indicates CORNING® BIOCOAT™ laminin plates (Corning, Inc., Glendale, Ariz.) (replicate), M1 indicates CORNING® BIOCOAT™ MATRIGEL® 6-well plates (Corning, Inc., Glendale, Ariz.), and M2 indicates CORNING® BIOCOAT™ MATRIGEL® 6-well plates (Corning, Inc., Glendale, Ariz.) (replicate). A dark control was used for comparison where the cells in one well from the M1 6-well plate are prepared as the experimental cells but were not stained with antibodies. Looking at the graph at bottom left of FIG. 17, note that the percent of cells positive for the TRA-1-60 and SOX2 cell surface markers was similar across culture conditions. Cell surface marker OCT3/4 was a little lower (94-96%) in the cells grown in the INSCRIPTA™ bioreactors than in the laminin plates (98%) and in the MATRIGEL® plates (98%). The graph at right of FIG. 17 shows the median fluorescence obtained for each of TRA 1-60, OCT3/4 and SOX2 markers for each bioreactor, laminin plate and MATRIGEL® plate replicate.

Example XIII

Ability of Cells to Maintain Differentiation Potential

To test whether cells grown in the INSCRIPTA™ bioreactor would retain differentiation potential, ten million cells were seeded on 0.5 g of 10 µg/ml/aminin L-521 coated microcarriers (Corning, Inc., Glendale, Ariz.), and expanded in INSCRIPTA™ Bioreactor in 100 ml mTeSR™Plus serum-free, feeder-free cell culture medium (STEMCELL Technologies Canada Inc., Vancouver, BC) at 37° C., 5% $CO_2$, and >95% relative humidity as described above. Once the cells reached >50 million cells as determined by cell counting, the impeller passaging protocol as described above in Example VII was implemented and 10M detached cells were re-seeded onto 0.5 g fresh laminin coated microcarriers. This process was repeated two more times, and after the final detachment the cells were seeded on 12-well plates for trilineage differentiation using a commercial protocol (STEMDIFF™ Trilinage Differentiation Kit, STEMCELL Technologies Canada Inc., Vancouver, BC). After trilineage differentiation, the cells from each lineage were stained with antibodies specific to markers specific to that lineage (available from BIOLEGEND®, San Diego, Calif. and Miltenyi Biotec, San Diego, Calif.) following the manufacturer's instructions. The cells grown and impeller-passaged on the INSCRIPTA™ bioreactors showed expression of lineage-specific markers similar to the cells grown on Matrigel and laminin coated plates.

The tri-lineage differentiation antibody staining protocol was performed in the following manner, with the equipment listed in Table 2 and the antibodies listed in Table 3:

TABLE 2

Foxp3/Transcription Factor Fixation/Permeabilization Concentrate and Diluent, ThermoFisher Scientific, cat. # 00-5521-00

TABLE 2-continued eBioscience™ Flow Cytometry Staining Buffer, ThermoFisher Scientific, cat. # 00-4222-26
FACS staining buffer (2% FBS, 1 mM EDTA, 0.5% BSA)
FACS buffer (2% FBS, 1 mM EDTA)
FACSMelody™ flow cytometer (Becton Dickinson, Inc., Franklin Lakes, NJ)

TABLE 3

| Marker | Cell Type | Antibody Link | Catalog # | Conjugate | Isotype | Isotype | Conc. |
|---|---|---|---|---|---|---|---|
| CXCR4 | Mesoderm | BioLegend | 306518 | BV421 | Mouse IgG2a, κ | BioLegend | 1:200 |
| NCAM1 | Mesoderm | BioLegend | 362510 | PE-Cy7 | Mouse IgG1, κ | BioLegend | 1:200 |
| Brachyury | Mesoderm | SantaCruz | sc-374321 AF488 | AF488 | Mouse IgG2b, κ | BioLegend | 1:25 |
| Nestin | Ectoderm | BioLegend | 656808 | BV421 | Mouse IgG2a, κ | BioLegend | 1:400 |
| Otx-2 | Ectoderm | Miltenyi | 130-121-202 | Vio B515 | recombinant hs IgG1 | Miltenyi | 1:100 |
| PAX6 | Ectoderm | Miltenyi | 130-123-250 | PE | recombinant hs IgG1 | Miltenyi | 1:400 |
| CXCR4 | Ectoderm | BioLegend | 306518 | BV421 | Mouse IgG2a, κ | BioLegend | 1:400 |
| SOX17 | Ectoderm | Miltenyi | 130-111-147 | Vio B515 | recombinant hs IgG1 | Miltenyi | 1:600 |
| FOXA2 | Ectoderm | BD Biosciences | 561589 | PE | Mouse IgG1, κ | BD Biosciences | >1:20 |

A single-cell suspension was prepared by lifting cells with TrypLE™ SELECT (ThermoFisher Scientific, Waltham, Mass., USA) and was centrifuged for 5 minutes at 200×g. The cells were washed in DPBS and centrifuged a second time. The cells were fixed with a Foxp3 kit (ThermoFisher Scientific, Waltham, Mass.) according to the manufacturer's instructions. Following incubation at room temperature in the dark for 30-60 minutes, 1 ml Foxp3 fixation/permeabilization working solution was added. Each sample contained <10M cells. A 1× working solution of permeabilization buffer was prepared by mixing 1 part of 10× Permeabilization Buffer with 9 parts of distilled water and 2 ml of 1× permeabilization buffer was added to each tube. The samples were centrifuged at 400-600×g for 5 minutes at room temperature. The supernatant was discarded and the pellet was resuspended in residual volume of 1× permeabilization buffer for a total volume of approximately 100 µl. The cells were diluted so that there were no more than 10,000 cells/µl in a 96-well V- or U-bottom plate. A master mix of antibodies per cell lineage in FACS staining buffer was prepared. Approximately 500,000 cells were stained in 50 µl of staining solution. The cells were incubated on ice in the dark for at least 30 minutes. 150 µl of FACS buffer was added to each well. The cells were then centrifuged at 500×g for 5 minutes at room temperature and the supernatant was discarded. The cells were resuspended in FACS buffer and analyzed by a flow cytometer on the FACSMelody™ flow cytometer.

Figure 18A:
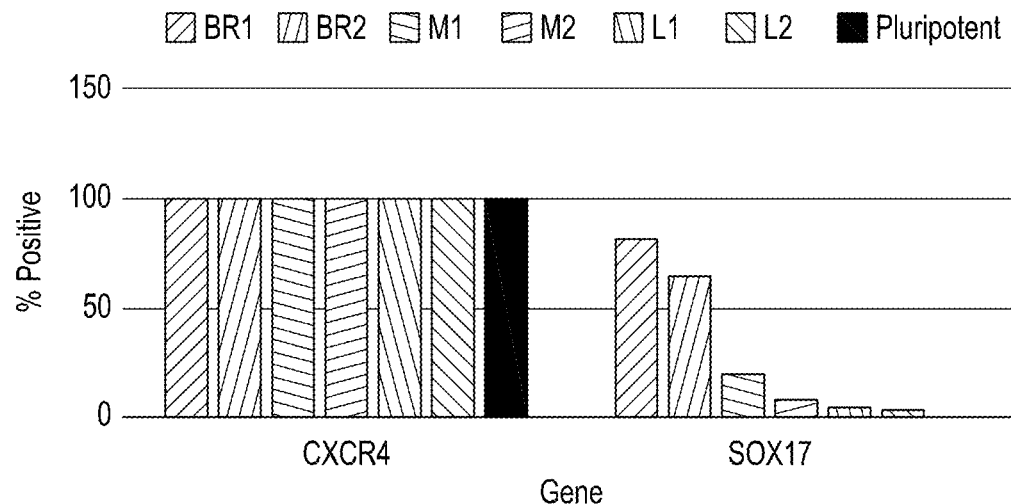
FIG. 18A-18F show a series of panels, both % positive and median fluorescence, demonstrating that iPSCs grown in the bioreactor described herein maintain differentiation potential comparable to iPSCs cultured on laminin plates and in MATRIGEL® plates (CORNING® BIOCOAT™ MATRIGEL® 6-well plates (Corning, Inc., Glendale, Ariz.)).
Figure 18B:
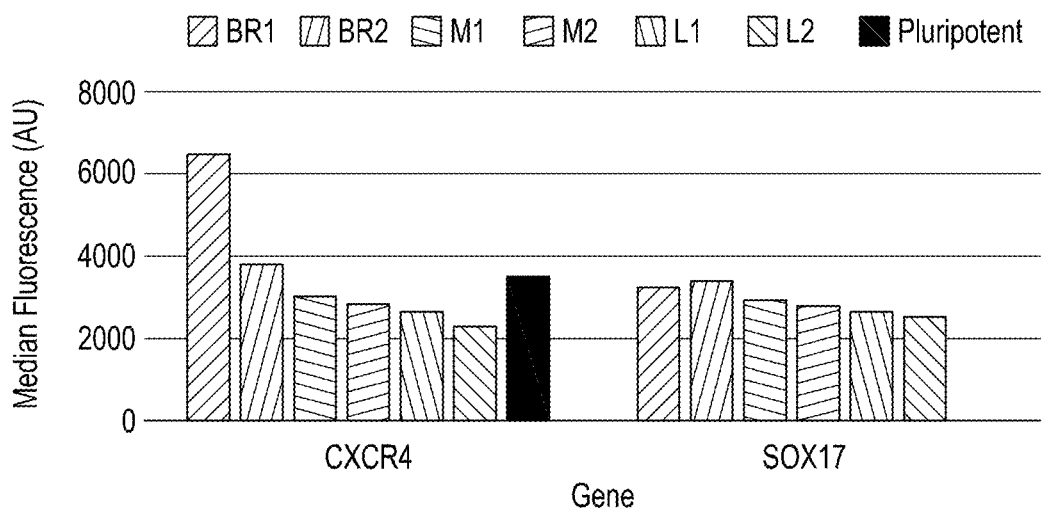
Figure 18C:
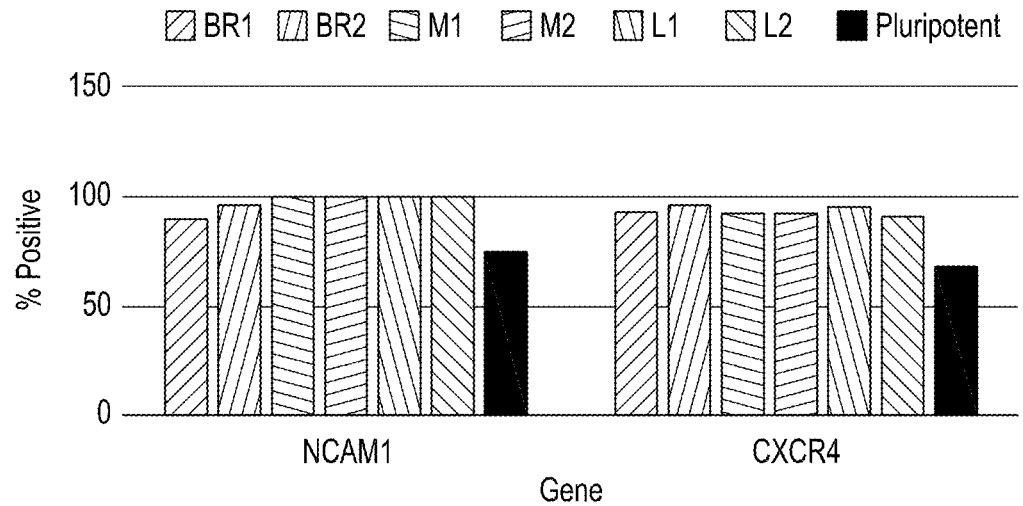
Figure 18D:
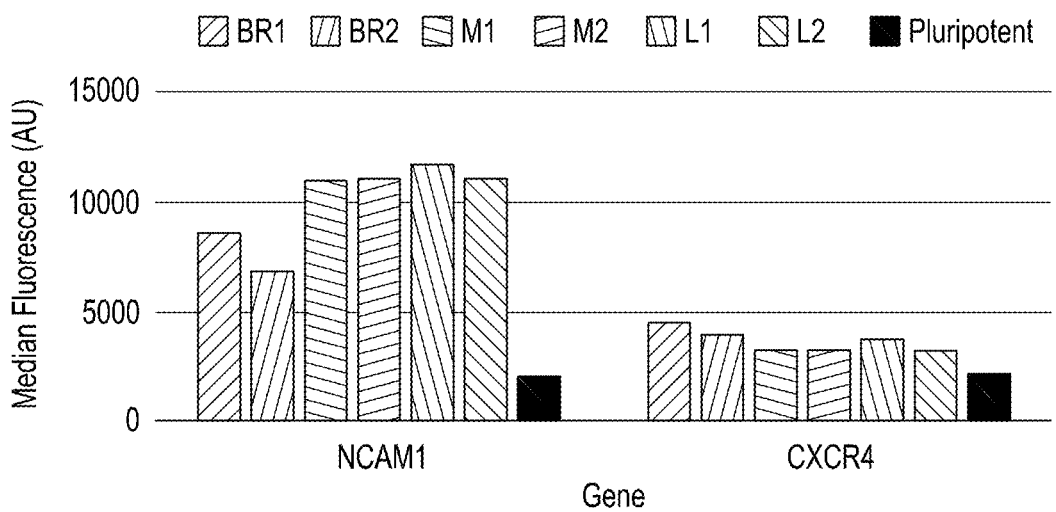
Figure 18E:
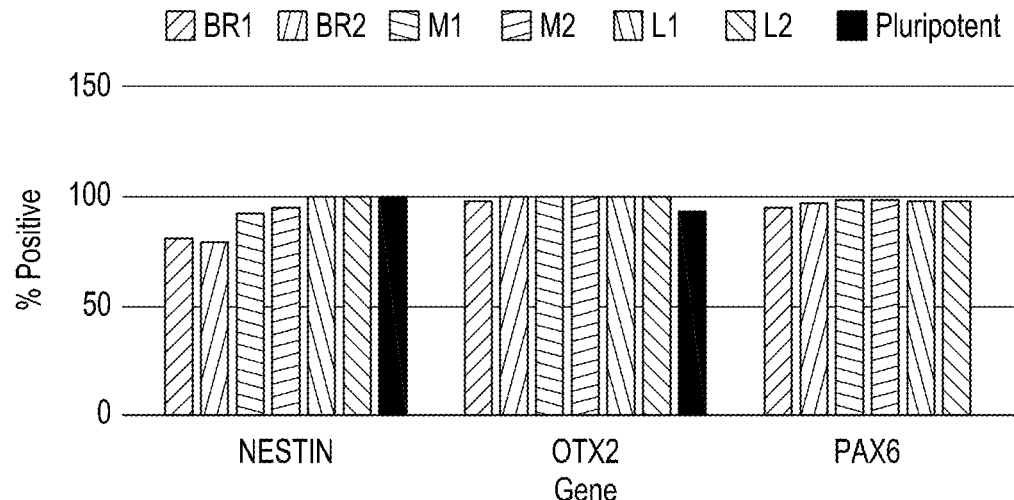
Figure 18F:
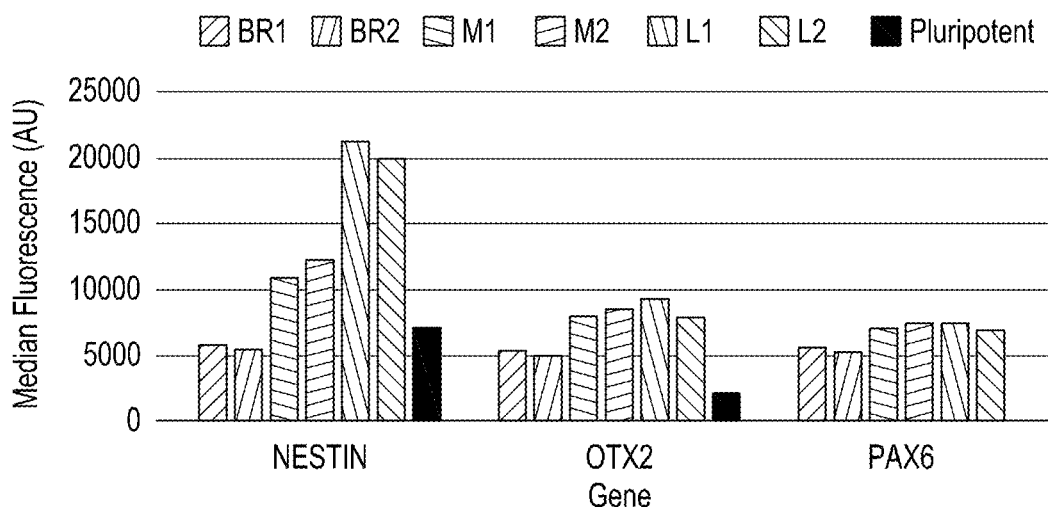

The results are shown in FIGS. 18A-18F. FIGS. 18A, 18C and 18E comprise a series of bar graphs showing % positive cells for endoderm markers CXCR4 and SOX17; mesoderm markers NCAM1 and CXCR4; and ectoderm markers NESTIN, OTX2 and PAX6. FIGS. 18B, 18D and 18E comprise a series of bar graphs showing median fluorescence obtained for the endoderm, mesoderm and ectoderm markers. BR1 indicates results for INSCRIPTA™ bioreactor 1, BR2 indicates results for INSCRIPTA™ bioreactor 2 (replicate), L1 indicates CORNING® BIOCOAT™ laminin plates (Corning, Inc., Glendale, Ariz.), L2 indicates CORNING® BIOCOAT™ laminin plates (Corning, Inc., Glendale, Ariz.) (replicate), M1 indicates CORNING® BIOCOAT™ MATRIGEL® 6-well plates (Corning, Inc., Glendale, Ariz.), and M2 indicates CORNING® BIOCOAT™ MATRIGEL® 6-well plates (Corning, Inc., Glendale, Ariz.) (replicate). Note that the cells grown in the bioreactors maintain differentiation potential roughly equivalent to cells grown in the laminin plates and MATRIGEL® plates. A pluripotent control was used, where the pluripotent control were cells that were not differentiated using the STEMDIFF medium (STEMDIFF™ Trilinage Differentiation Kit, STEMCELL Technologies Canada Inc., Vancouver, BC) but were maintained in mTeSRPlus medium (STEMCELL Technologies Canada INC., Vancouver, BC).

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. A method of growing cells, passaging the cells, editing the cells via nucleic acid-guided nuclease editing, and detaching the cells in a bioreactor, comprising the steps of:
providing a bioreactor comprising:
a growth vessel comprising a tapered main body, a lid assembly comprising ports, at least one driving impeller, and an impeller shaft, wherein there is at least one liquid-in port; at least one liquid-out port; at least one gas-in port; at least one gas-out port; at least one rupture disc; and at least one sensor port; and wherein the lid assembly makes an air-tight fitting on the tapered main body; and
a bioreactor stand assembly comprising a frame, a stand main body disposed in the frame, wherein the stand main body accommodates the tapered main body of the growth vessel during operation, and wherein the stand main body comprises a heating element to heat the tapered main body;
providing cell growth medium, cells, and first microcarriers to the tapered main body;
allowing the cells to attach to the first microcarriers;
providing a viral vector to the tapered main body of the growth vessel, wherein each viral vector comprises an editing cassette and a selection marker, and wherein the viral vector is provided to the cells at a multiplicity of infection of less than one;
allowing the viral vectors to transduce the cells on the first microcarriers to produce transduced cells;
monitoring growth of the transduced cells on the first microcarriers;
selecting for transduced cells via the selection marker;
detaching the transduced cells from the first microcarriers;
allowing the first microcarriers to settle in the tapered main body of the growth vessel;
removing the first microcarriers from the tapered main body of the growth vessel;
adding reagent bundle microcarriers to the tapered main body of the growth vessel, wherein the reagent bundle microcarriers comprise a lipofection agent and a nuclease;
allowing the transduced cells to attach to and grow on the reagent bundle microcarriers;
providing conditions for the nuclease to transfect the transduced cells to produce transfected cells;
monitoring growth of the transfected cells on the reagent bundle microcarriers;
detaching the transfected cells from the reagent bundle microcarriers;
allowing the reagent bundle microcarriers to settle in the tapered main body of the growth vessel;
removing the detached transfected cells to a separate vessel.

2. The method of claim 1, wherein the transduced and/or transfected cells are detached from the microcarriers via the at least one driving impeller.

3. The method of claim 1, wherein the lid assembly further comprises a motor integration port for a motor to control the at least one driving impeller.

4. The method of claim 1, wherein the bioreactor comprises a second driving impeller.

5. The method of claim 1, wherein the at least one sensor port in the lid assembly is configured to accommodate a sensor to monitor capacitance of the cells and medium in the tapered main body of the growth vessel; a sensor to measure $O_2$ concentration of the transduced and/or transfected cells and medium in the tapered main body of the growth vessel; a sensor to measure $CO_2$ of the transduced and/or transfected cells and medium in the tapered main body of the growth vessel; a sensor to measure pH of the transduced and/or transfected cells and medium in the tapered main body of the growth vessel; a sensor to measure lactate concentration of the transduced and/or transfected cells and medium in the tapered main body of the growth vessel; a sensor to measure glucose concentration of the transduced and/or transfected cells and medium in the tapered main body of the growth vessel; a sensor to measure biomass of the transduced and/or transfected cells and medium in the tapered main body of the growth vessel; or a sensor to measure optical density of the transduced and/or transfected cells and medium in the tapered main body of the growth vessel.

6. The method of claim 5, wherein there are at least two sensor ports in the lid assembly each configured to accommodate a sensor to monitor capacitance of the transduced and/or transfected cells and medium in the tapered main body of the growth vessel; a sensor to measure $O_2$ concentration of the transduced and/or transfected cells and medium in the tapered main body of the growth vessel; a sensor to measure $CO_2$ of the transduced and/or transfected cells and medium in the tapered main body of the growth vessel; a sensor to measure pH of the transduced and/or transfected cells and medium in the tapered main body of the growth vessel; a sensor to measure lactate concentration of the transduced and/or transfected cells and medium in the tapered main body of the growth vessel; a sensor to measure glucose concentration of the transduced and/or transfected cells and medium in the tapered main body of the growth vessel; a sensor to measure biomass of the transduced and/or transfected cells and medium in the tapered main body of the growth vessel; or a sensor to measure optical density of the transduced and/or transfected cells and medium in the tapered main body of the growth vessel.

7. The method of claim 1, wherein the lid assembly further comprises a temperature probe.

8. The method of claim 1, wherein the lid assembly further comprises a camera port.

9. The method of claim 1, wherein the heating element of the stand main body comprises a heat jacket.

10. The method of claim 9, wherein the heat jacket comprises LED lights.

11. The method of claim 9, wherein the heat jacket comprises a camera port.

12. The method of claim 1, wherein the at least one liquid-out port comprises a filter.

13. The method of claim 1, wherein the tapered main body of the growth vessel accommodates cell culture volumes of 25 ml to 500 ml.

14. The method of claim 1, wherein during cell growth revolutions per minute of the at least one driving impeller is approximately 40-80 rpm.

15. The method of claim 1, wherein during cell detachment revolutions per minute of the at least one driving impeller is approximately 2700 rpm.

16. The method of claim 15, wherein a chemical agent is added to the tapered main body of the growth vessel to aid in detaching the transduced and/or transfected cells.

17. The method of claim 16, wherein the chemical agent is hemagglutinin, collagenase, dispase or trypsin.

18. The method of claim 1, wherein the nuclease is provided as a protein.

19. The method of claim 1, wherein the nuclease is provided as a nucleic acid coding sequence under control of a promoter.

20. The method of claim 19, wherein the tapered main body is optically transparent in UV and IR ranges.

21. The method of claim 1, wherein the tapered main body is optically transparent.

22. The method of claim 1, wherein the stand frame is fabricated from stainless steel.

23. The method of claim 1, wherein the bioreactor further comprises a liquid handling system wherein the liquid handling system comprises a manifold with one or more connections to the bioreactor.

24. The method of claim 1, wherein the bioreactor further comprises a liquid handling system, wherein the liquid handling system comprises reagent receptacles individually connected to the growth module.

25. The method of claim 1, wherein the cells are induced pluripotent stem cells (iPSCs).

26. The method of claim 1, wherein the cells are primary cells.

27. The method of claim 1, wherein the microcarriers are fabricated from natural organic materials, biocompatible synthetic polymers, or inorganic materials.

28. The method of claim 27, wherein the microcarriers are coated with laminin.

29. The method of claim 1, wherein the viral vector is a lentiviral vector.

30. The method of claim 1, wherein the viral vector is an adeno-associated virus vector or an oncoretrovirus vector.

* * * * *